(12) United States Patent
Verma et al.

(10) Patent No.: US 10,695,348 B2
(45) Date of Patent: Jun. 30, 2020

(54) SULFONYL PYRIDYL TRP INHIBITORS

(71) Applicant: Genentech, Inc., South San Francisco, CA (US)

(72) Inventors: Vishal Verma, South San Francisco, CA (US); Matthew Volgraf, South San Francisco, CA (US); Baihua Hu, Beijing (CN)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 16/269,973

(22) Filed: Feb. 7, 2019

(65) Prior Publication Data

US 2019/0167681 A1    Jun. 6, 2019

Related U.S. Application Data

(63) Continuation of application No. PCT/EP2017/070261, filed on Aug. 10, 2017.

(51) Int. Cl.

| C07D 401/02 | (2006.01) |
|---|---|
| C07D 401/12 | (2006.01) |
| C07D 401/14 | (2006.01) |
| C07D 515/04 | (2006.01) |
| A61K 31/506 | (2006.01) |
| C07D 491/048 | (2006.01) |
| A61P 11/00 | (2006.01) |

(52) U.S. Cl.
CPC ............ *A61K 31/506* (2013.01); *A61P 11/00* (2018.01); *C07D 401/14* (2013.01); *C07D 491/048* (2013.01)

(58) Field of Classification Search
CPC .. C07D 401/02; C07D 401/12; C07D 401/14; C07D 515/04
See application file for complete search history.

(56) References Cited

U.S. PATENT DOCUMENTS

| 3,773,919 | A | 11/1973 | Boswell et al. |
|---|---|---|---|
| 4,485,045 | A | 11/1984 | Regan |
| 4,544,545 | A | 10/1985 | Ryan et al. |
| 5,004,697 | A | 4/1991 | Pardridge et al. |
| 5,112,596 | A | 5/1992 | Malfroy-Camine |
| 5,268,164 | A | 12/1993 | Kozarich et al. |
| 5,506,206 | A | 4/1996 | Kozarich et al. |
| 5,686,416 | A | 11/1997 | Kozarich et al. |
| 10,179,782 | B2 * | 1/2019 | Estrada ............... C07D 403/12 |
| 2002/0025313 | A1 | 2/2002 | Micklus et al. |
| 2002/0038086 | A1 | 3/2002 | Hynynen et al. |
| 2002/0065259 | A1 | 5/2002 | Schatzberg et al. |
| 2003/0073713 | A1 | 4/2003 | Schoenhard |
| 2003/0162695 | A1 | 8/2003 | Schatzberg et al. |
| 2004/0131692 | A1 | 8/2004 | Kreuter et al. |
| 2004/0204354 | A1 | 10/2004 | Nelson et al. |
| 2005/0089473 | A1 | 4/2005 | Black et al. |
| 2005/0124533 | A1 | 6/2005 | Schatzberg et al. |

FOREIGN PATENT DOCUMENTS

| EP | 0102324 A2 | 3/1984 |
|---|---|---|
| EP | 0133988 A2 | 8/1984 |
| EP | 2805718 A1 | 11/2014 |
| WO | 2010/141805 A1 | 12/2010 |
| WO | 2015/052264 A1 | 4/2015 |
| WO | 2016/128529 A1 | 8/2016 |
| WO | 2018/015410 A1 | 1/2018 |
| WO | 2018/015411 A1 | 1/2018 |

OTHER PUBLICATIONS

ACkley, David C., et al. Optimization in Drug Discovery: In Vitro Methods "Metabolic Stability Assessed by Liver Microsomes and Hepatoeytes" Yan, Zhengyin, ed., Totowa, New Jersey Humana Press,:151-162 (Jan. 1, 2004).

Agopyan, N., et al., "TRPV1 receptors mediate particulate matter-induced apoptosis" Am J Physiol Lung Cell Mol Physiol 286:L563-L572 (Oct. 30, 2003).

Agopyan, N., et al., "Vanilloid receptor activation by 2- and 10-μm particles induces responses leading to apoptosis in human airway epithelial cells" Toxicol Appl Pharm 192:21-35 (May 28, 2003).

Alsenz, J. et al., "High throughput solubility measurement in drug discovery and development" Adv Drug Deliver Rev 59:546-567 (May 29, 2007).

Ansel's Pharmaceutical Dosage Forms and Drug Delivery Systems (Table of Contents only, in 6 pages), Allen et al., 8th edition, Philadelphia, PA: Lippineott Williams & Wilkins, ( 2004).

Asai, Hideaki, et al., "Heat and mechanical hyperalgesia in mice model of cancer pain" PAIN 117: 19-29 (May 3, 2005).

Banker, M.J., et al., "Plasma/ Serum Protein Binding Determinations" Curr Drug Metab 9:854-859 (Jul. 28, 2008).

Barton, N.J., et al., "Attenuation of experimental arthritis in TRPV1R knockout mice" Exp Mol Pathol 81:166-170 (Jun. 16, 2006).

Bobo et al., "Convection-enhanced delivery of macromolecules in the brain" PNAS USA 91:2076-2080 ( 1994).

(Continued)

*Primary Examiner* — Bruck Kifle
(74) *Attorney, Agent, or Firm* — Robert C. Hall

(57) ABSTRACT

The invention provides compounds of formula I:

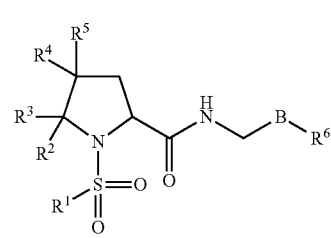

and pharmaceutically acceptable salts thereof where $R^1$ is a substituted or unsubstituted phenyl or a fused bicyclic comprising a substituted or unsubstituted phenyl. In addition, the present invention relates to methods of manufacturing and methods of using the compounds of formula I as well as pharmaceutical compositions containing such compounds. The compounds may be useful in treating diseases and conditions mediated by TRPA1, such as pain.

10 Claims, No Drawings

(56) References Cited

OTHER PUBLICATIONS

Bolcskei, Kata, et al., "Investigation of the role of TRPV1 receptors in acute and chronic nociceptive processes using gene-deficient mice" PAIN 117:368-376 (Jun. 27, 2005).
Bundgaard a Textbook of Drug Design and Development; Chapter 5 "Design and Application of Prodrugs":113-191 ( 1991).
Bundgaard et al., "(C) Means to Enhance Penetration (1) Prodrugs as a means to improve the delivery of peptide drugs" Adv Drug Deliver Rev 8:1-38 ( 1992).
Bundgaard, "Design of prodrugs: Bioreversible derivatives for various functional groups and chemical entities" Design of Prodrugs:1 ( 1985).
Chan, C., et al., "Sensory fibres expressing capsaicin receptor TRPV1 in patients with rectal hypersensitivity and faecal urgency" Lancet 361:385-391 (Feb. 1, 2003).
Coffey, S. Rodd's Chemistry of Carbon Compounds Coffey, S., Second edition, Elsevier B.V.: Elsevier B.V., vol. I-IV ( 2008).
De Yebenes et al., "Continuous Intraeerebroventrieular Infusion of Dopamine and Dopamine Agonists Through a Totally Implanted Drug Delivery System in Animal Models of Parkinson's Disease" Movement Disorders 2(3): 143-158 ( 1987).
Dinis, Paulo, et al., "Anandamide-Evoked Activation of Vanilloid Receptor 1 Contributes to the Development of Bladder Hyperreflexia and Nociceptive Transmission to Spinal Dorsal Horn Neurons in Cystitis" J Neurol Sci 24(50): 11253-11263 (Dec. 15, 2004).
Eppstein et al., "Biological activity of liposome-encapsulated murine interferon y is mediated by a cell membrane receptor" PNAS USA 82(11):3688-3692 (Jun. 1985).
Fleisher et al., "Improved oral drug delivery: solubility limitations overcome by the use of prodrugs" Adv Drug Deliver Rev 19:115-130 ( 1996).
Geppetti, P., et al., "Activation and sensitisation of the vanilloid receptor: role in gastrointestinal inflammation and function" Brit J Pharmacol 141 : 13 13-1320 (Mar. 29, 2004).
Ghilardi, J.R., et al., "Selective Blockade of the Capsaicin Receptor TRPV1 Attenuates Bone Cancer Pain" J Neurol Sci 25(12):3126-3131 (Mar. 23, 2005).
Gill et al., "Direct Brain Infusion of Glial Cell Line-Derived Neurotrophic Factor in Parkinson Disease" Nature Med. 9:589-595 (Mar. 31, 2003).
Goadsby, P. J., "Post-triptan Era for the Treatment of Acute Migraine" Curr Pain Head Reports 8:393-398 (Jan. 1, 2004).
Harbaugh, "Intracerebroventricular cholinergic drug administration in Alzheimer's disease: preliminary results of a double-blind study" J. Neural. Transm. 24 Suppl.:271-277 (1987).
Ho Fiesers' Reagents for Organic Synthesis (Table of Contents, in 5 pages), Hoboken, New Jersey:John Wiley & Sons, Inc., vol. 23 ( 2007).
Honore, P., et al., "A-425619 [1-Isoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats" J Pharmacol Exp Ther 314(1):410-421 (Apr. 14, 2005).
Hwang et al., "Hepatic uptake and degradation of unilamellar sphingomyelin/cholesterol liposomes: a kinetic study" PNAS USA 77:4030-4034 ( 1980).
"International Preliminary Report on Patentability—PCT/EP2017/070261": pp. 1-7 (Feb. 21, 2019).
"International Search Report—PCT/EP2017/070261": pp. 1-5 (Sep. 20, 2017).
Kakeya et al., "Studies on Prodrugs of Cephalosporins.I. ///superscript: 1)/// Synthesis and Biological Properties of Glycyloxbenzoyloxymethyl and Glycylaminobenzoyloxymethyl Esters of 7β-[2-(2-Aminothiazol-4yl)-(Z)-2-methoxyiminoacetamido]-3-3-methyl-3-cephem-4-carboxylic Acid" Chem. Pharm. Bull. 32(2):692-698 ( 1984).
Kariv, I. et al., "Development of a High Throughput Equilibrium Dialysis Method" J Pharm Sci 90(5):580-587 (May 1, 2001).

Kibbey, C.E., et al., "An Integrated Process for Measuring the Physicochemical Properties of Drug Candidates in a Preclinical Discovery Environment" J Pharm Sci 90(8):1164-1175 (Jan. 27, 2001).
Kimball, E.S., et al., "Vanilloid receptor 1 antagonists attenuate disease severity in dextran sulphate sodium-induced colitis in mice" Neurogastroent Motil 16:811-818 (Jan. 5, 2004).
Kosugi, Masafumi, et al., "Activation of TRPA1 Channel Facilitates Excitatory Synaptic Transmission in Substantia Gelatinosa Neurons of the Adult Rat Spinal Cord" J Neurol Sci 27(16):4443-4451 (Apr. 18, 2007).
Kremeyer, Barbara, et al., "A Gain-of-Function Mutation in TRPA1 Causes Familial Episodic Pain Syndrome" NEURO 66:671-680 (Jun. 10, 2010).
Lalloo, Umesh G., et al., "Capsazepine inhibits cough induced by capsaicin and citric acid but not by hypertonic saline in guinea pigs" J Appl Physiol:1082-1087 (May 23, 1995).
Langer et al., "Biocompatibility of Polymeric Delivery Systems for Macromolecules" J. Biomed. Mater. Res. 15:267-277 (1981).
Menendez, L., et al., "Analgesic effects of capsazepine and resiniferatoxin on bone cancer pain in mice" Neurosci Lett 393:70-73 (Sep. 19, 2005).
Neuwelt, E. A. Implications of the Blood-Brain Barrier and Its Manipulation Neuwelt, E.A., ed, Plenum Publishing Corporation-Springer, Vol. vols. 1-2: 1-434, (Jan. 1, 1989).
Nielsen et al., "Glycolarnide Esters as Biolabile Prodrugs of Carboxylic Acid Agents: Synthesis, Stability, Bioconversion, and Physicochemical Properties" J Pharmacol Sci 77(4):285 ( 1988).
Notari, Robert, et al. Methods of Enzymology: Drug and Enzyme Targeting "Theory and Practice of Prodrug Kinetics" Widder, Kenneth J ., eds, First edition, Waltham, MA: Academic Press, vol. 112:309-396 (Jun. 11, 1985).
Papanastassiou et al., "The Potential for Efficacy of the Modified (ICP 34.5) Herpes Simplex Virus HSV1716 Following Intratumoural Injection into Human Malignant Glioma: A Proof of Principle Study" Gene Ther 9:398-406 (Apr. 2, 2002).
Pomonis, J.D., et al., "N-(4-Tertiarybutylphenyl)-4-(3-cholorphyridin-2-yl) tetrahydropyrazine-1 (2H)-carbox-amide (BCTC), a Novel, Orally Effective Vanilloid Receptor 1 Antagonist with Analgesic Properties: II. In Vivo Characterization in Rat Models of Inflammatory and Neuropathic Pain" J Pharmacol Exp Ther 306(1):387-393 (Apr. 31, 2003).
Remington: The Science and Practice of Pharmacy (Cover and Table of Contents only, total in 4 pages), Gennaro et al., 20th edition, Philadelphia, PA: Lippincott Williams & Wilkins, ( 2000).
Robinson et al., "Discovery of the Hemifumarate and (α-L-Alanyloxy)methyl Ether as Prodrugs of an Antirheumatic Oxindole: Prodrugs for the Enolic OH Group" J. Med. Chem. 39:10-18 ( 1996).
Rowe, et al., Handbook of Pharmaceutical Excipients (Cover and Table of Contents only, total in 6 pages), Rowe et al., 5th edition, Grayslake, IL: Pharmaceutical Press, ( 2005).
Sanchez, Maria, et al., "Expression of the transient receptor potential vanilloid 1 (TRPV1) in LNCaP and PC-3 prostate cancer cells and in human prostate tissue" Eur J Pharmacol 515:20-27 (Apr. 8, 2005).
Sculptoreanu, A., et al., "Protein kinase C contributes to abnormal capsaicin responses in DRG neurons from cats with feline interstitial cystitis" Neurosci Lett 381:42-46 (Jan. 28, 2005).
Sidman et al., "Controlled Release of Macromolecules and Pharmaceuticals from Synthetic Polypeptides Based on Glutamic Acid" Biopolymers 22(1):547-556 (1983).
Szabo, A., et al., "Role of Transient Receptor Potential Vanilloid 1 Receptors in Adjuvant-Induced Chronic Arthritis: In Vivo Study Using Gene-Deficient Mice" J Pharmacol Exp Ther 314(1):111-119 (Apr. 5, 2005).
Walker, Katherine, et al., "The VR1 Antagonist Capsazepine Reverses Mechanical Hyperalgesia in Models of Inflammatory and Neuropathic Pain" J Pharmacol Exp Ther 304(1):56-62 (Sep. 9, 2002).
Wei, Hong, et al., "Spinal transient receptor potential ankyrin 1 channel contributes to central pain hypersensitivity in various pathophysiological conditions in the rat" PAIN 152:582-591 (Nov. 29, 2010).

(56) References Cited

OTHER PUBLICATIONS

Wei, Hong, et al., "Spinal TRPA1 ion channels contribute to cutaneous neurogenic inflammation in the rat" Neurosci Lett 479:253-256 (May 23, 2010).
Yan, Zhengyin, et al., "Stable-Isotope Trapping and High-Throughput Screenings of Reactive Metabolites Using the Isotope MS Signature" Anal Chem 76(23):6835-6847 (Dec. 1, 2004).
Yiangou, Y., et al., "Vanilloid receptor 1 immunoreactivity in inflamed human bowel" Lancet 357:1338-1339 (Apr. 28, 2001).

* cited by examiner

SULFONYL PYRIDYL TRP INHIBITORS

CROSS-REFERENCE TO RELATED APPLICATION

This application is a continuation of International Patent Application Number PCT/EP2017/070261 filed on Aug. 10, 2017, which claims priority benefit of International Patent Application Number PCT/CN2016/094836 filed on Aug. 12, 2016, the disclosures of which are incorporated herein in their entirety.

FIELD OF THE INVENTION

The present invention relates to sulfonyl pyridyl compounds, their manufacture, pharmaceutical compositions containing them and their use as Transient Receptor Potential (TRP) channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a chemosensor.

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., J. Neurosci 27, (2007) 4443-4451; Kremayer et al., Neuron 66 (2010) 671-680; Wei et al., Pain 152 (2011) 582-591); Wei et al., Neurosci Lett 479 (2010) 253-256)) providing additional rationale for the utility of small molecule TRPA1 inhibitors in the treatment of pain disorders.

BRIEF DESCRIPTION OF THE INVENTION

In some embodiments, a compound or a pharmaceutically acceptable salt thereof of the following formula I is provided

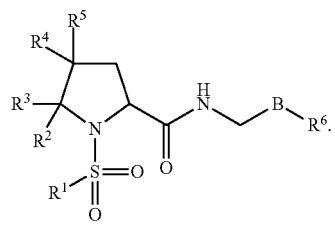

I

B is selected from $B^1$, $B^2$ and $B^3$. $B^1$ is a 5-membered heteroaryl comprising 2 nitrogen atoms in the ring, wherein each 5-membered heteroaryl is unsubstituted or substituted with one or more groups independently selected from halogen, CN, $(C_{1-6})$alkyl, $(C_{1-6})$haloalkyl, $O(C_{1-6})$alkyl, and $O(C_{1-6})$haloalkyl. $B^2$ is phenyl, wherein each phenyl is unsubstituted or substituted with one or more groups independently selected from halogen, CN, $(C_{1-6})$alkyl, $(C_{1-6})$haloalkyl, $O(C_{1-6})$alkyl, and $O(C_{1-6})$haloalkyl. $B^3$ is 6-membered heteroaryl, wherein each 6-membered heteroaryl is unsubstituted or substituted with one or more groups independently selected from halogen, CN, $(C_{1-6})$alkyl, $(C_{1-6})$haloalkyl, $O(C_{1-6})$alkyl, $O(C_{1-6})$haloalkyl, 5 or 6-membered heteroaryl, $(C_{3-7})$cycloalkyl, and 4, 5, 6, or 7-membered heterocyclyl, wherein any of the 5 or 6-membered heteroaryl, $(C_{3-7})$cycloalkyl, or 4, 5, 6, or 7-membered heterocyclyl groups is unsubstituted or substituted with one or more groups independently selected from halogen, CN, $(C_{1-6})$alkyl, $(C_{1-6})$haloalkyl, $O(C_{1-6})$alkyl, and $O(C_{1-6})$haloalkyl.

$R^1$ is selected from the group consisting of:

(i) unsubstituted pyridyl selected from

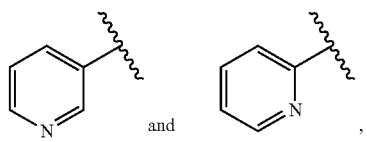 [SMILES: *c1cccnc1 ; *c1ccccn1]

and (ii) a pyridyl selected from

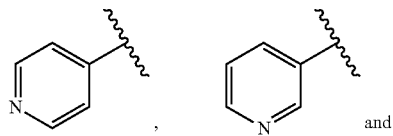

and

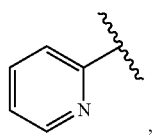

, wherein said pyridyl is substituted with one or more groups independently selected from halogen, CN, $(C_{1-6})$alkyl, and $(C_{1-6})$haloalkyl, wherein, when the pyridyl is

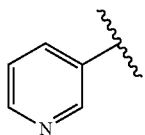

(a) and wherein said pyridyl is substituted with fluorine, the substituted pyridyl is selected from

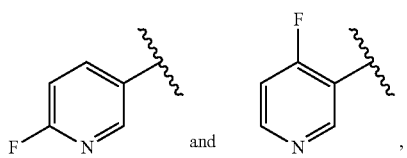 [SMILES: *c1ccc(F)nc1 ; *c1cnccc1F]

(b) and wherein said pyridyl is substituted with chlorine, the substituted pyridyl is selected from

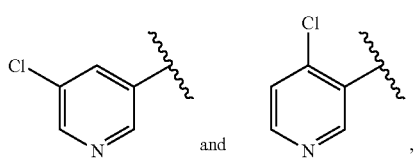 [SMILES: *c1cncc(Cl)c1 ; *c1cnccc1Cl]

(c) and wherein said pyridyl is substituted with cyano, the substituted pyridyl is selected from

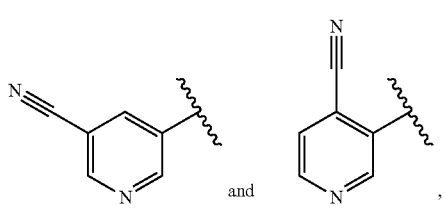 [SMILES: *c1cncc(C#N)c1 ; *c1cnccc1C#N]

and (iii) a fused bicyclic ring system comprising a 2-pyridyl, 3-pyridyl or 4-pyridyl ring and a fused saturated, partially saturated or unsaturated ring having from 4 to 6 atoms and 1 or 2 heteroatoms independently selected from N, O and S, wherein the bicyclic ring system is unsubstituted or is substituted with one or more groups independently selected from halogen, CN, $(C_{1-6})$alkyl.

$R^2$ is selected from $(C_{1-6})$alkyl, $(C_{1-6})$haloalkyl, $(C_{3-7})$cycloalkyl, and $(C_{1-6})$alkyl-$(C_{3-7})$cycloalkyl, wherein $(C_{1-6})$alkyl is optionally substituted with $O(C_1-C_6)$alkyl.

$R^3$ is H or $(C_{1-6})$alkyl or $R^2$ and $R^3$ together with the atoms to which they are attached form a $(C_3)$cycloalkyl.

$R^4$ is selected from H, F and CN.

$R^5$ is H or $(C_{1-6})$alkyl, or one of $R^2$ and $R^3$ and one of $R^4$ and $R^5$ together with the atoms to which they are attached form a $(C_3)$cycloalkyl.

$R^6$ is phenyl, $(C_{3-7})$cycloalkyl, 5 or 6-membered heteroaryl, or 4, 5, 6 or 7-membered heterocycle, wherein any phenyl, $(C_{3-7})$cycloalkyl, 5 or 6-membered heteroaryl, or 4, 5, 6 or 7-membered heterocycle of $R^6$ is optionally substituted with one or more groups independently selected from halogen, CN, $SF_5$, $(C_{1-6})$alkyl, $(C_{1-6})$haloalkyl, $O(C_{1-6})$alkyl and $O(C_{1-6})$haloalkyl, or $R^6$ is $O-CH_2-R^7$.

$R^7$ is $(C_{1-6})$alkyl, 4, 5, 6, or 7-membered heterocycle, $(C_{3-7})$cycloalkyl, or 6-membered heteroaryl, wherein any $(C_{1-6})$alkyl, 4, 5, 6, or 7-membered heterocycle, $(C_{3-7})$cycloalkyl, or 6-membered heteroaryl is optionally substituted with one or more groups independently selected from halogen, CN, $(C_{1-6})$alkyl, $(C_{1-6})$haloalkyl, $O(C_{1-6})$alkyl, $(C_{3-7})$cycloalkyl, and $O(C_{1-6})$haloalkyl.

In other embodiments, the following compounds or pharmaceutically acceptable salts thereof are provided:

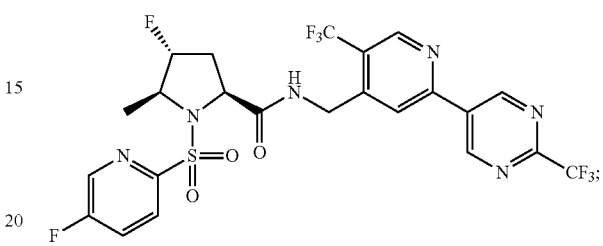

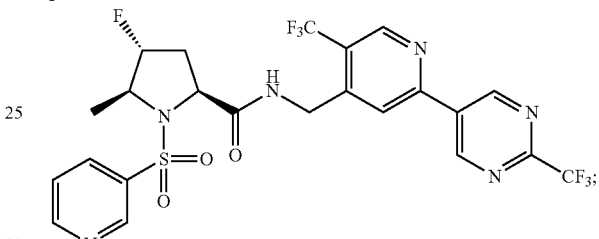

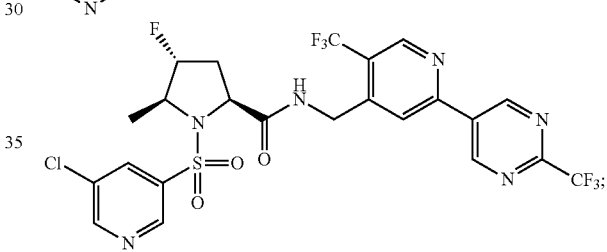

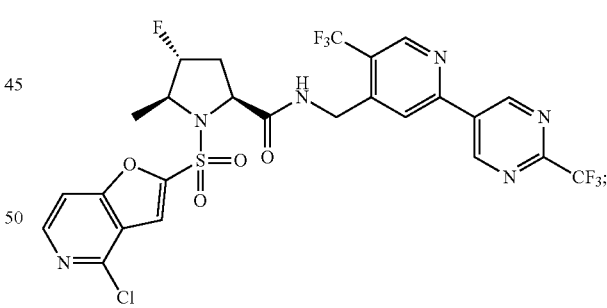

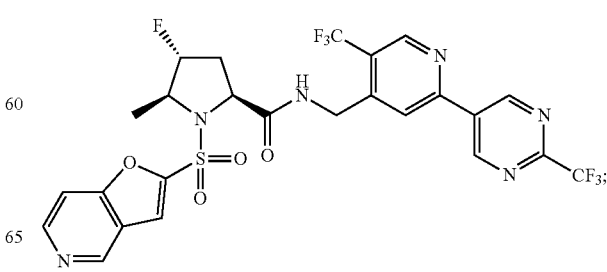

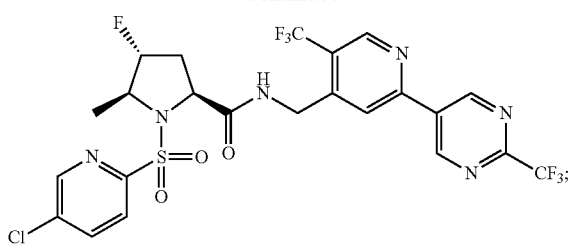
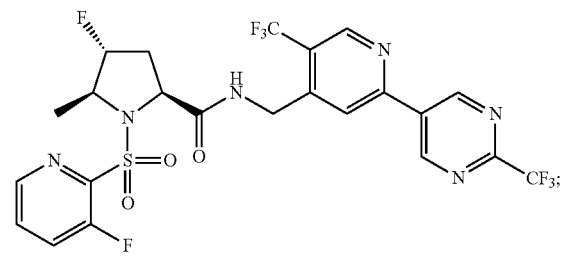
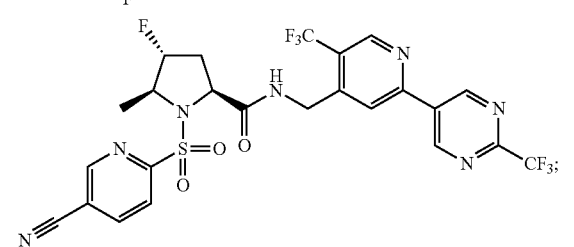
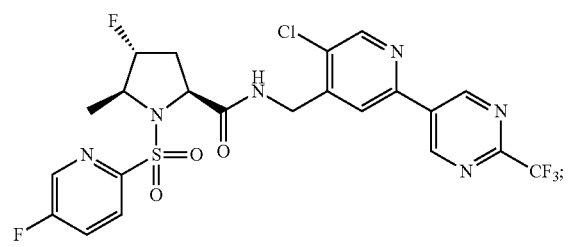
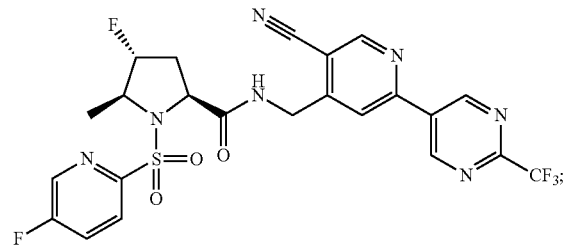
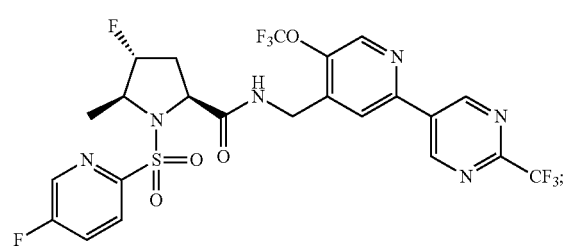
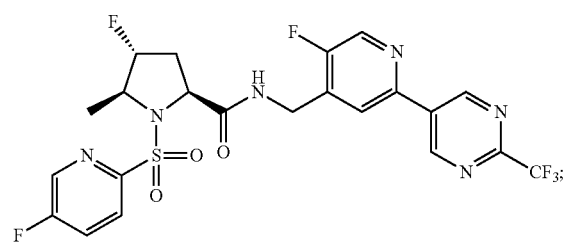
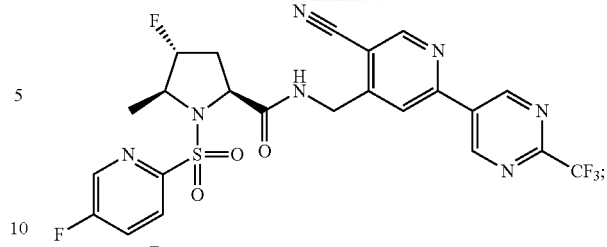
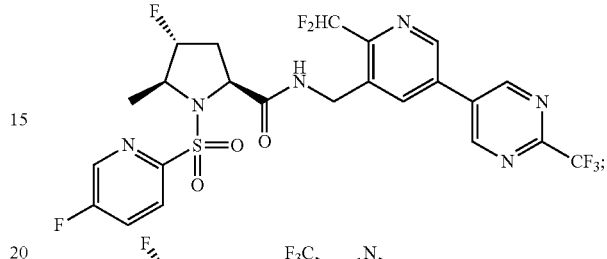
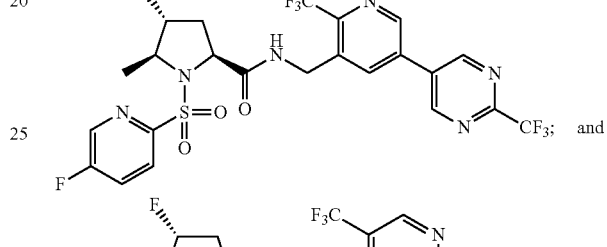
and
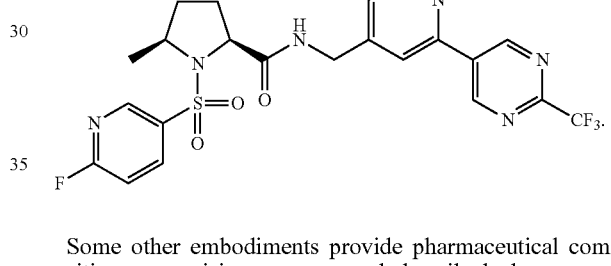

Some other embodiments provide pharmaceutical compositions comprising a compound described above, or a pharmaceutically acceptable salt thereof, and a pharmaceutically acceptable carrier, diluent or excipient.

Some other embodiments provide a compound as described above, or a pharmaceutically acceptable salt thereof, for use in medical therapy.

Some other embodiments provide a compound as described above, or a pharmaceutically acceptable salt thereof, for the treatment or prophylaxis of a respiratory disorder.

Some other embodiments provide a compound as described above, or a pharmaceutically acceptable salt thereof, for the preparation of a medicament for the treatment or prophylaxis of a respiratory disorder.

Some other embodiments provide a method for treating a respiratory disorder in a mammal comprising, administering a compound as described above, or a pharmaceutically acceptable salt thereof, to the mammal.

Some other embodiments provide a compound as described above, or a pharmaceutically acceptable salt thereof, for modulating TRPA1 activity.

Some other embodiments provide a compound as described above, or a pharmaceutically acceptable salt thereof, for the treatment or prophylaxis of a disease or condition mediated by TRPA1 activity.

Some other embodiments provide a use of a compound as described above, or a pharmaceutically acceptable salt thereof, for the preparation of a medicament for the treatment or prophylaxis of a disease or condition that is mediated by TRPA1 activity.

Some other embodiments provide a method for modulating TRPA1 activity, comprising contacting TRPA1 with a compound as described above, or a pharmaceutically acceptable salt thereof.

Some other embodiments provide a method for treating a disease or condition mediated by TRPA1 activity in a mammal, comprising administering a compound as described above, or a pharmaceutically acceptable salt thereof, to the mammal.

DETAILED DESCRIPTION OF THE INVENTION

Definitions

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$ to $R^5$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms.

The term "alkoxy" denotes a group of the formula —O—R', wherein R' is an alkyl group. Examples of alkoxy moieties include methoxy, ethoxy, isopropoxy, and tert-butoxy.

"Aryl" means a cyclic aromatic hydrocarbon moiety having a mono-, bi- or tricyclic aromatic ring of 6 to 16 carbon ring atoms. The aryl group can be optionally substituted as defined herein. Examples of aryl moieties include, but are not limited to, phenyl, naphthyl, phenanthryl, fluorenyl, indenyl, pentalenyl, azulenyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted. In one embodiment the aryl has 6 to 14 carbon ring atoms (i.e., ($C_6$-$C_{14}$) aryl). In another embodiment the aryl has 6 to 10 carbon ring atoms (i.e., ($C_6$-$C_{10}$)aryl).

The term "heteroaryl" denotes an aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "pyridyl" and "pyridinyl", as used herein, interchangably refer to a saturated heterocyclic moiety having six atoms in the ring including one nitrogen atom.

The terms "halo", "halogen" and "halide", which may be used interchangeably, refer to a substituent fluoro, chloro, bromo, or iodo.

The term "haloalkyl" denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

"Cycloalkyl" means a saturated or partially unsaturated carbocyclic moiety having mono- or bicyclic (including bridged bicyclic) rings and 3 to 10 carbon atoms in the ring. The cycloalkyl moiety can optionally be substituted with one or more substituents. In particular embodiments cycloalkyl contains from 3 to 8 carbon atoms (i.e., (C3-C8) cycloalkyl). In other particular embodiments cycloalkyl contains from 3 to 6 carbon atoms (i.e., (C3-C6)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a "spirocycloakyl" fashion such as "spirocyclopropyl":

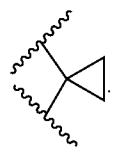

"Heterocycle" or "heterocyclyl" refers to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4 heteroatoms selected from oxygen, nitrogen and sulfur in the ring with the remaining ring atoms being carbon. In particular embodiments heterocycle or heterocyclyl refers to a 4, 5, 6 or 7-membered heterocycle. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, 2-azabicyclo[2.2.1]heptanyl, octahydroindolyl, or tetrahydroquinolinyl.

In the context of $R^1$, as used herein, "fused bicyclic" refers to a fused ring system as follows:

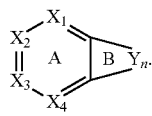

Ring A is pyridyl wherein one of the atoms $X_1$ to $X_4$ is N and the remaining atoms are C. Ring B is saturated, partially saturated or unsaturated, n is 2 to 4, each Y is independently a C, N, O or S atom, where one or two Y atoms are independently N, O or S.

Unless otherwise indicated, the term "hydrogen" or "hydro" refers to the moiety of a hydrogen atom (—H) and not $H_2$.

The term "respiratory disorder" includes chronic obstructive pulmonary disorder (COPD), asthma, allergic rhinitis, bronchospasm, and cystic fibrosis.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula I, which can be useful as an intermediate for isolating or purifying a compound of formula I. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Examples 1 to 17, 19 and 20 and Tables 1 and 2 structures for illustrative purposes, while stereochemistry is definitively established, such as from x-ray crystallographic data.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

One embodiment of the present invention provides for compounds of formula I:

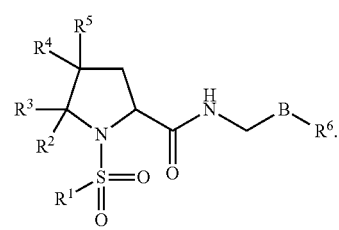

In some embodiments, $R^1$ is an unsubstituted pyridyl selected from

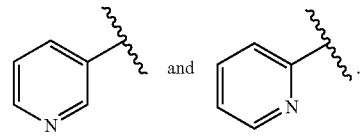 [SMILES: *c1cccnc1 ; *c1ccccn1]

In some embodiments, $R^1$ is a pyridyl selected from

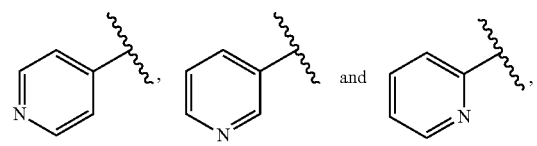

wherein said pyridyl is substituted with one or more groups independently selected from halogen, CN, $(C_{1-6})$alkyl, and $(C_{1-6})$haloalkyl. In some particular embodiments, $R^1$ is substituted with one or more groups independently selected from Br, Cl, F, CN, $CH_3$, $CF_2H$ and $CF_3$. In some other particular embodiments, $R^1$ is substituted with F, Cl or CN. In such embodiments, when the pyridyl is

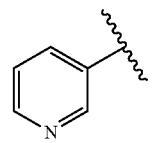 [SMILES: *c1cccnc1]

and is substituted with fluorine, and more particularly substituted with a single fluorine, the substituted pyridyl is selected from

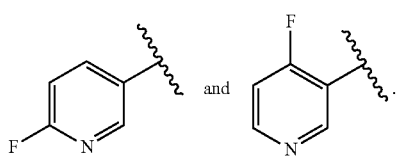 [SMILES: *c1ccc(F)nc1 ; *c1cnccc1F] and

In such embodiments, when the pyridyl is

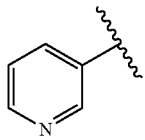

and is substituted with chlorine, and more particularly substituted with a single chlorine, the substituted pyridyl is selected from

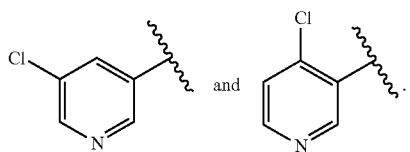 [SMILES: *c1cncc(Cl)c1 ; *c1cnccc1Cl] and

In such embodiments, when the pyridyl is

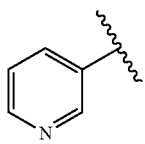

and is substituted with cyano, and more particularly substituted with a single cyano, the substituted pyridyl is selected from

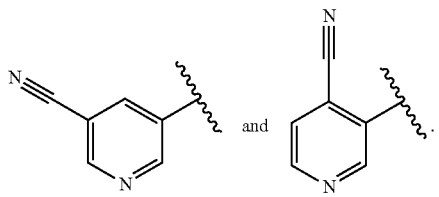 [SMILES: *c1cncc(C#N)c1 ; *c1cnccc1C#N] and

In some embodiments, $R^1$ is a fused bicyclic ring system comprising a 2-pyridyl, 3-pyridyl or 4-pyridyl ring fused with a saturated, partially saturated or unsaturated ring having from 4 to 6 atoms and 1 or 2 heteroatoms independently selected from N, O and S, wherein the bicyclic ring system is unsubstituted or is substituted with one or more groups independently selected from halogen, CN, $(C_{1-6})$ alkyl.

In some embodiments, $R^1$ is selected from:

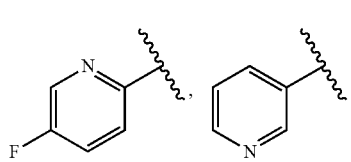

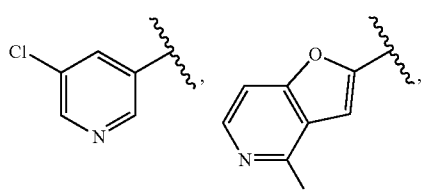

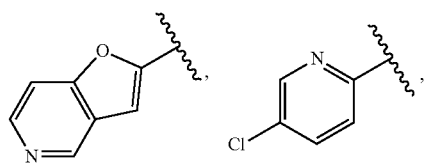

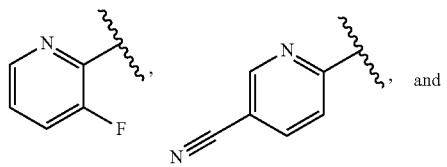, and

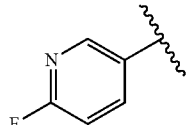

In some embodiments, $R^1$ is:

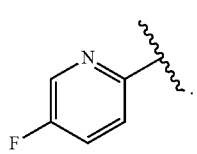

In some embodiments, $R^1$ is:

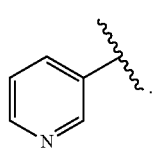 [SMILES: *c1cccnc1]

In some embodiments, $R^1$ is:

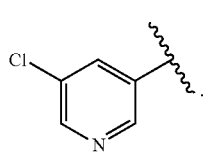 [SMILES: *c1cncc(Cl)c1]

In some embodiments, R¹ is:

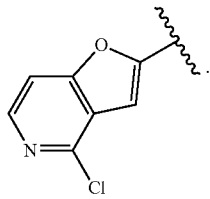 [SMILES: *c1cc2c(Cl)nccc2o1]

In some embodiments, R¹ is:

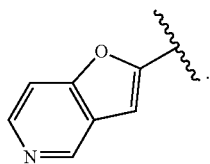 [SMILES: *c1cc2cnccc2o1]

In some embodiments, R¹ is:

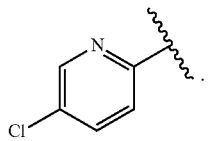

In some embodiments, R¹ is:

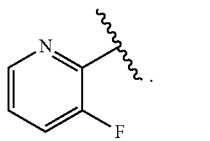 [SMILES: *c1ncccc1F]

In some embodiments, R¹ is:

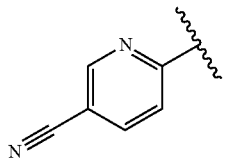

In some embodiments, R¹ is:

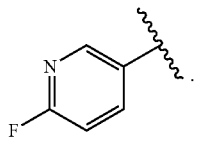

R² is selected from $(C_{1-6})$alkyl, $(C_{1-6})$haloalkyl, $(C_{3-7})$cycloalkyl, and $(C_{1-6})$alkyl-$(C_{3-7})$cycloalkyl, wherein $(C_{1-6})$alkyl is optionally substituted with $O(C_1-C_6)$alkyl. In some embodiments, R² is selected from $(C_{1-6})$alkyl, $CH_3$, $CH_2CH_3$, $C(CH_3)_3$ and $C(CF_3)_3$, $CH_2OCH_3$, and -cyclopropyl. In some other embodiments, R² and R³ together with the atoms to which they are attached form a $(C_3)$cycloalkyl. In some other embodiments, R² and R³ together with the atoms to which they are attached form a spirocyclopropyl.

In some embodiments, R³ is H or $(C_{1-6})$alkyl. In some embodiments, R² and R³ together with the atoms to which they are attached form a $(C_3)$cycloalkyl. In some embodiments R³ is H.

R⁴ is selected from H, F and CN. In some embodiments, R⁴ is H. In some embodiments, R⁴ is F. In some embodiments, R⁴ is CN.

R⁵ is H or $(C_{1-6})$alkyl. In some embodiments, R⁵ is H or $CH_3$.

In some embodiments, one of R² and R³ and one of R⁴ and R⁵ together with the atoms to which they are attached form a $(C_3)$cycloalkyl.

In some embodiments, the group

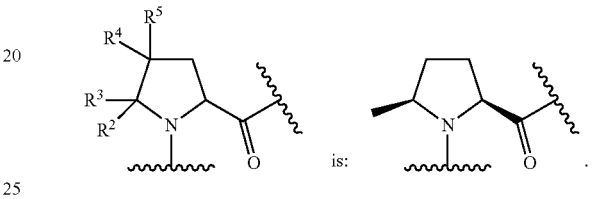

In some embodiments, the group

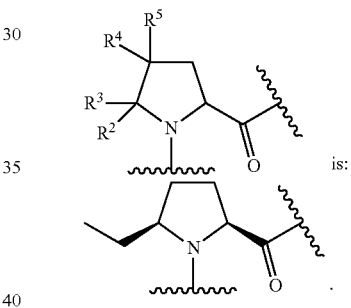

In some embodiments, the group

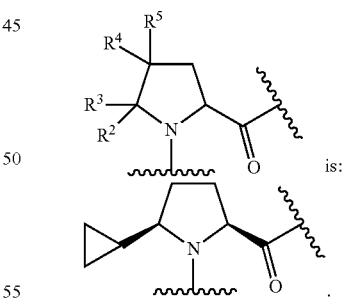

In some embodiments, the group

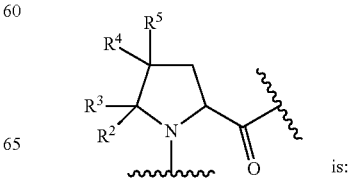

-continued

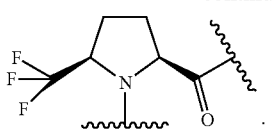

In some embodiments, the group

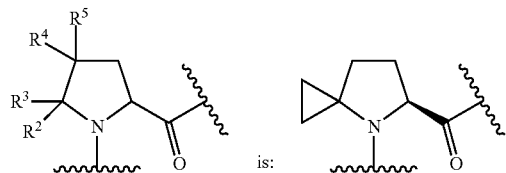

In some embodiments, the group

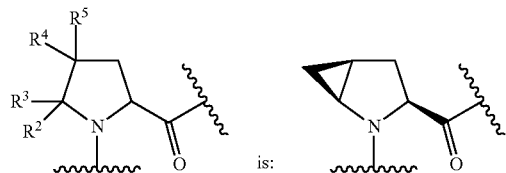

In some embodiments, the group

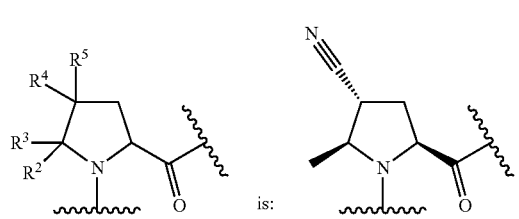

In some embodiments, the group

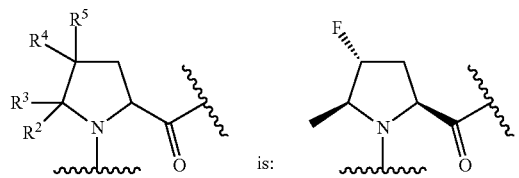

In some embodiments, the group

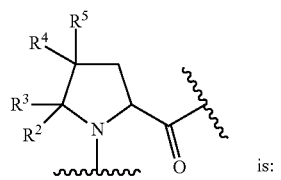

-continued

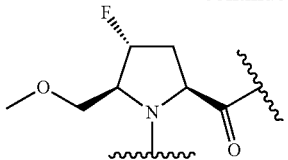

$R^6$ is phenyl, $(C_{3-7})$cycloalkyl, 5 or 6-membered heteroaryl, or 4, 5, 6 or 7-membered heterocycle, wherein any phenyl, $(C_{3-7})$cycloalkyl, 5 or 6-membered heteroaryl, or 4, 5, 6 or 7-membered heterocycle of $R^6$ is optionally substituted with one or more groups independently selected from halogen, CN, $SF_5$, $(C_{1-6})$alkyl, $(C_{1-6})$haloalkyl, $O(C_{1-6})$alkyl and $O(C_{1-6})$haloalkyl, or $R^6$ is O—$CH_2$—$R^7$.

In some embodiments, $R^6$ is 4, 5, 6 or 7-membered heterocycle. In some embodiments, $R^6$ is 4-membered heterocycle. In some embodiments, $R^6$ is 5-membered heterocycle. In some embodiments, $R^6$ is 6-membered heterocycle. In some embodiments, $R^6$ is 7-membered heterocycle. In some embodiments, $R^6$ is 5-membered heteroaryl. In some embodiments, $R^6$ is 6-membered heteroaryl. In some embodiments, $R^6$ is $(C_{3-7})$cycloalkyl. In some embodiments, $R^6$ is $(C_6)$cycloalkyl.

In some embodiments, $R^6$ is pyridinyl. In some embodiments, $R^6$ is pyrimidinyl. In some embodiments, $R^6$ is pyrazinyl. In some embodiments, $R^6$ is phenyl.

In some embodiments, $R^6$ is selected from the following:

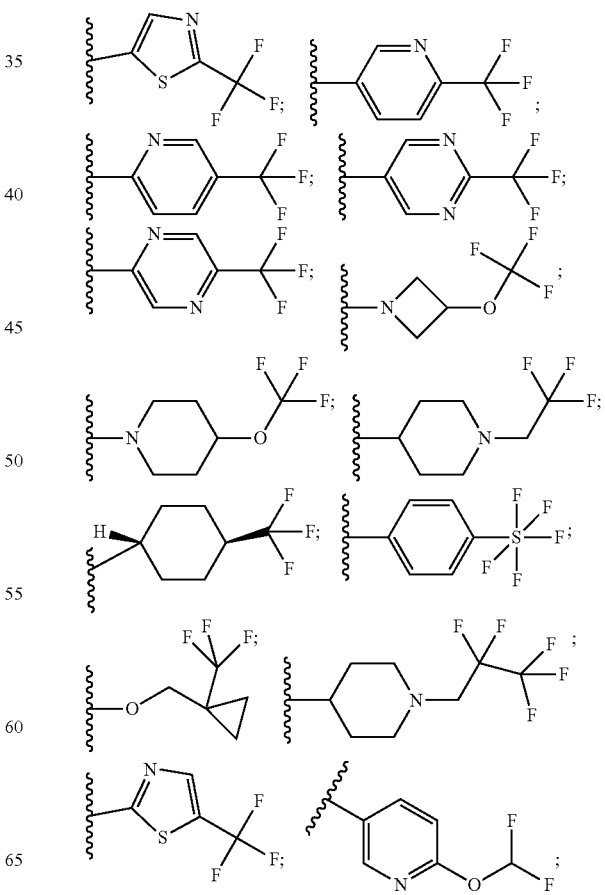

-continued

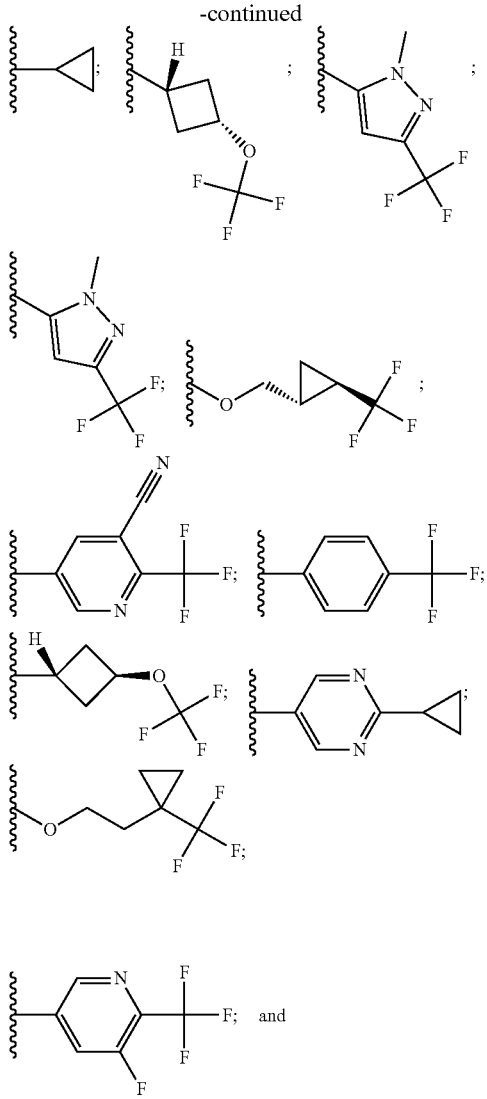

R[7] is (C$_{1-6}$)alkyl, 4, 5, 6, or 7-membered heterocycle, (C$_{3-7}$)cycloalkyl, or 6-membered heteroaryl, wherein any (C$_{1-6}$)alkyl, 4, 5, 6, or 7-membered heterocycle, (C$_{3-7}$) cycloalkyl, or 6-membered heteroaryl is optionally substituted with one or more groups independently selected from halogen, CN, (C$_{1-6}$)alkyl, (C$_{1-6}$)haloalkyl, O(C$_{1-6}$)alkyl, (C$_{3-7}$)cycloalkyl, and O(C$_{1-6}$)haloalkyl. In some embodiments, R[7] is (C$_{1-6}$)alkyl. In some embodiments, R[7] is (C$_{3-7}$)cycloalkyl. In some embodiments, R[7] is (C$_3$)cycloalkyl.

B is selected from B[1], B[2] and B[3] as described elsewhere herein.

In some embodiments, the compounds are salts of formula I.

One embodiment provides for compounds of formula II:

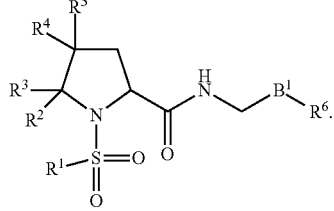

II

In such embodiments, B[1] is a 5-membered heteroaryl comprising two nitrogen atoms in the ring, wherein each 5-membered heteroaryl is unsubstituted or substituted with one or more groups independently selected from halogen, CN, (C$_{1-6}$)alkyl, (C$_{1-6}$)haloalkyl, O(C$_{1-6}$)alkyl, and O(C$_{1-6}$) haloalkyl.

In some such embodiments, B[1] is unsubstituted or substituted pyrazolyl.

In some such embodiments, B[1] is selected from:

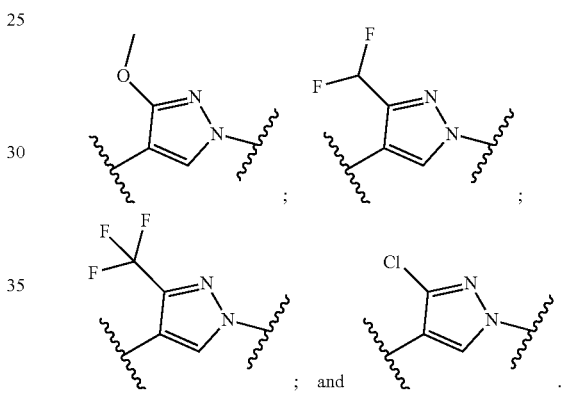

One embodiment provides for compounds of formula III:

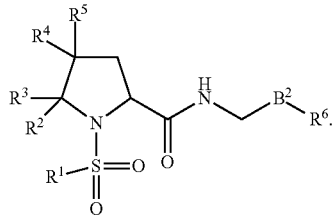

III

In such embodiments, B[2] is phenyl, wherein each phenyl is unsubstituted or substituted with one or more groups independently selected from halogen, CN, (C$_{1-6}$)alkyl, (C$_{1-6}$)haloalkyl, O(C$_{1-6}$)alkyl, and O(C$_{1-6}$)haloalkyl.

In some such embodiments, B[2] is selected from:

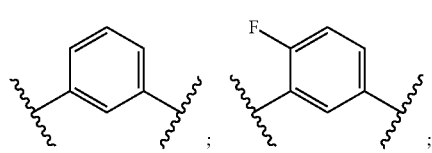

-continued

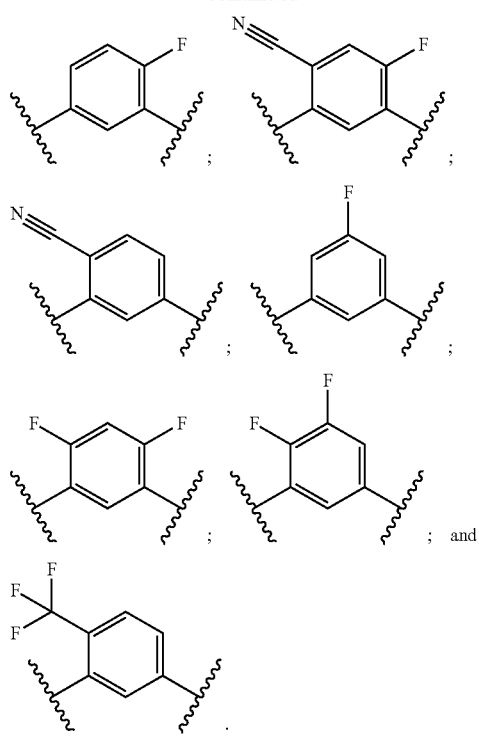

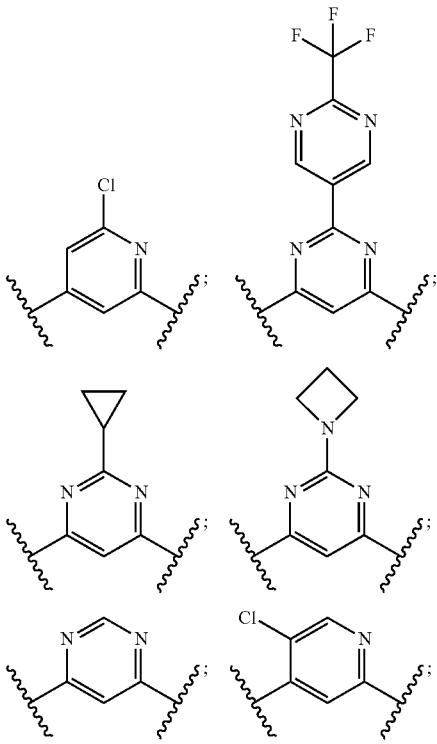

One embodiment provides for compounds of formula IV:

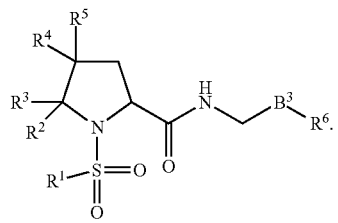
IV

In such embodiments, B³ is 6-membered heteroaryl, wherein each 6-membered heteroaryl is unsubstituted or substituted with one or more groups independently selected from halogen, CN, $(C_{1-6})$haloalkyl, $O(C_{1-6})$alkyl, $O(C_{1-6})$haloalkyl, 5 or 6-membered heteroaryl, $(C_{3-7})$cycloalkyl, and 4, 5, 6, or 7-membered heterocyclyl; and wherein any of the 5 or 6-membered heteroaryl, $(C_{3-7})$cycloalkyl, or 4, 5, 6, or 7-membered heterocyclyl groups is unsubstituted or substituted with one or more groups independently selected from halogen, CN, $(C_{1-6})$alkyl, $(C_{1-6})$haloalkyl, $O(C_{1-6})$alkyl, and $O(C_{1-6})$haloalkyl.

In some such embodiments, B³ is selected from:

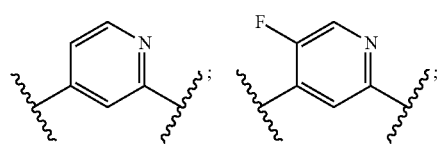

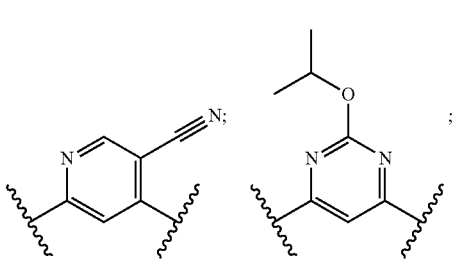

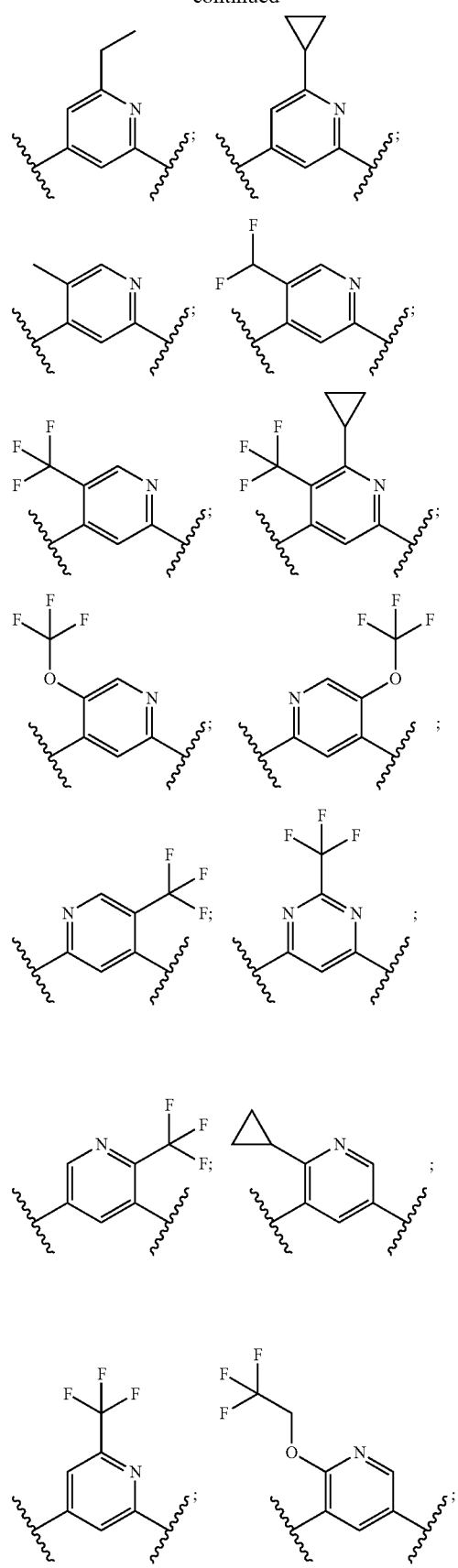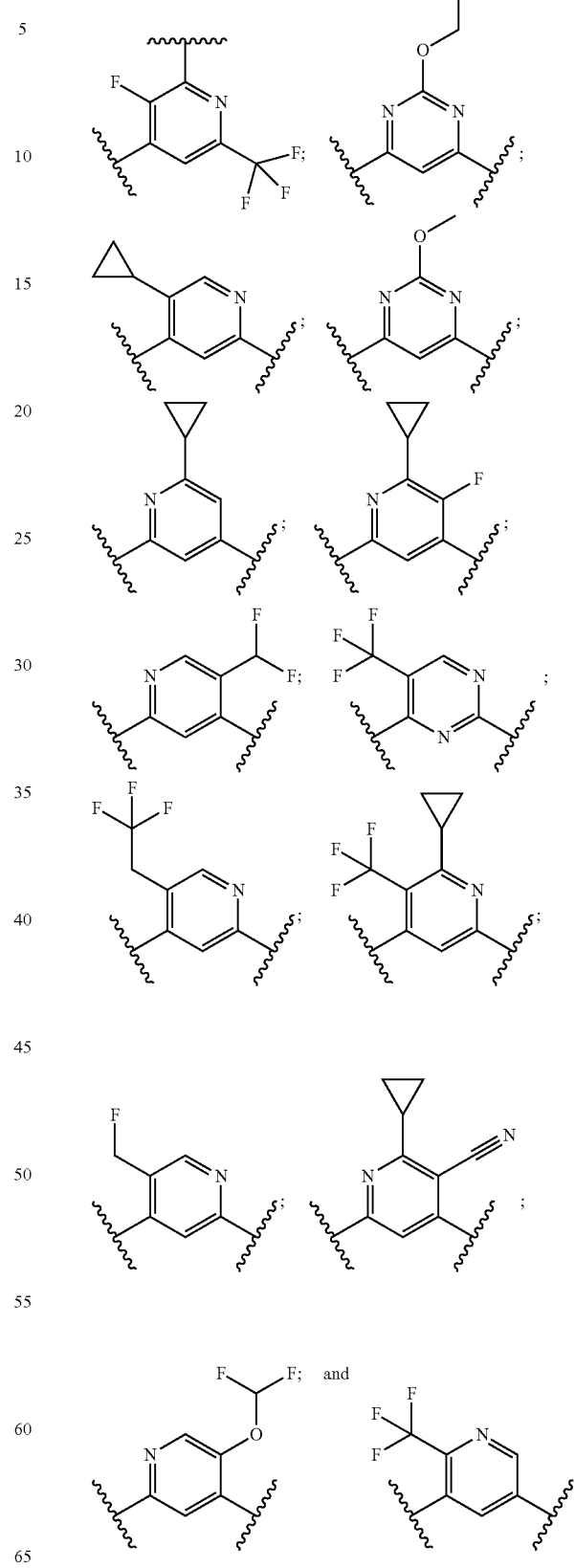

In some embodiments of the disclosure, B is selected from:
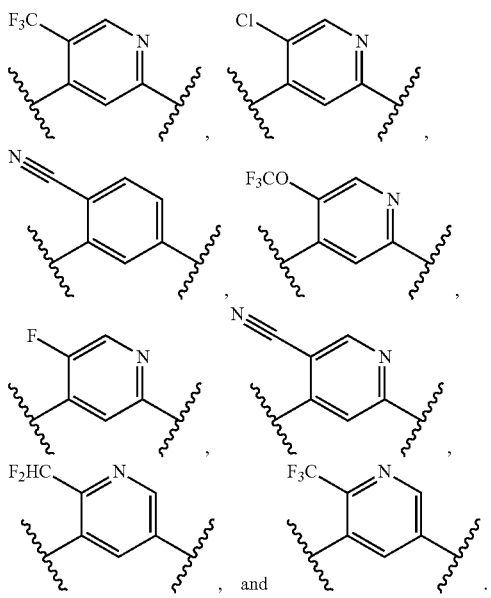
In some embodiments, R² is CH₃, R³ is H, R⁴ is F, R⁵ is H, and R⁶ is
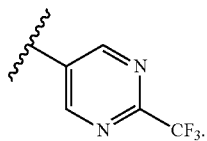
In some such embodiments, R¹ is selected from:
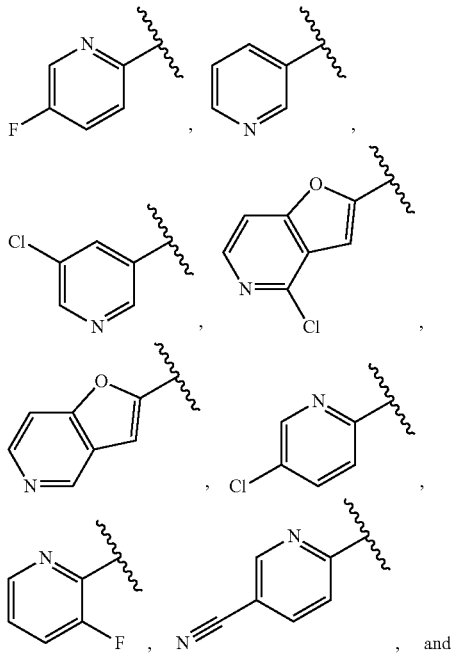
-continued
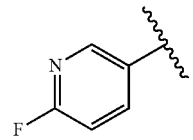
In some such embodiments, B is selected from:
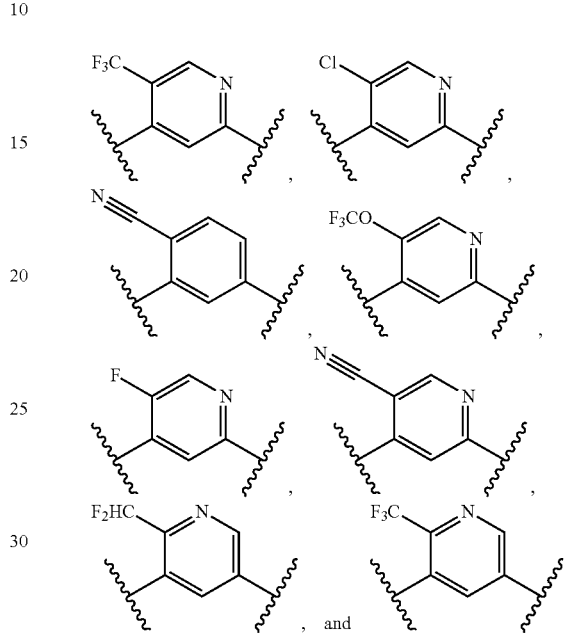
In some embodiments of the present disclosure, formula I is a compound selected from:
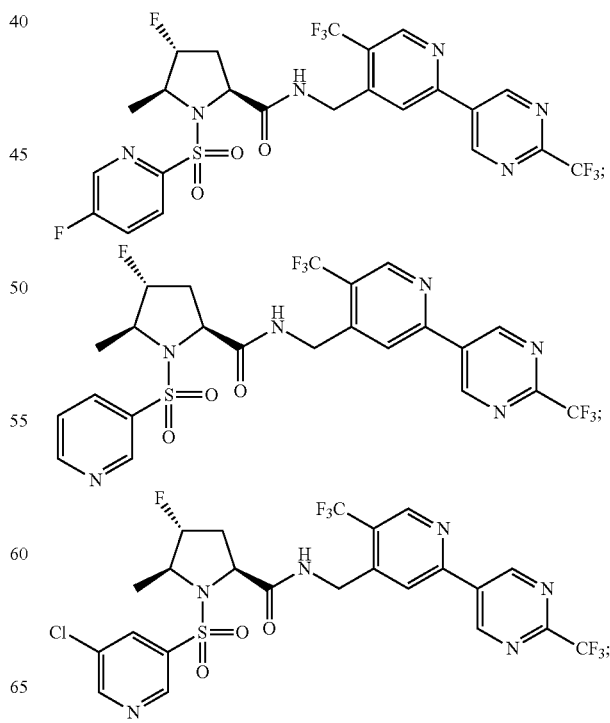

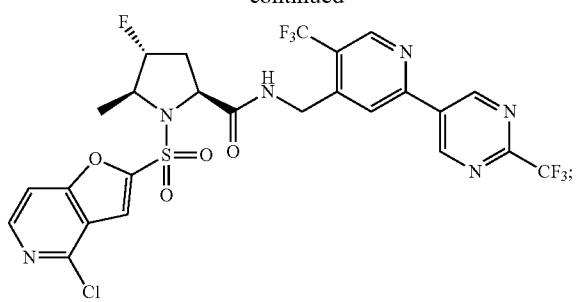
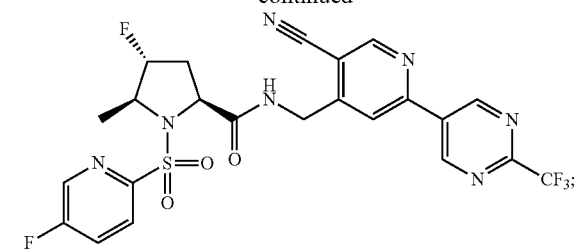
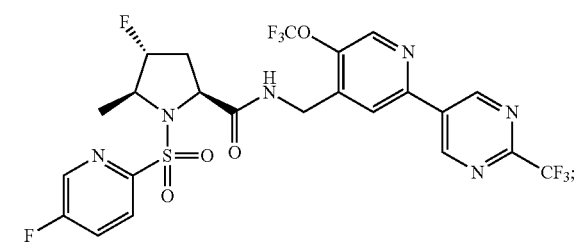
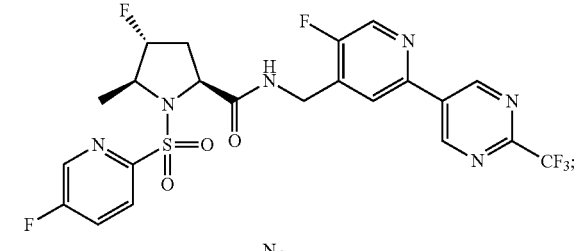
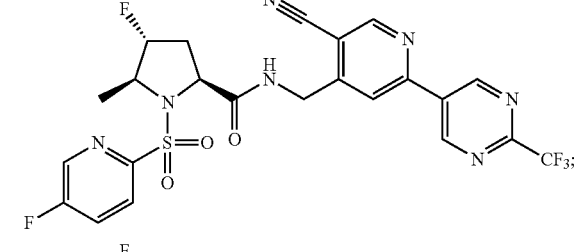
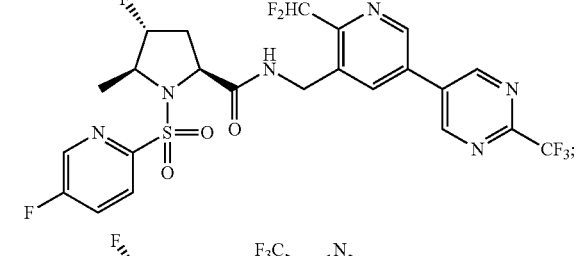
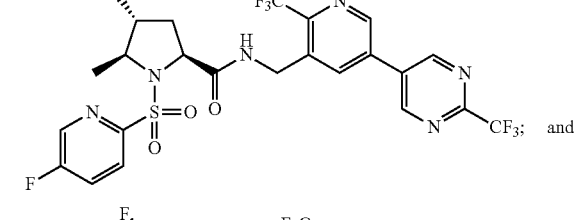
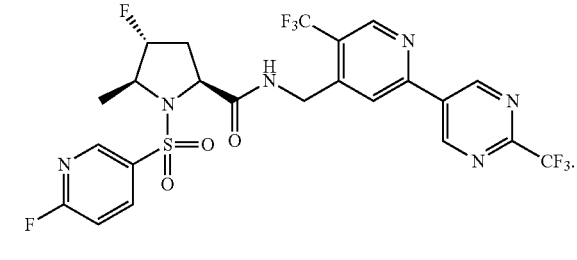

In some particular embodiments, formula I is a compound selected from:

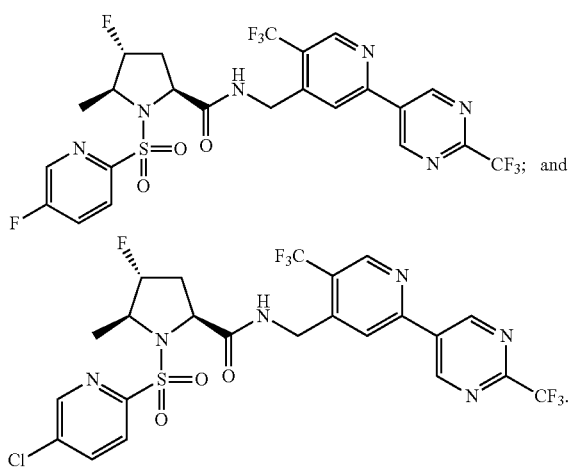

In this regard it should be noted that the following compounds are excluded from the scope of the present disclosure:

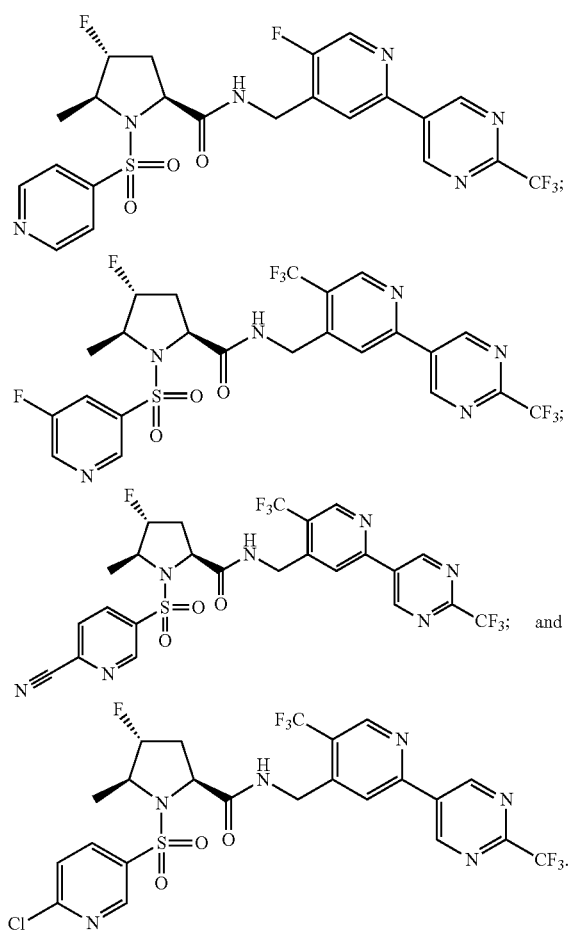

Based on experimental evidence to date, it is believed that the sulfonyl pyridyl TRPA1 inhibitor compounds of the present disclosure provide certain pharmacokinetic advantages such as, for instance, reduced human protein plasma binding and/or human liver microsome stability that correlates with reduced clearance.

In another embodiment of the invention, the compounds of formula I are isotopically-labeled by having one or more atoms therein replaced by an atom having a different atomic mass or mass number. Such isotopically-labeled (i.e., radio-labeled) compounds of formula I are considered to be within the scope of this invention. Examples of isotopes that can be incorporated into the compounds of formula I include isotopes of hydrogen, carbon, nitrogen, oxygen, phosphorous, sulfur, fluorine, chlorine, and iodine, such as, but not limited to, $^2H$, $^3H$, $^{11}$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of formula I, for example, those incorporating a radioactive isotope, are useful in drug and/or substrate tissue distribution studies. The radioactive isotopes tritium, i.e. $^3H$, and carbon-14, i.e., $^{14}C$, are particularly useful for this purpose in view of their ease of incorporation and ready means of detection. For example, a compound of formula I can be enriched with 1, 2, 5, 10, 25, 50, 75, 90, 95, or 99 percent of a given isotope.

Substitution with heavier isotopes such as deuterium, i.e. $^2H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula I can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula I and a pharmaceutically acceptable carrier, diluent and/or excipient.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include replacement of the hydrogen atom of the proline (N—H) with a prodrug moiety. The prodrug moiety may include phosphates, phosphate esters, alkyl phosphates, alkyl phosphate esters, acyl ethers, or other prodrug moieties as discussed below. In some embodiments, the prodrug moiety is:

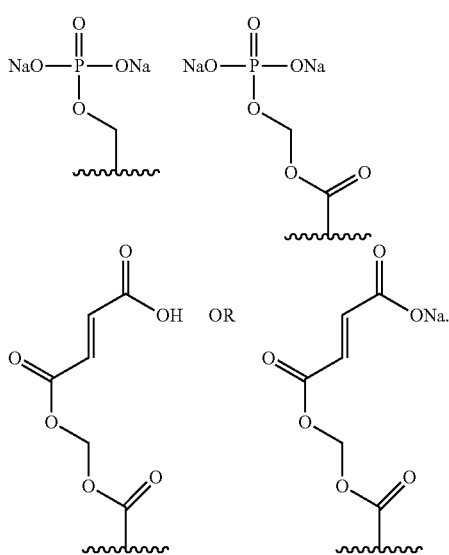

Additional types of prodrugs are also encompassed. For example, where an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methylalanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxyl groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6}$)alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier. The compositions of the invention can be used to selectively inhibit TRPA1 in patients (e.g., humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions or medicaments comprising a compound of formula I or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21st Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA1 activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered as a medical therapy to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. Exp. Mol. Pathol. 2006, 81(2), 166-170), fibromyalgia, migraine and headache (e.g. cluster headache, sinus headache, or tension headache; see, Goadsby Curr. Pain Headache Reports 2004, 8, 393), sinusitis, oral mucositis, toothache, dental trauma, dental extractions, dental infections, burn (Bolcskei et al., Pain 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, cystitis, interstitial cystitis, cholecystitis, urinary tract infection, urethral colic, renal colic, pharyngitis, cold sores, stomatitis, external otitis, otitis media (Chan et al., Lancet, 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., J Pharmacal Exp Ther., 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. J. Pharmacal. Exp. Ther. 2003, 306, 387; Walker, K. M. et al., J. Pharmacal. Exp. Ther. 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., Neurosci. Lett. 2005, 393 (1), 70-73; Asai, H. et al., Pain 2005, 117, 19-29), or bone destruction pain (see, Ghilardi, J. R. et al., J. Neurosci. 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered as a medical therapy to treat itch, which may arise from various sources, such as dermatological or inflammatory disorders.

In another specific embodiment, compounds of the invention can be administered as a medical therapy to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (lBO), Crohn's disease, and ulcerative colitis (Geppetti, P. et al., Br. J. Pharmacal. 2004, 141, 1313-20; Yiangou, Y. et al., Lancet 2001, 357, 1338-39; Kimball, E. S. et al., Neurogastroenterol. Motif, 2004, 16, 811), osteoarthritis (Szabo, A. et al., J. Pharmacal. Exp. Ther. 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered as a medical therapy to treat inner ear disorders. Such disorders include, for example, hyperacusis, tinnitus, vestibular hypersensitivity, and episodic vertigo.

For example, compounds of the invention can be administered as a medical therapy to treat tracheobronchial and diaphragmatic dysfunctions including, for example, asthma and allergy-related immune responses (Agopyan, N. et al., Am. J. Physiol. Lung Cell Mol. Physiol. 2004, 286, L563-72; Agopyan, N. et al., Toxicol. Appl. Pharmacal. 2003, 192, 21-35), cough (e.g., acute or chronic cough, or cough caused by irritation from gastroesophageal reflux disease; see, Lalloo, U. G. et al., J. Appl. Physiol. 1995, 79(4), 1082-7), bronchospasm, chronic obstructive pulmonary disease, chronic bronchitis, emphysema, and hiccups (hiccoughs, singultus).

In another specific embodiment, compounds of the invention can be administered as a medical therapy to treat gastrointestinal and urinary tract disorders such as, bladder overactivity, inflammatory hyperalgesia, visceral hyperreflexia of the urinary bladder, hemorrhagic cystitis (Dinis, P. et al., J Neurosci., 2004, 24, 11253-11263), interstitial cystitis (Sculptoreanu, A. et al., Neurosci Lett., 2005, 381, 42-46), inflammatory prostate disease, prostatitis (Sanchez, M. et al., Eur J Pharmacal., 2005, 515, 20-27), nausea, vomiting, intestinal cramping, intestinal bloating, bladder spasms, urinary urgency, defecation urgency and urge incontinence.

In another specific embodiment, compounds of the invention can be administered as a medical therapy to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered as a medical therapy to treat other diseases, disorders, or conditions mediated through TRPA1 activity, such as anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered as a medical therapy to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound as described herein to a subject in need thereof.

In another embodiment, the invention provides for a compound as described herein or a pharmaceutically acceptable salt thereof for modulating TRPA1 activity.

In another embodiment, the invention provides for a compound as described herein or a pharmaceutically acceptable salt thereof for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound as described herein to a subject in need thereof.

In another embodiment, the invention provides for a compound as described herein or a pharmaceutically acceptable salt thereof for the treatment or prophylaxis of a respiratory disorder.

In another embodiment, the invention provides for the use of a compound as described herein or a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound as described herein or a pharmaceutically acceptable salt thereof to the mammal.

In another embodiment, the invention provides for a method for modulating TRPA1 activity, comprising contacting TRPA1 with a compound as described herein or a pharmaceutically acceptable salt thereof.

In another embodiment, the invention provides for a compound as described herein or a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound as described herein or a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound as described herein or a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder. In some embodiments, the disease or condition is asthma.

Combination Therapy

The compounds of the invention may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with other therapeutic agents, including, but not limited to the following.

Opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine.

Non-opiate analgesics, e.g., acetomeniphen, and salicylates (e.g., aspirin).

Nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac.

Anticonvulsants, e.g., carbamazepine, oxcarbazepine, lamotrigine, valproate, topiramate, gabapentin and pregabalin.

Antidepressants such as tricyclic antidepressants, e.g., amitriptyline, clomipramine, despramine, imipramine and nortriptyline.

COX-2 selective inhibitors, e.g., celecoxib, rofecoxib, parecoxib, valdecoxib, deracoxib, etoricoxib, and lumiracoxib.

Alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline.

Barbiturate sedatives, e.g., amobarbital, aprobarbital, butabarbital, butabital, mephobarbital, metharbital, methohexital, pentobarbital, phenobartital, secobarbital, talbutal, theamylal and thiopental.

Tachykinin (NK) antagonist, particularly an NK-3, NK-2 or NK-1 antagonist, e.g., (aR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S).

Coal-tar analgesics, e.g., paracetamol.

Serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine.

Noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics.

Dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine.

Acetylcholinesterase inhibitors, e.g., donepezil.

5-HT3 antagonists, e.g., ondansetron.

Metabotropic glutamate receptor (mGluR) antagonists.

Local anaesthetics, e.g., mexiletine and lidocaine.

Corticosteroids, e.g., dexamethasone.

Antiarrhythimics, e.g., mexiletine and phenytoin.

Muscarinic antagonists, e.g., tolterodine, propiverine, tropsium chloride, darifenacin, solifenacin, temiverine and ipratropium.

Cannabinoids.

Vanilloid receptor agonists (e.g., resinferatoxin) or antagonists (e.g., capsazepine).

Sedatives, e.g., glutethimide, meprobamate, methaqualone, and dichloralphenazone.

Anxiolytics, e.g., benzodiazepines.

Antidepressants, e.g., mirtazapine.

Topical agents, e.g., lidocaine, capsacin and resiniferotoxin.

Muscle relaxants, e.g., benzodiazepines, baclofen, carisoprodol, chlorzoxazone, cyclobenzaprine, methocarbamol and orphrenadine.

Anti-histamines or H1 antagonists.

NMDA receptor antagonists.

5-HT receptor agonists/antagonists.

PDEV inhibitors.

Tramadol®.

Cholinergic (nicotine) analgesics.

Alpha-2-delta ligands.

Prostaglandin E2 subtype antagonists.

Leukotriene B4 antagonists.

5-lipoxygenase inhibitors.

5-HT3 antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

EXAMPLES

General Preparation of Compounds of Formula I

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography. Unless otherwise noted, flash chromatography was carried out using prepacked silica gel cartridges from either ISCO or SiliCycle on an ISCO CombiFlash® chromatography instrument (from Teledyne Isco, Inc.). Reverse-phase preparative HPLC was performed using a (1) Polaris C-18 5 µM column (50×21 mm), or (2)) (Bridge Prep C-18 OBD 5 µM column (19×150 mm). Supercritical fluid chromatography was carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 µM, (2) 4.6 cm×5 cm, 5 µM, or (3) 15 cm×21.2 mm, 5 µM.

Mass spectrometry (MS) was performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

Example 1: Preparation of Intermediates

Preparation 1: (2S,4R,5S)-1-[(tert-butoxy)carbonyl]-4-fluoro-5-methylpyrrolidine-2-carboxylic Acid The overall Preparation 1 reaction scheme is as follows:

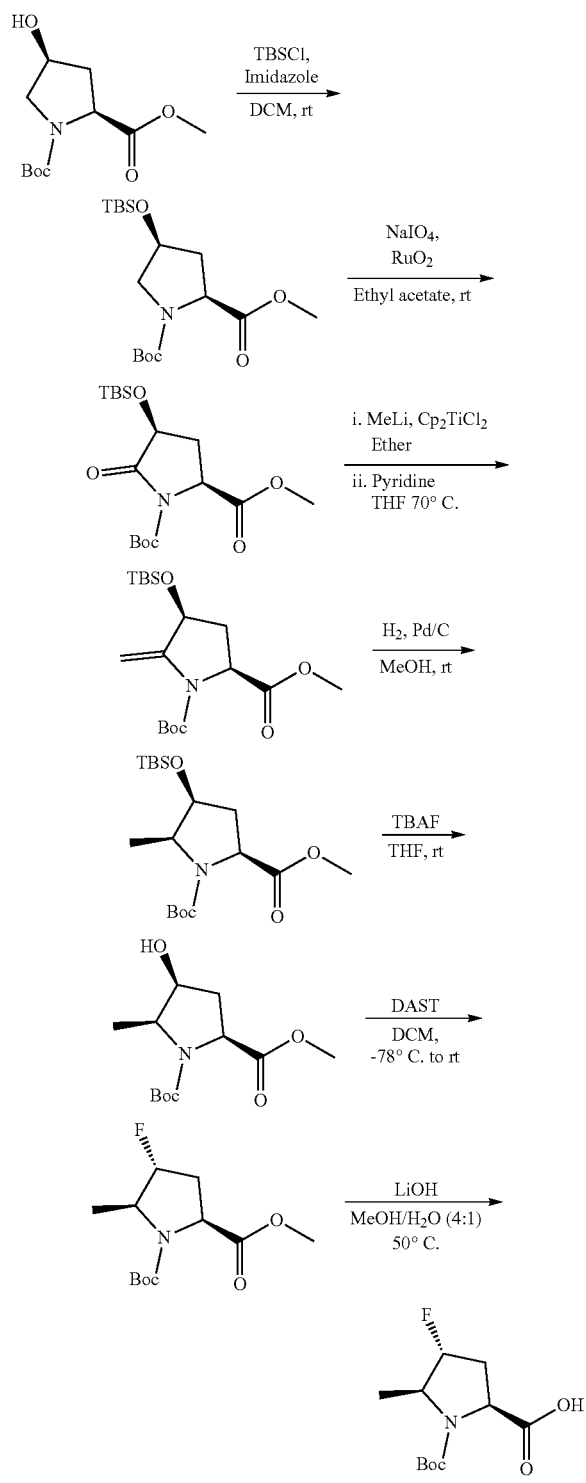

Preparation 1 Step 1: Preparation of 1-tert-butyl 2-methyl (2S,4S)-4-[(tert-butyldimethylsilyl)oxy]-5-oxopyrrolidine-1,2-dicarboxylate

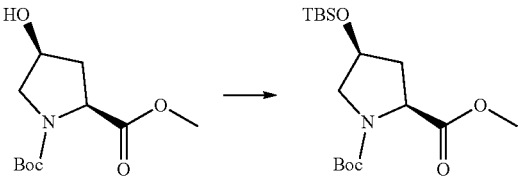 [SMILES: COC(=O)[C@@H]1C[C@H](O)CN1C(=O)OC(C)(C)C ; COC(=O)[C@@H]1C[C@H](O[Si](C)(C)C(C)(C)C)CN1C(=O)OC(C)(C)C]

TBSCl (138 g, 915.59 mmol, 1.50 equiv) in dichloromethane (500 mL) was added dropwise into a solution of 1-tert-butyl 2-methyl (2S,4S)-4-hydroxypyrrolidine-1,2-dicarboxylate (150 g, 611.57 mmol, 1.00 equiv) in dichloromethane (1500 mL) and 1H-imidazole (83 g, 1.22 mol, 2.00 equiv) at room temperature. After being stirred overnight at room temperature the resulting mixture was washed with water, dried over anhydrous sodium sulfate, and concentrated under vacuum. The residue was purified by a silica gel column eluting with ethyl acetate/petroleum ether (1:10). This resulted in the title compound (205 g, 93%) as a colorless oil. LCMS [M+H$^+$] 360; $^1$H NMR (400 MHz, CDCl$_3$) δ 4.48 (t, J=7.4 Hz, 1H), 4.30 (t, J=7.2 Hz, 1H), 3.79 (s, 3H), 2.62-2.55 (m, 1H), 2.04-1.97 (m, 1H), 1.58-1.26 (m, 11H), 0.90 (s, 9H), 0.18 (s, 3H), 0.14 (s, 3H).

Preparation 1 Step 2: Preparation of 1-tert-butyl 2-methyl (2S,4S)-4-[(tert-butyldimethylsilyl)oxy]-5-oxopyrrolidine-1,2-dicarboxylate

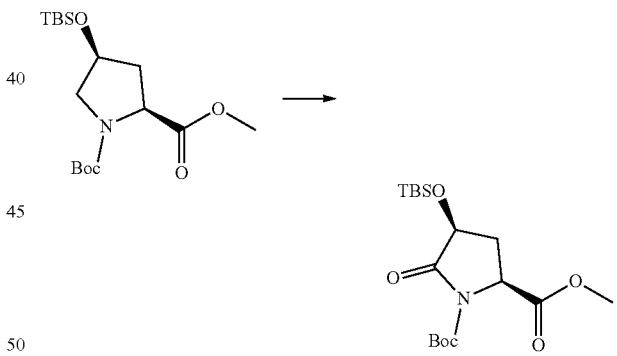

A mixture of NaIO$_4$ (279 g, 1.30 mol, 4.00 equiv), ruthenium(iv) oxide hydrate (8.7 g, 57.58 mmol, 0.20 equiv), and 1-tert-butyl 2-methyl (2S,4S)-4-[(tert-butyldimethylsilyl)oxy]pyrrolidine-1,2-dicarboxylate (117 g, 325.42 mmol, 1.00 equiv) in ethyl acetate (1.2 L)/water (1.2 L) was stirred overnight at room temperature. The mixture was separated and the organic was washed with saturated Na$_2$SO$_3$ and brine, dried over anhydrous sodium sulfate and concentrated under vacuum. The residue was purified by a silica gel column eluting with ethyl acetate/petroleum ether (1:10). This resulted in the title compound (73 g, 60%) as a colorless oil. LCMS [M+H$^+$] 374; $^1$H NMR (400 MHz, CDCl$_3$) δ 4.50-4.46 (t, J=7.4 Hz, 1H), 4.32-4.38 (t, J=7.2 Hz, 1H), 3.78 (s, 3H), 2.62-2.55 (m, 1H), 2.04-1.97 (m, 1H), 1.52 (s, 9H), 0.90 (s, 9H), 0.18 (s, 3H), 0.14 (s, 3H).

Preparation 1 Step 3: Preparation of 1-tert-butyl 2-methyl (2S,4S)-4-[(tert-butyldimethylsilyl)oxy]-5-methylidenepyrrolidine-1,2-dicarboxylate

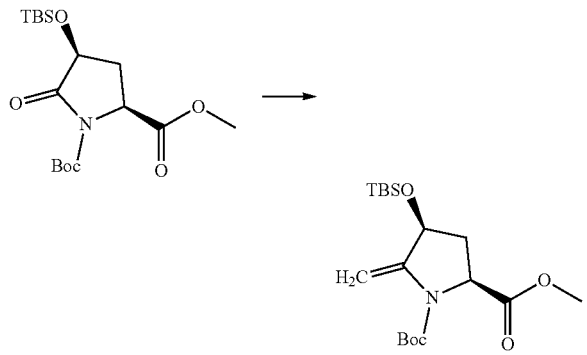

CH₃Li (510 mL, 1.6M in diethyl ether, 11.00 equiv) was added dropwise into a suspension of bis(cyclopenta-1,3-dien-1-yl)titanium dihydrochloride (100 g, 401.67 mmol, 5.00 equiv) in ether (1 L) at −50° C. under nitrogen. The resulting solution was stirred for 80 min at 0° C. and quenched by 1 L of water at −50° C. The mixture was separated and the organic solution was dried over anhydrous sodium sulfate. The resulting solution was diluted with 500 mL of toluene. Most of the diethyl ether was removed under vacuum. A solution of 1-tert-butyl 2-methyl (2S,4S)-4-[(tert-butyldimethylsilyl)oxy]-5-oxopyrrolidine-1,2-dicarboxylate (30 g, 80.32 mmol, 1.00 equiv) and pyridine (25 g, 316.06 mmol, 4.00 equiv) in tetrahydrofuran (100 ml) was added into the above solution at room temperature. After being stirred for 3 h at 70° C. the resulting solution was cooled to room temperature and diluted with 1 L of petroleum ether. The solid was filtered out and the liquid was concentrated under vacuum. The residue was purified by a silica gel column eluting with petroleum ether/ethyl acetate (20:1). This resulted in the title compound (25 g, 84%) as yellow oil; LCMS [M+H⁺] 372.

Preparation 1 Step 4: Preparation of 1-tert-butyl 2-methyl (2S,4S,5S)-4-[(tert-butyldimethylsilyl)oxy]-5-methylpyrrolidine-1,2-dicarboxylate

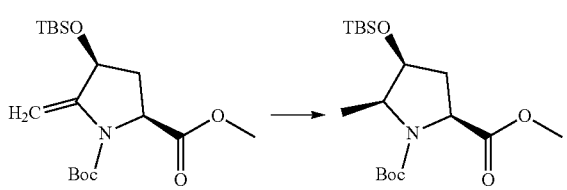

A mixture of 1-tert-butyl 2-methyl (2S,4S)-4-[(tert-butyldimethylsilyl)oxy]-5-methylidenepyrrolidine-1,2-dicarboxylate (25 g, 67.29 mmol, 1.00 equiv), methanol (800 mL) and palladium on carbon (2.5 g) was stirred for 3 h at room temperature under hydrogen. The solid was filtered out and the liquid was concentrated under vacuum. This resulted in the title compound (21 g, 84%) as colorless oil which was used for the next step without further purification. LCMS [M+H⁺] 374; ¹H NMR (300 MHz, CDCl₃) δ 4.27-4.11 (m, 2H), 3.97-3.81 (t, 1H), 3.71 (s, 3H), 2.35-2.26 (m, 1H), 2.03-1.91 (m, 1H), 1.45-1.39 (m, 9H), 1.25-1.15 (m, 3H), 0.87 (s, 9H), 0.04 (s, 6H).

Preparation 1 Step 5: Preparation of 1-tert-butyl 2-methyl (2S,4S,5S)-4-hydroxy-5-methylpyrrolidine-1,2-dicarboxylate

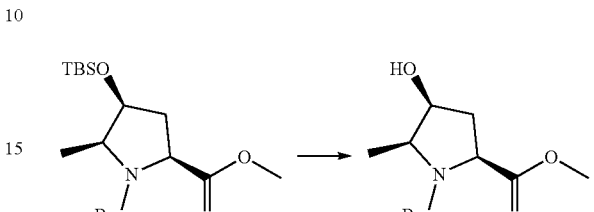

A mixture of 1-tert-butyl 2-methyl (2S,4S,5S)-4-[(tert-butyldimethylsilyl)oxy]-5-methylpyrrolidine-1,2-dicarboxylate (21 g, 56.22 mmol, 1.00 equiv) and TBAF (67 mL, 1M in THF, 1.20 equiv) in tetrahydrofuran (210 mL) was stirred for 2 h at room temperature. The resulting solution was diluted with ethyl acetate, washed with brine/aqueous HCl (0.1%)/water, dried over anhydrous sodium sulfate, and concentrated under vacuum. The residue was purified by a silica gel column eluting with ethyl acetate/petroleum ether (1/10). This resulted in the title compound (14 g, 96%) as colorless oil. LCMS [M+H⁺] 260.

Preparation 1 Step 6: Preparation of 1-tert-butyl 2-methyl (2S,4R,5S)-4-fluoro-5-methylpyrrolidine-1,2-dicarboxylate

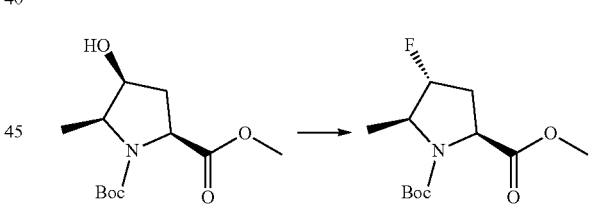

DAST (41 g, 254.36 mmol, 6.00 equiv) was added dropwise into a solution of 1-tert-butyl 2-methyl (2S,4S,5S)-4-hydroxy-5-methylpyrrolidine-1,2-dicarboxylate (11 g, 42.42 mmol, 1.00 equiv) in dichloromethane (250 mL) at −78° C. under nitrogen. The resulting solution was allowed to warm up to room temperature and stirred for 48 h. The mixture was quenched by saturated sodium bicarbonate at 0° C. and the pH value of the mixture was adjusted to 9. The resulting mixture was extracted with ethyl acetate, washed with brine, dried over anhydrous sodium sulfate, and concentrated under vacuum. The residue was purified by a silica gel column eluting with ethyl acetate/petroleum ether (1/10). This resulted in the title compound (4.2 g, 38%) as light yellow oil. LCMS [M+H⁺] 262; ¹H NMR (300 MHz, CDCl₃) δ 4.97-4.75 (d, J=51.6 Hz, 1H), 4.48-4.06 (m, 2H), 3.75 (s, 3H), 2.58-2.05 (m, 2H), 1.61-1.42 (m, 9H), 1.28-1.22 (m, 3H).

Preparation 1 Step 7: Preparation of (2S,4R,5S)-1-[(tert-butoxy)carbonyl]-4-fluoro-5-methylpyrrolidine-2-carboxylic Acid

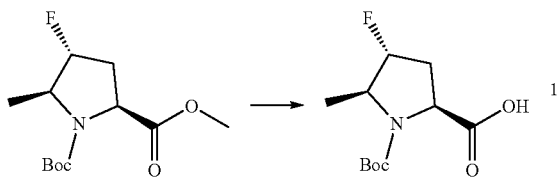

A mixture of 1-tert-butyl 2-methyl (2S,4R,5S)-4-fluoro-5-methylpyrrolidine-1,2-dicarboxylate (2.4 g, 9.19 mmol, 1.00 equiv) and LiOH (441 mg, 18.42 mmol, 2.01 equiv) in methanol (100 mL)/water (25 mL) was stirred for 12 h at 50° C. The resulting mixture was concentrated under vacuum and the mixture was dissolved in water. The pH value of the aqueous solution was adjusted to 3-5 with hydrogen chloride (1N). The resulting solution was extracted with ethyl acetate, dried over anhydrous sodium sulfate, and concentrated under vacuum. This resulted in the title compound (2 g) as a light yellow solid which was used for the next step without further purification. LCMS [M+H$^+$] 148; $^1$H NMR (400 MHz, CD$_3$OD) δ 5.00-4.86 (d, J=51.6 Hz, 1H), 4.36-4.29 (m, 1H), 4.14-4.07 (m, 1H), 2.61-2.51 (m, 1H), 2.32-2.17 (m, 1H), 1.51-1.46 (m, 9H), 1.24-1.22 (d, J=7.2 Hz, 3H).

Preparation 2: (2S,4R,5S)-4-fluoro-1-(4-fluorophenylsulfonyl)-5-methyl-N-((5-(trifluoromethyl)-2-(2-(trifluoromethyl)pyrimidin-5-yl)pyridin-4-yl)methyl)pyrrolidine-2-carboxamide The overall Preparation 2 reaction scheme is as follows:

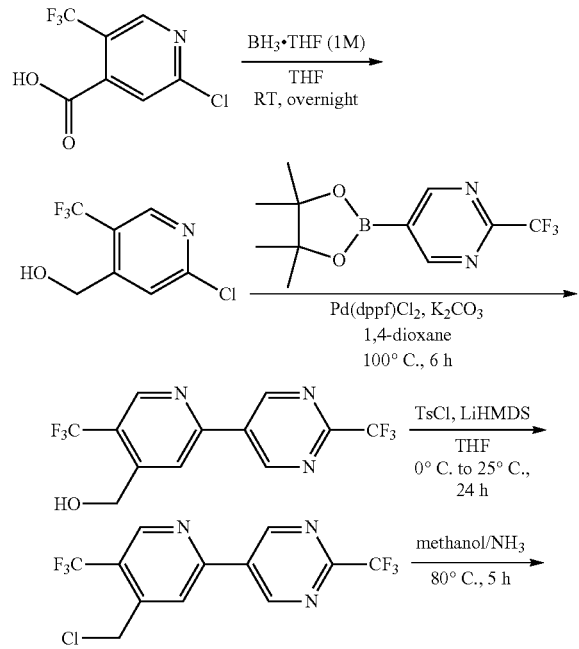

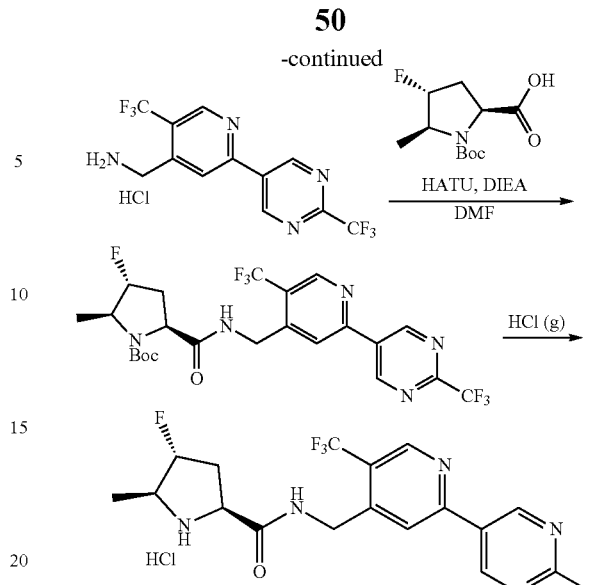

Preparation 2 Step 1: Preparation of (2-chloro-5-(trifluoromethyl)pyridin-4-yl)methanol

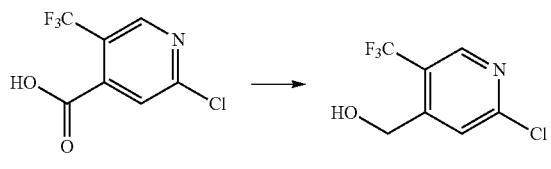 [SMILES: O=C(O)c1cc(Cl)ncc1C(F)(F)F ; OCc1cc(Cl)ncc1C(F)(F)F]

Into a 250-mL 3-necked round-bottom flask purged and maintained with an inert atmosphere of nitrogen was placed a solution of 2-chloro-5-(trifluoromethyl) pyridine-4-carboxylic acid (4.5 g, 19.95 mmol, 1.00 equiv) in tetrahydrofuran (40 mL) followed by the addition of BH$_3$.THF (1 M) (40 mL, 2.00 equiv) dropwise with stirring at 0° C. over 10 min. The resulting solution was stirred at room temperature overnight, quenched by the addition of 10 mL of methanol at 0° C., concentrated under vacuum, and extracted with ethyl acetate. The combined organic layers were washed with brine, dried over sodium sulfate, and concentrated under vacuum. The residue was purified by a silica gel column eluted with ethyl acetate/petroleum ether (1:10) to afford 3 g (crude) of [2-chloro-5-(trifluoromethyl)pyridin-4-yl]methanol as a white solid.

Preparation 2 Step 2: Preparation of (5-(trifluoromethyl)-2-(2-(trifluoromethyl)pyrimidin-5-yl)pyridin-4-yl)methanol

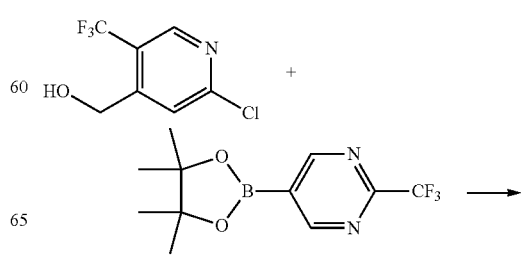

-continued

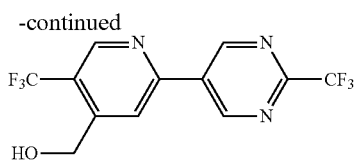

Into a 3-L 3-necked round-bottom flask purged and maintained with an inert atmosphere of nitrogen was placed [2-chloro-5-(trifluoromethyl)pyridin-4-yl]methanol (75.6 g, 357.33 mmol, 1.00 equiv), 1,4-dioxane (1.5 L), 5-(tetramethyl-1,3,2-dioxaborolan-2-yl)-2-(trifluoromethyl)pyrimidine (110 g, 401.39 mmol, 1.20 equiv), $K_2CO_3$ (148 g, 1.06 mol, 3.00 equiv), and $Pd(dppf)Cl_2$ (13 g, 17.77 mmol, 0.05 equiv). The resulting solution was stirred at 100° C. for 6 h under a nitrogen atmosphere, cooled to room temperature, and filtered. The filter cake was washed with 2×300 mL of EA. The filtrate was concentrated under vacuum. The residue was applied onto a silica gel column eluted with ethyl acetate/petroleum ether (1/5-1/2) to afford 90 g (78%) of [5-(trifluoromethyl)-2-[2-(trifluoromethyl)pyrimidin-5-yl]pyridin-4-yl]methanol as a white solid.

Preparation 2 Step 3: Preparation of 5-[4-(chloromethyl)-5-(trifluoromethyl)pyridin-2-yl]-2-(trifluoromethyl)pyrimidine

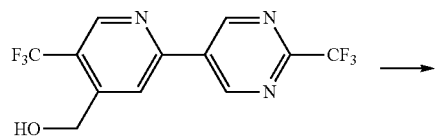

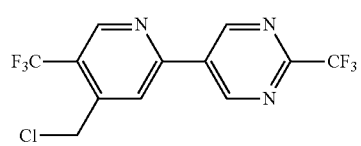

Into a 2-L 3-necked round-bottom flask purged and maintained with an inert atmosphere of nitrogen was placed a solution of [5-(trifluoromethyl)-2-[2-(trifluoromethyl)pyrimidin-5-yl]pyridin-4-yl]methanol (80 g, 247.53 mmol, 1.00 equiv) in tetrahydrofuran (800 mL) followed by the addition of LiHMDS (1 mol/L) (322 mL, 1.30 equiv) dropwise with stirring at 0° C. The mixture was stirred at 0° C. for 1 h. To this mixture was added 4-methylbenzene-1-sulfonyl chloride (61.2 g, 321.01 mmol, 1.30 equiv) in portions at 0° C. under a nitrogen atmosphere. The resulting solution was stirred from 0° C. to 25° C. for 24 h, cooled to 0° C., quenched by the addition of 100 mL of water, and extracted with 3×500 mL of ethyl acetate. The combined organic layers were dried over anhydrous sodium sulfate and concentrated under reduced pressure. The residue was purified by silica gel column chromatography eluted with ethyl acetate/petroleum ether (1/10) to afford 30 g (35%) of 5-[4-(chloromethyl)-5-(trifluoromethyl)pyridin-2-yl]-2-(trifluoromethyl)pyrimidine as a light yellow solid.

Preparation 2 Step 4: Preparation of [5-(trifluoromethyl)-2-[2-(trifluoromethyl)pyrimidin-5-yl]pyridin-4-yl]methanamine hydrochloride

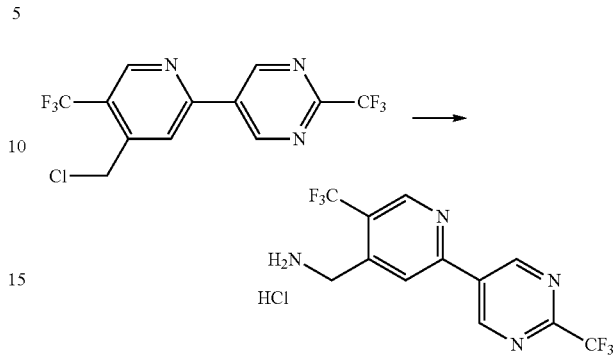

Into a 200-mL sealed tube was placed a solution of 5-[4-(chloromethyl)-5-(trifluoromethyl)pyridin-2-yl]-2-(trifluoromethyl)pyrimidine (20 g, 58.54 mmol, 1.00 equiv) in methanol/$NH_3$ (140 mL). The resulting solution was stirred at 80° C. in an oil bath for 5 h. This reaction was repeated for 2 times. The reaction mixture was cooled to room temperature and concentrated under vacuum. The pH value of the aqueous solution was adjusted to 8 with saturated aqueous sodium bicarbonate. The resulting solution was extracted with 3×300 mL of dichloromethane. The combined organic layers were dried over anhydrous sodium sulfate and concentrated under vacuum. The residue was applied onto a silica gel column eluted with 10% to 30% ethyl acetate in petroleum ether to afford 5-(trifluoromethyl)-2-[2-(trifluoromethyl)pyrimidin-5-yl]pyridin-4-yl]methanamine 33 g as a light yellow solid. The residue was dissolved in 800 mL of ethyl acetate. The product was precipitated by the addition of ethyl acetate/HCl (g). The resulting mixture was concentrated under vacuum. The solids were collected by filtration. The filter cake was washed with 3×2500 mL of ether and dried to afford 31 g (49.5%) of [5-(trifluoromethyl)-2-[2-(trifluoromethyl)pyrimidin-5-yl]pyridin-4-yl]methanamine hydrochloride as a white solid. LCMS [M+H$^+$] 323.

Preparation 2 Step 5: Preparation of (2S,3R,5S)-tert-butyl 3-fluoro-2-methyl-5-((5-(trifluoromethyl)-2-(2-(trifluoromethyl)pyrimidin-5-yl)pyridin-4-yl)methylcarbamoyl)pyrrolidine-1-carboxylate

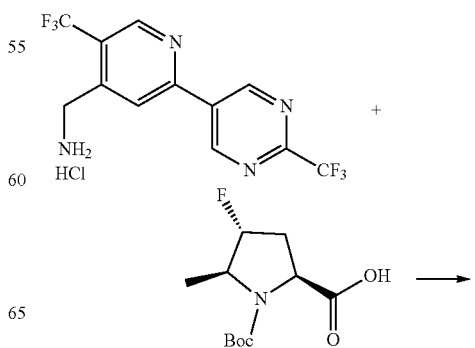

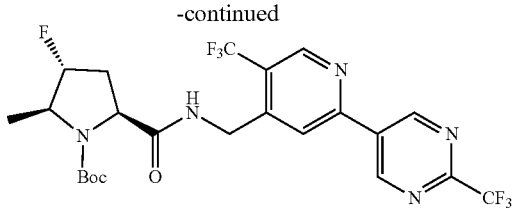

A mixture of (2S,4R,5S)-1-[(tert-butoxy)carbonyl]-4-fluoro-5-methylpyrrolidine-2-carboxylic acid (14 g, 56.62 mmol, 1.00 equiv), HATU (32 g, 84.16 mmol, 1.51 equiv), DIEA (22 g, 170.22 mmol, 3.05 equiv), and [5-(trifluoromethyl)-2-[2-(trifluoromethyl)pyrimidin-5-yl]pyridin-4-yl]methanamine hydrochloride (20 g, 55.76 mmol, 1.00 equiv) in DMF (150 mL) was stirred for 2 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1/1) to afford the title compound (28 g, 91%) as a white solid. LCMS [M+H$^+$] 552.

Preparation 2 Step 6: Preparation of (2S,4R,5S)-4-fluoro-5-methyl-N-((5-(trifluoromethyl)-2-(2-(trifluoromethyl)pyrimidin-5-yl)pyridin-4-yl)methyl)pyrrolidine-2-carboxamide Hydrochloride

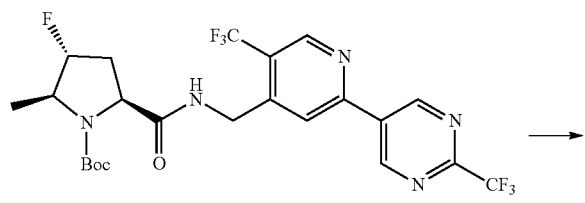

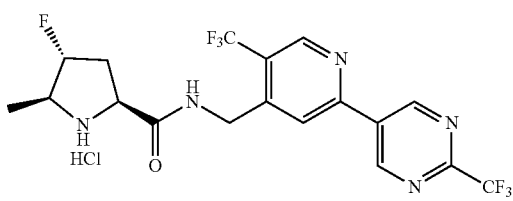

A mixture of tert-butyl (2S,3R,5S)-3-fluoro-2-methyl-5-([[5-(trifluoromethyl)-2-[2-(trifluoromethyl)pyrimidin-5-yl]pyridin-4-yl]methyl]carbamoyl)pyrrolidine-1-carboxylate (28 g, 50.77 mmol, 1.00 equiv) and saturated HCl (g) in 1,4-dioxane (200 mL) was stirred for 12 h at room temperature. The resulting mixture was concentrated under vacuum to afford the title compound (22 g, 89%) as a white solid. LCMS [M+H$^+$] 452.

Example 2

Preparation of (2S,4R,5S)-4-fluoro-1-[(5-fluoro-2-pyridyl)sulfonyl]-5-methyl-N-[[5-(trifluoromethyl)-2-[2-(trifluoromethyl)pyrimidin-5-yl]-4-pyridyl]methyl]pyrrolidine-2-carboxamide The overall reaction scheme is as follows:

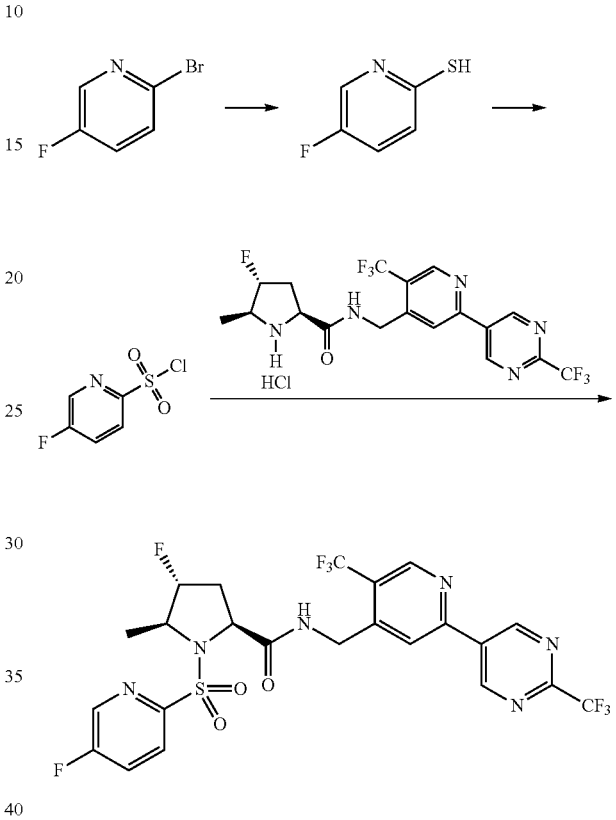

Step 1: Preparation of 5-fluoropyridine-2-thiol

A solution of 2-bromo-5-fluoropyridine (20 g, 113.65 mmol) in 20 mL of toluene was added dropwise into a solution of n-BuLi (50 mL, 2.5M in hexane, 125 mmol) in toluene (300 mL) at −78° C. under nitrogen. The reaction was stirred for 1 h at −78° C. To this was added sublimed sulfur (3.64 g, 113.52 mmol). The resulting mixture was stirred for 30 min at −78° C., then warmed up to room temperature naturally and stirred for additional 1 h at room temperature. The reaction was then quenched by the addition of water. The pH value of the solution was adjusted to 3-5 with aqueous HCl (1 mol/L). The resulting mixture was extracted with dichloromethane, washed with brine, dried over anhydrous sodium sulfate and concentrated under vacuum. This resulted in the title compound (11 g, 75%) as a yellow solid. LCMS [M+H$^+$] 533.

Step 2: Preparation of 5-fluoropyridine-2-sulfonyl Chloride

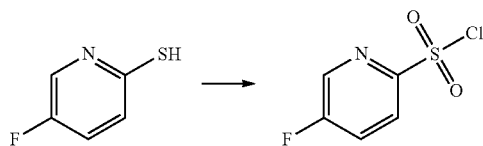 [SMILES: Fc1ccc(S)nc1 ; O=S(=O)(Cl)c1ccc(F)cn1]

Concentrated aqueous HCl (30 mL) was added into a mixture of 5-fluoropyridine-2-thiol (4.5 g, 34.84 mmol), dichloromethane (100 mL), and water (50 mL) dropwise with stirring at 0° C. To this was added sodium hypochlorite (60 mL, 14.5% available chlorine) dropwise with stirring at 0° C. The resulting mixture was stirred for 30 min at 0° C. The mixture was separated and the organic solution was washed with cold 5% $Na_2S_2O_3$ and cold brine, and then dried over anhydrous sodium sulfate. This resulted in the cold solution of the title compound in dichloromethane, which was used for the next step without any further purification.

Step 3: Preparation of (2S,4R,5S)-4-fluoro-1-[(5-fluoro-2-pyridyl)sulfonyl]-5-methyl-N-[[5-(trifluoromethyl)-2-[2-(trifluoromethyl)pyrimidin-5-yl]-4-pyridyl]methyl]pyrrolidine-2-carboxamide

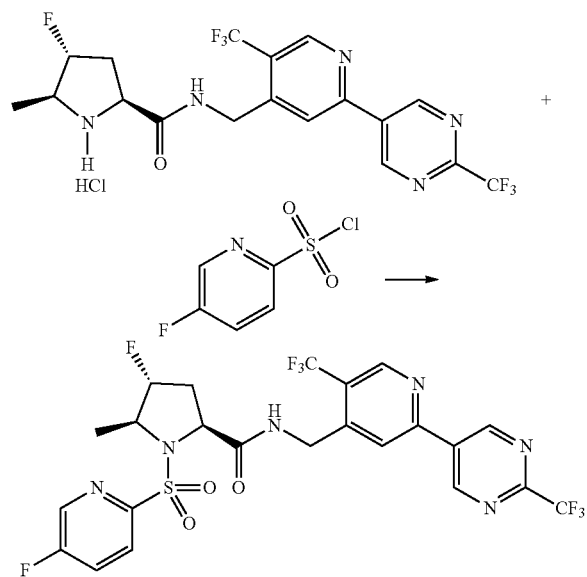

The cold solution of crude 5-fluoropyridine-2-sulfonyl chloride in dichloromethane (~0.3 M, 100 mL from Step 2) was added dropwise into a solution of (2S,4R,5S)-4-fluoro-5-methyl-N-[5-(trifluoromethyl)-2-[2-(trifluoromethyl)pyrimidin-5-yl]pyridin-4-yl]methylpyrrolidine-2-carboxamide (1.5 g, 3.32 mmol), TEA (931 mg, 9.20 mmol) and dichloromethane (100 mL). The resulting solution was stirred for 30 min at room temperature, diluted with water, extracted with ethyl acetate, washed with brine, dried over anhydrous sodium sulfate and concentrated under vacuum. The residue was purified by a silica gel column eluting with ethyl acetate/petroleum ether (1/1) to afford the title compound (2.3145 g, 15.9%) as a light yellow solid. LCMS [M+H⁺] 591. ¹H NMR (300 MHz, CDCl₃) δ 9.68 (s, 2H), 9.00 (s, 1H), 8.58 (s, 1H), 8.35 (s, 1H), 8.12-8.07 (m, 1H), 7.69-7.63 (m, 1H), 7.53-7.49 (m, 1H), 5.22-4.99 (m, 2H), 4.71-4.56 (m, 2H), 4.26-4.17 (m, 1H), 2.68-2.57 (m, 1H), 2.49-2.27 (m, 1H), 1.34 (d, J=7.0 Hz, 3H).

Example 3

Preparation of (2S,4R,5S)-4-fluoro-5-methyl-1-(3-pyridylsulfonyl)-N-[[5-(trifluoromethyl)-2-[2-(trifluoromethyl)pyrimidin-5-yl]-4-pyridyl]methyl]pyrrolidine-2-carboxamide The overall reaction scheme is as follows:

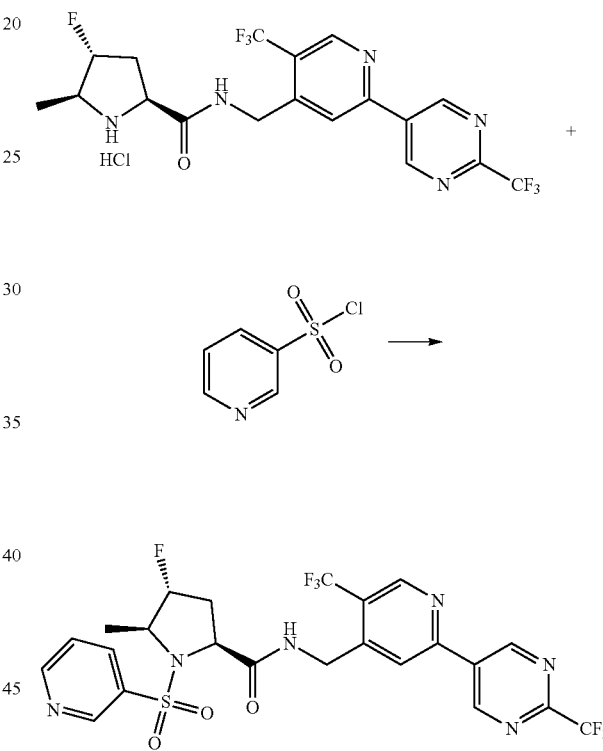

A mixture of (2S,4R,5S)-4-fluoro-5-methyl-N-[[5-(trifluoromethyl)-2-[2-(trifluoromethyl)pyrimidin-5-yl]pyridin-4-yl]methyl]pyrrolidine-2-carboxamide hydrochloride (100 mg, 0.21 mmol), dichloromethane (5 mL), triethylamine (65 mg, 0.64 mmol), and pyridine-3-sulfonyl chloride (60 mg, 0.34 mmol) was stirred for 1 h at room temperature. The resulting mixture was diluted with water, extracted with ethyl acetate, washed with brine, dried over anhydrous sodium sulfate, and concentrated under vacuum. The residue was purified by a silica gel column eluting with ethyl acetate/petroleum ether (3:1) to afford the title compound (45.1 mg, 37%) as a white solid. LCMS [M+H⁺] 593. ¹H NMR (400 MHz, CDCl₃) δ 9.71 (s, 2H), 9.38 (s, 1H), 9.02 (s, 1H), 8.95 (d, J=5.0 Hz, 1H), 8.38 (s, 1H), 8.32 (d, J=8.2 Hz, 1H), 7.68 (t, J=6.6 Hz, 2H), 5.08 (d, J=18.5 Hz, 1H), 4.84-4.64 (m, 2H), 4.44 (t, J=8.9 Hz, 1H), 4.14 (dt, J=21.0, 7.2 Hz, 1H), 2.63-2.53 (m, 1H), 2.35 (dt, J=43.2, 11.7 Hz, 1H), 1.42 (s, 3H).

Example 4

Preparation of (2S,4R,5S)-1-[(5-chloro-3-pyridyl)sulfonyl]-4-fluoro-5-methyl-N-[[5-(trifluoromethyl)-2-[2-(trifluoromethyl)pyrimidin-5-yl]-4-pyridyl]methyl]pyrrolidine-2-carboxamide The overall reaction scheme is as follows:

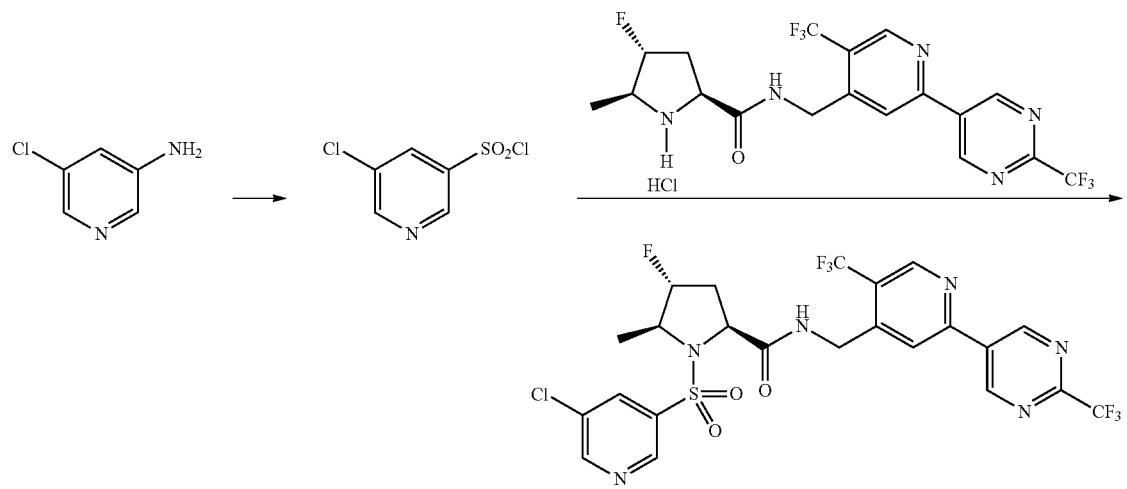

Step 1: Preparation of 5-chloropyridine-3-sulfonyl Chloride

Step 2: Preparation of (2S,4R,5S)-1-[(5-chloro-3-pyridyl)sulfonyl]-4-fluoro-5-methyl-N-[[5-(trifluoromethyl)-2-[2-(trifluoromethyl)pyrimidin-5-yl]-4-pyridyl]methyl]pyrrolidine-2-carboxamide

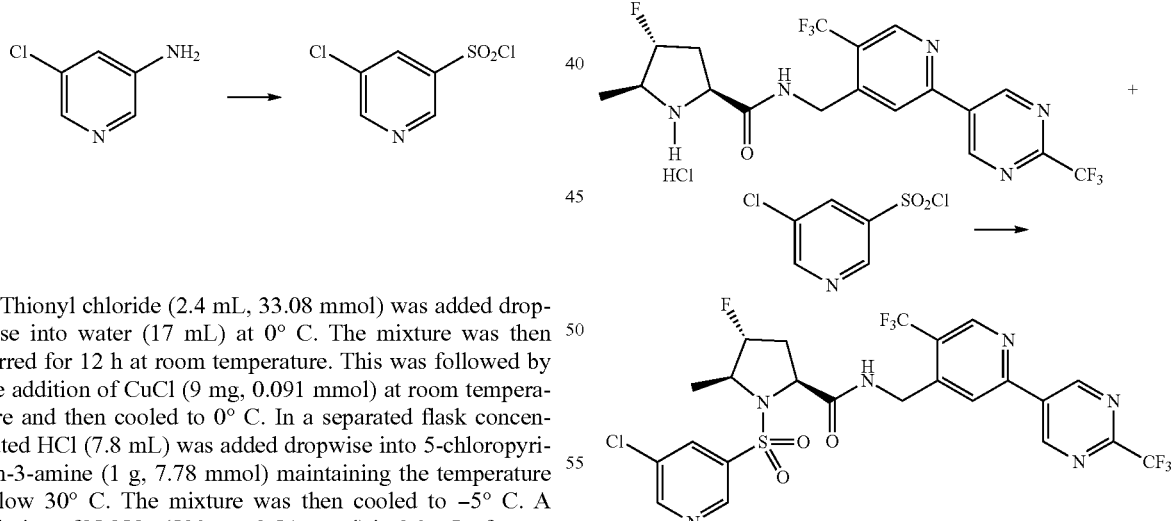

Thionyl chloride (2.4 mL, 33.08 mmol) was added dropwise into water (17 mL) at 0° C. The mixture was then stirred for 12 h at room temperature. This was followed by the addition of CuCl (9 mg, 0.091 mmol) at room temperature and then cooled to 0° C. In a separated flask concentrated HCl (7.8 mL) was added dropwise into 5-chloropyridin-3-amine (1 g, 7.78 mmol) maintaining the temperature below 30° C. The mixture was then cooled to −5° C. A solution of $NaNO_2$ (589 mg, 8.54 mmol) in 2.3 mL of water was added dropwise into the reaction mixture at −5° C. to 0° C. The reaction was then stirred for 10 min at −2° C. The mixture was added to the CuCl mixture dropwise with stirring at −5° C. The resulting mixture was stirred for 75 min at −5 to 0° C. The precipitation was collected by filtration, washed with water and dried under vacuum. This resulted in the title compound (870 mg, 53%) as a gray solid, which was used for the next step without any further purification.

A mixture of (2S,4R,5S)-4-fluoro-5-methyl-N-[5-(trifluoromethyl)-2-[2-(trifluoromethyl)pyrimidin-5-yl]pyridin-4-yl]methylpyrrolidine-2-carboxamide hydrochloride (100 mg, 0.22 mmol), dichloromethane (10 mL), TEA (62 mg, 0.61 mmol), and 5-chloropyridine-3-sulfonyl chloride (87 mg, 0.41 mmol) was stirred for 2 h at room temperature. The resulting solution was diluted with water, extracted with dichloromethane, washed with brine, dried over anhydrous sodium sulfate and concentrated under vacuum. The residue was purified by a silica gel column eluting with ethyl acetate/petroleum ether (4:1) to afford the title compound (62.2 mg, 24%) as a white solid. LCMS [M+H⁺] 627. $^1$H NMR (400 MHz, CDCl$_3$) δ 9.72 (s, 2H), 9.05 (s, 1H), 9.01-8.95 (m, 1H), 8.86 (s, 1H), 8.32 (s, 1H), 8.17 (m, 1H), 7.35-7.29 (m, 1H), 5.20-5.14 (m, 1H), 4.88-4.74 (m, 1H), 4.67-4.61 (m, 1H), 4.38-4.34 (m, 1H), 4.38-4.11 (m, 1H), 2.69-2.63 (m, 1H), 2.45-2.30 (m, 1H), 1.42 (d, J=7.1 Hz, 3H).

Example 5

Preparation of (2S,4R,5S)-1-(4-chlorofuro[3,2-c]pyridin-2-yl)sulfonyl-4-fluoro-5-methyl-N-[[5-(trifluoromethyl)-2-[2-(trifluoromethyl)pyrimidin-5-yl]-4-pyridyl]methyl]pyrrolidine-2-carboxamide The overall reaction scheme is as follows:

n-BuLi (6 mL, 63.70 mmol) was added dropwise with stirring at −40° C. into a solution of 4-chlorofuro[3,2-c]pyridine (2 g, 13.02 mmol) in tetrahydrofuran (50 mL) under nitrogen. The resulting solution was stirred for 1 h at −40° C. To the above mixture sulfur dioxide (gas) was introduced in for 30 min. The resulting solution was stirred for 1.5 h at room temperature. The product was precipitated by the addition of hexane. The solids were collected by filtration and then dissolved with DCM (80 mL). To the above solution was added NCS (2.1 g, 15.73 mmol). The resulting solution was stirred for 2 h at room temperature. The mixture was washed with water, dried over anhydrous sodium sulfate and concentrated under vacuum to afford the title compound (2.3 g, 70%) as a yellow solid which was used for the next step without any further purification.

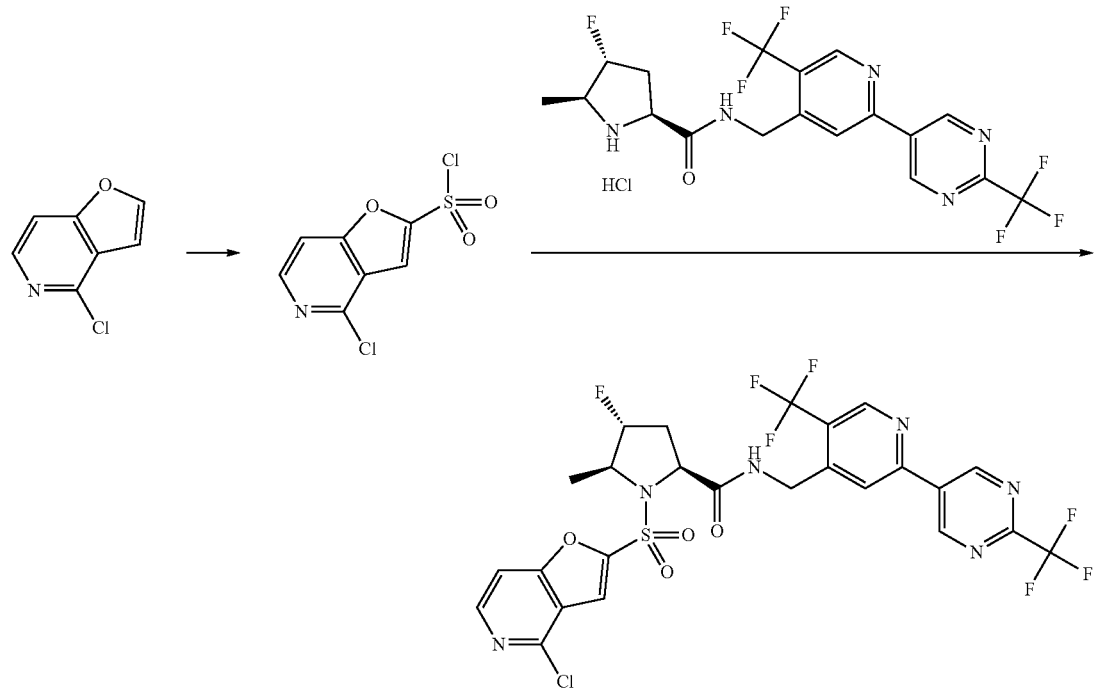

Step 1: Preparation of 4-chlorofuro[3,2-c]pyridine-2-sulfonyl Chloride

Step 2: Preparation of (2S,4R,5S)-1-(4-chlorofuro[3,2-c]pyridin-2-yl)sulfonyl-4-fluoro-5-methyl-N-[[5-(trifluoromethyl)-2-[2-(trifluoromethyl)pyrimidin-5-yl]-4-pyridyl]methyl]pyrrolidine-2-carboxamide

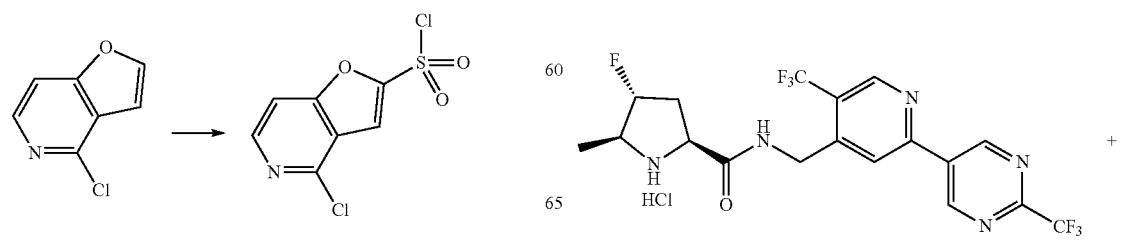

-continued

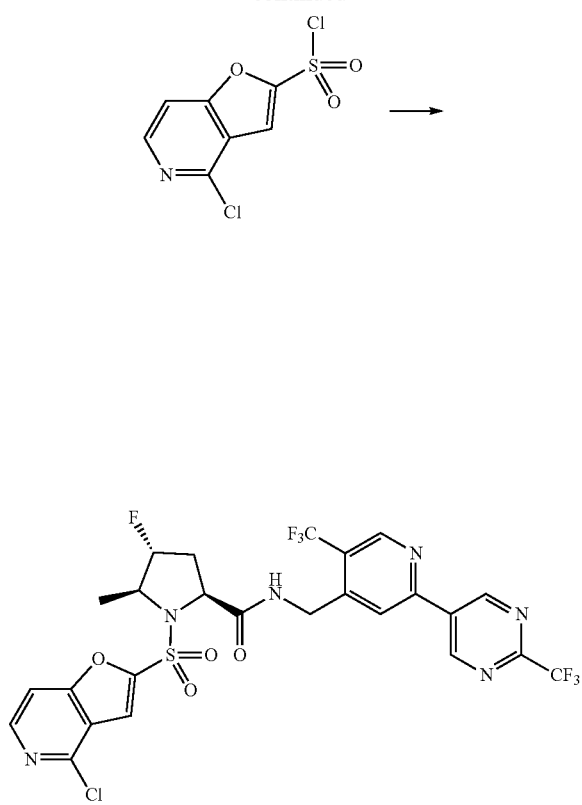

A mixture of (2S,4R,5S)-4-fluoro-5-methyl-N-[[5-(trifluoromethyl)-2-[2-(trifluoromethyl)pyrimidin-5-yl]pyridin-4-yl]methyl]pyrrolidine-2-carboxamide (100.00 mg, 0.22 mmol), dichloromethane (1.41 mL), TEA (67.26 mg, 0.67 mmol), and 4-chlorofuro[3,2-c]pyridine-2-sulfonyl chloride (55.85 mg, 0.22 mmol) was stirred for 1 h at room temperature. The resulting solution was diluted with water, extracted with dichloromethane, washed with brine, dried over anhydrous sodium sulfate and concentrated under vacuum. The residue was purified by a silica gel column eluting with ethyl acetate/petroleum ether (1:3) to afford the title compound (100 mg, 68%) as a white solid. LCMS [M+H$^+$] 667. $^1$H NMR (300 MHz, CDCl$_3$) δ 9.66 (s, 2H), 9.02 (s, 1H), 8.48 (d, J=5.9 Hz, 1H), 8.25 (s, 1H), 7.62 (d, J=0.9 Hz, 1H), 7.51 (dd, J=5.8, 0.9 Hz, 1H), 7.23-7.20 (m, 1H), 5.15 (dd, J=17.7, 7.6 Hz, 1H), 4.83-4.58 (m, 3H), 4.29 (dd, J=20.6, 7.0 Hz, 1H), 2.84-2.63 (m, 1H), 2.50-2.34 (m, 1H), 1.42 (d, J=7.1 Hz, 3H).

Example 6

Preparation of (2S,4R,5S)-4-fluoro-1-furo[3,2-c]pyridin-2-ylsulfonyl-5-methyl-N-[[5-(trifluoromethyl)-2-[2-(trifluoromethyl)pyrimidin-5-yl]-4-pyridyl]methyl]pyrrolidine-2-carboxamide The overall reaction scheme is as follows:

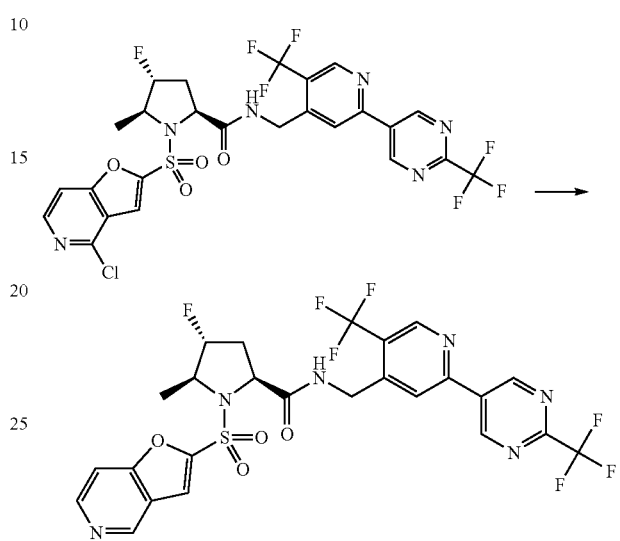

A mixture of (2S,4R,5S)-1-[4-chlorofuro[3,2-c]pyridine-2-sulfonyl]-4-fluoro-5-methyl-N-[[5-(trifluoromethyl)-2-[2-(trifluoromethyl)pyrimidin-5-yl]pyridin-4-yl]methyl]pyrrolidine-2-carboxamide (100.00 mg, 0.15 mmol), methanol (5 mL) and palladium on carbon (15.96 mg, 0.15 mmol) was stirred for 2 h at room temperature. The solids were filtered out. The solution was concentrated under vacuum. The residue was applied onto a silica gel column with DCM:MeOH (20:1) to afford the title compound 15.3 mg (16%) as a white solid. LCMS [M+H$^+$] 633. $^1$H NMR (300 MHz, CDCl$_3$) δ 9.72 (s, 2H), 9.30 (s, 1H), 8.81 (d, J=6.2 Hz, 1H), 8.32 (s, 1H), 8.08-7.72 (m, 2H), 7.51 (s, 1H), 5.22-4.62 (m, 4H), 4.35 (dd, J=20.4, 7.2 Hz, 1H), 2.81-2.22 (m, 2H), 1.47 (s, 3H).

Example 7

Preparation of (2S,4R,5S)-1-[(5-chloro-2-pyridyl)sulfonyl]-4-fluoro-5-methyl-N-[[5-(trifluoromethyl)-2-[2-(trifluoromethyl)pyrimidin-5-yl]-4-pyridyl]methyl]pyrrolidine-2-carboxamide The overall reaction scheme is as follows:

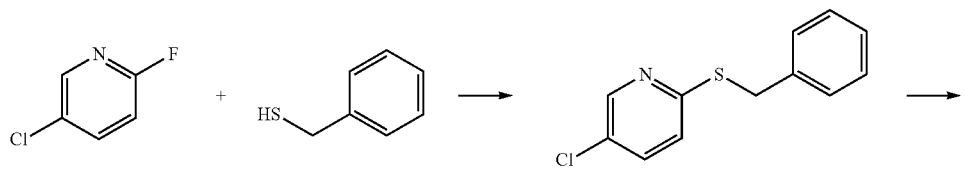

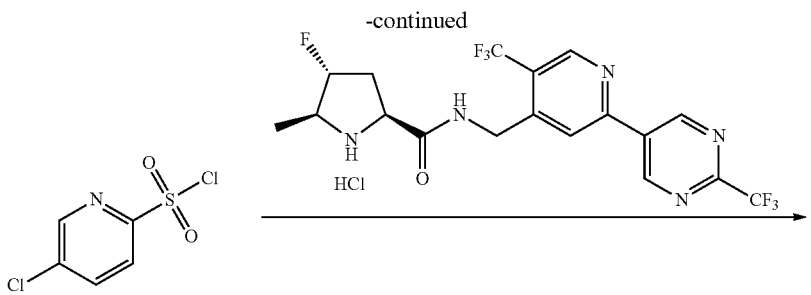

Step 1: Preparation of 2-(benzylsulfanyl)-5-chloropyridine

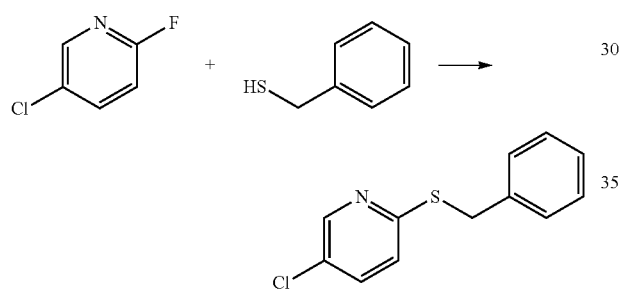

A mixture of 5-chloro-2-fluoropyridine (2 g, 15.21 mmol), N, N-dimethylformamide (40 mL), phenylmethanethiol (2 g, 16.10 mmol), and $Cs_2CO_3$ (7.52 g, 23.08 mmol) was stirred for 16 h at room temperature. The resulting solution was stirred for 6 h at 60° C. The solids were filtered out. The residue was dissolved in ethyl acetate, washed with brine, dried over anhydrous sodium sulfate, and concentrated under vacuum. The residue was purified by a silica gel column eluting with ethyl acetate/petroleum ether (1:10) to afford the title compound (3 g, 83.7%) as colorless oil. LCMS [M+H$^+$] 236.

Step 2: Preparation of 5-chloropyridine-2-sulfonyl Chloride

Concentrated aqueous HCl (6 mL) was added into a mixture of 2-(benzylsulfanyl)-5-chloropyridine (1 g, 4.24 mmol), dichloromethane (30 mL), and water (15 mL) dropwise at 0° C. To this was added sodium hypochlorite (12 mL, 14.5% available chlorine) dropwise at 0° C. The resulting mixture was stirred for 10 min at 0° C. The solution of the title compound in dichloromethane layer was rapidly separated and was used directly for the next step without any further purification.

Step 3: Preparation of (2S,4R,5S)-1-[(5-chloro-2-pyridyl)sulfonyl]-4-fluoro-5-methyl-N-[[5-(trifluoromethyl)-2-[2-(trifluoromethyl)pyrimidin-5-yl]-4-pyridyl]methyl]pyrrolidine-2-carboxamide

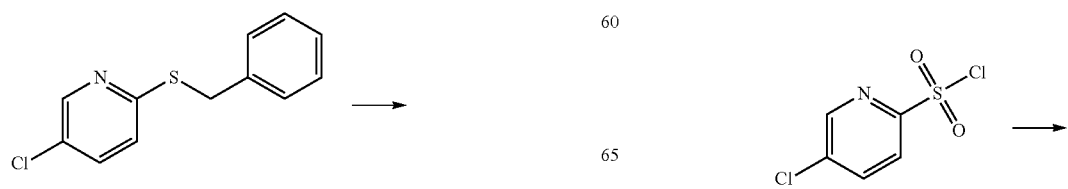

-continued

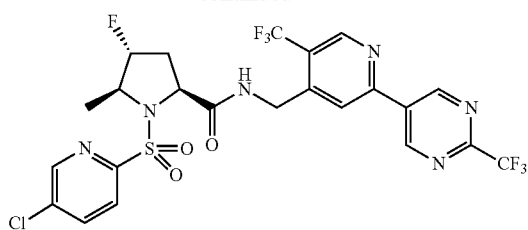

The cold solution of 5-chloropyridine-2-sulfonyl chloride in dichloromethane was added dropwise into a mixture of (2S,4R,5S)-4-fluoro-5-methyl-N-[[5-(trifluoromethyl)-2-[2-(trifluoromethyl)pyrimidin-5-yl]pyridin-4-yl]methyl]pyrrolidine-2-carboxamide (100 mg, 0.22 mmol), dichloromethane (10 mL), and TEA (66.9 mg, 0.66 mmol). The resulting solution was stirred for 5 min at 0° C. in an ice/salt bath. The reaction was then diluted with water, extracted with dichloromethane, washed with brine, dried over anhydrous sodium sulfate, and concentrated under vacuum. The residue was purified by a silica gel column eluting with ethyl acetate/hexane (1:3) to afford the title compound (32 mg, 23%) as a white solid. LCMS [M+H$^+$] 627. $^1$H NMR (400 MHz, CDCl$_3$) δ 9.69 (s, 2H), 9.01 (s, 1H), 8.69 (d, J=2.1 Hz, 1H), 8.35 (s, 1H), 7.98 (dt, J=8.4, 5.3 Hz, 2H), 7.54 (s, 1H), 5.20-5.02 (m, 2H), 4.71 (ddd, J=34.4, 22.3, 3.8 Hz, 2H), 4.31-4.11 (m, 1H), 2.78-2.56 (m, 1H), 2.55-2.28 (m, 1H), 1.35 (d, J=7.1 Hz, 3H).

Example 8

Preparation of (2S,4R,5S)-4-fluoro-1-[(3-fluoro-2-pyridyl)sulfonyl]-5-methyl-N-[[5-(trifluoromethyl)-2-[2-(trifluoromethyl)pyrimidin-5-yl]-4-pyridyl]methyl]pyrrolidine-2-carboxamide The overall reaction scheme is as follows:

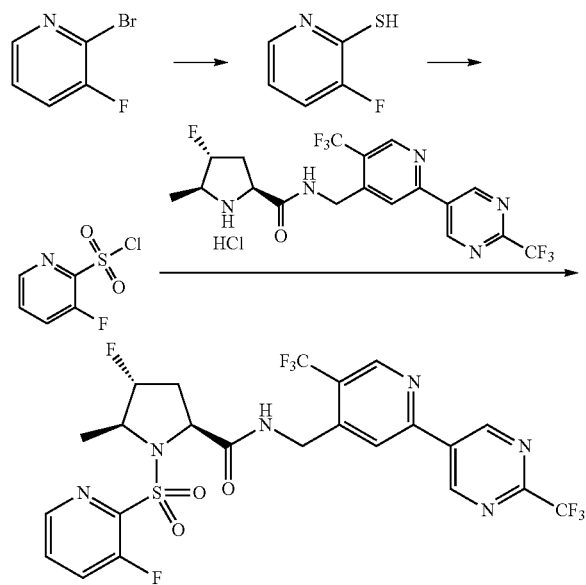

Step 1: Preparation of 3-fluoropyridine-2-thiol

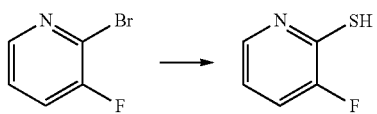 [SMILES: Fc1cccnc1Br ; Fc1cccnc1S]

A solution of 2-bromo-3-fluoropyridine (5 g, 28.41 mmol) in toluene was added into a mixture of n-BuLi (12.5 mL, 2.5M, 31.25 mmol) and toluene (80 mL) dropwise with stirring at −78° C. After being stirred over 30 min at −78° C. sulfur (910 mg, 28.38 mmol) was added to the reaction mixture. The resulting solution was stirred for 30 min at −78° C. and then 1 h at room temperature. The reaction was quenched by water and the pH value of the mixture was adjusted to 5 with 1M of aqueous HCl. The mixture was extracted with dichloromethane, washed with brine, dried over anhydrous sodium sulfate and concentrated under vacuum to afford the title compound (2.18 g, 59%) as a yellow solid.

Step 2: Preparation of 3-fluoropyridine-2-sulfonyl Chloride

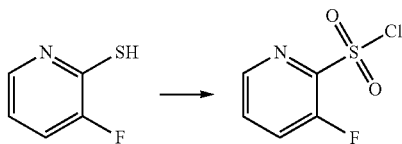 [SMILES: Fc1cccnc1S ; O=S(=O)(Cl)c1ncccc1F]

Concentrated aqueous HCl (6 mL) was added into a mixture of 3-fluoropyridine-2-thiol (1 g, 7.74 mmol), dichloromethane (30 mL), and water (15 mL) dropwise with stirring at 0° C. To this was added sodium hypochlorite (12 mL, 14.5% available chlorine) dropwise with stirring at 0° C. The resulting mixture was stirred for 10 min at 0° C. The solution of the title compound in dichloromethane layer was rapidly separated and was used directly for the next step without any further purification.

Step 3: Preparation of (2S,4R,5S)-4-fluoro-1-[(3-fluoro-2-pyridyl)sulfonyl]-5-methyl-N-[[5-(trifluoromethyl)-2-[2-(trifluoromethyl)pyrimidin-5-yl]-4-pyridyl]methyl]pyrrolidine-2-carboxamide

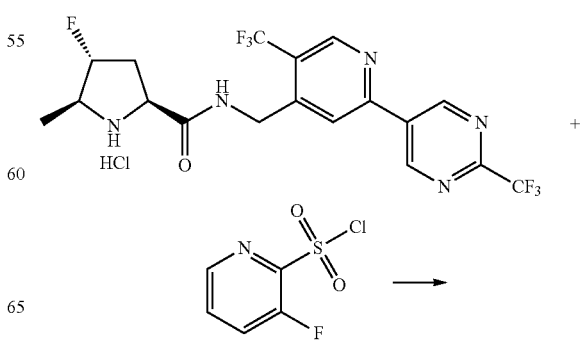

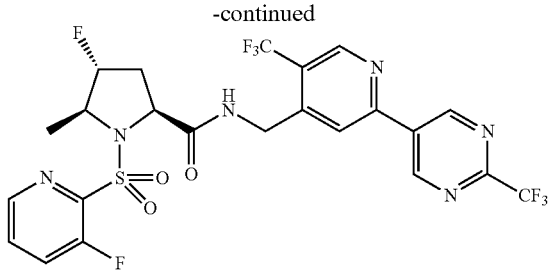

The cold solution of crude 3-fluoropyridine-2-sulfonyl chloride in dichloromethane was added dropwise into a mixture of (2S,4R,5S)-4-fluoro-5-methyl-N-[5-(trifluoromethyl)-2-[2-(trifluoromethyl)pyrimidin-5-yl]pyridin-4-yl]methylpyrrolidine-2-carboxamide hydrochloride (100 mg, 0.21 mmol), dichloromethane (10 mL), and TEA (62 mg, 0.61 mmol). The reaction was stirred for 2 h at room temperature. The resulting solution was diluted with water, extracted with dichloromethane, washed with brine, dried over anhydrous sodium sulfate and concentrated under vacuum. The residue was purified by a silica gel column eluting with ethyl acetate/petroleum ether (1/1) to afford the title compound (29.7 mg, 12%) as a white solid. LCMS [M+H$^+$] 611. $^1$H NMR (400 MHz, CDCl$_3$) δ 9.73 (s, 2H), 9.01 (s, 1H), 8.60 (dt, J=4.3, 1.5 Hz, 1H), 8.36 (s, 1H), 7.78-7.63 (m, 2H), 7.52 (s, 1H), 5.15 (dd, J=17.8, 7.7 Hz, 1H), 4.93 (t, J=8.8 Hz, 1H), 4.82 (dd, J=51.2, 3.3 Hz, 1H), 4.64 (dd, J=17.6, 4.7 Hz, 1H), 4.48-4.36 (m, 1H), 2.75-2.60 (m, 1H), 2.55-2.33 (m, 1H), 1.39 (d, J=7.0 Hz, 3H).

Example 9

Preparation of (2S,4R,5S)-1-(5-cyanopyridin-2-yl-sulfonyl)-4-fluoro-5-methyl-N-((5-(trifluoromethyl)-2-(2-(trifluoromethyl)pyrimidin-5-yl)pyridin-4-yl)methyl)pyrrolidine-2-carboxamide The overall reaction scheme is as follows:

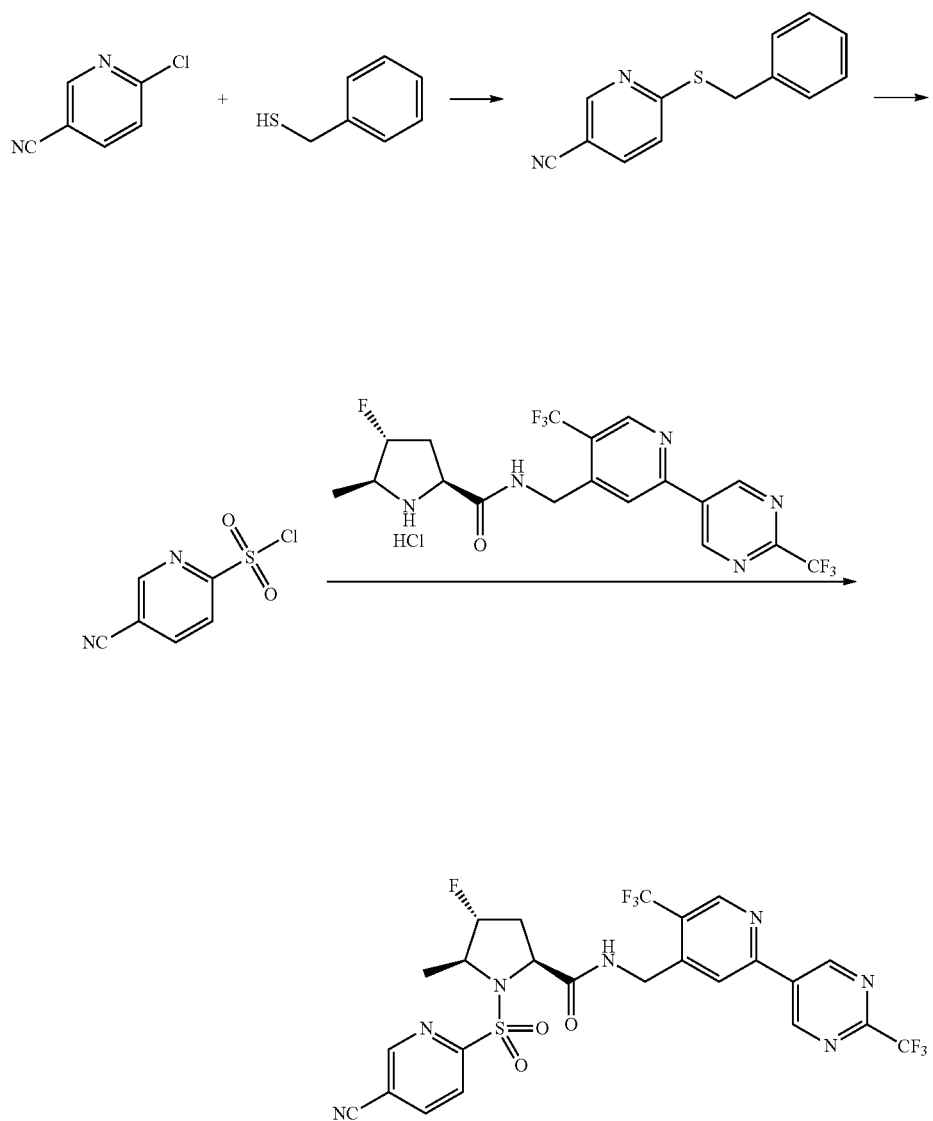

Step 1: Preparation of 6-(benzylsulfanyl)pyridine-3-carbonitrile

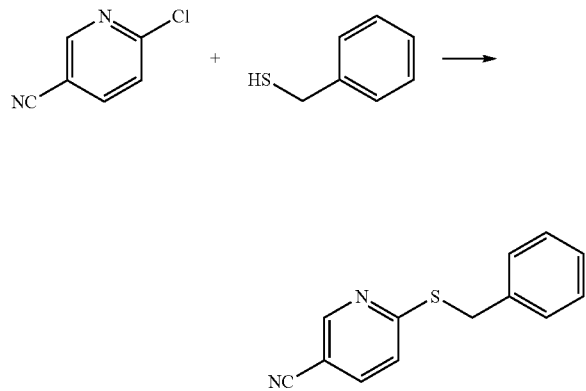

A mixture of 6-chloropyridine-3-carbonitrile (2.5 g, 18.04 mmol), N, N-dimethylformamide (40 mL), phenylmethanethiol (2.23 g, 17.95 mmol), and $Cs_2CO_3$ (7.08 g, 21.73 mmol) was stirred for overnight at room temperature. The resulting solution was stirred for an additional 6 h while the temperature was maintained at 60° C. in an oil bath. The solids were filtered out. The resulting solution was diluted with water, extracted with ethyl acetate, dried over anhydrous sodium sulfate, and concentrated under vacuum. The residue was purified by a silica gel column eluting with ethyl acetate/petroleum ether (1:3) to afford the title compound (3.8 g, 93%) as a white solid. LCMS [M+H$^+$] 227.

Step 2: Preparation of 5-cyanopyridine-2-sulfonyl Chloride

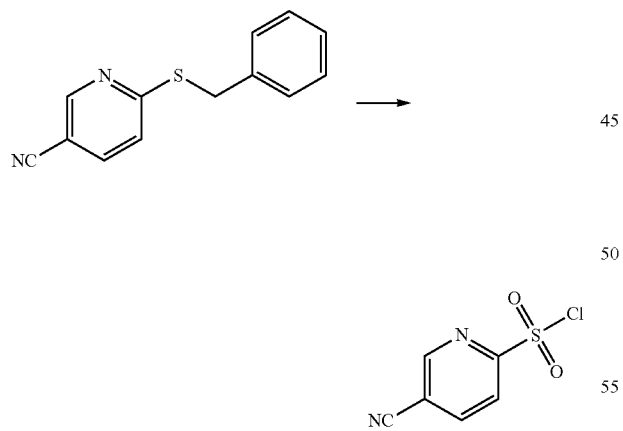

Concentrated aqueous HCl (6 mL) was added into a mixture of 6-(benzylsulfanyl)pyridine-3-carbonitrile (1 g, 4.42 mmol), dichloromethane (30 mL), and water (15 mL) dropwise with stirring at 0° C. To this was added sodium hypochlorite (12 mL, 14.5% available chlorine) dropwise with stirring at 0° C. The resulting mixture was stirred for 10 min at 0° C. The solution of the title compound in dichloromethane layer was rapidly separated and was used directly for the next step without any further purification.

Step 3: Preparation of (2S,4R,5S)-1-(5-cyanopyridin-2-ylsulfonyl)-4-fluoro-5-methyl-N-((5-(trifluoromethyl)-2-(2-(trifluoromethyl)pyrimidin-5-yl)pyridin-4-yl)methyl)pyrrolidine-2-carboxamide

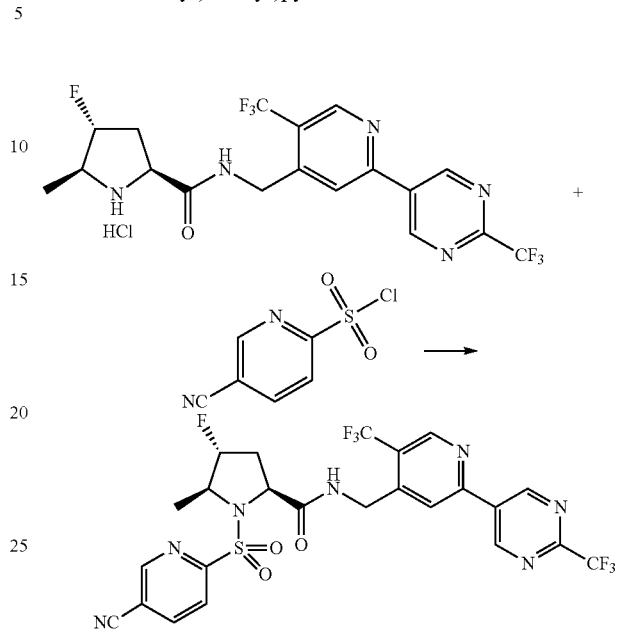

The cold solution of crude 5-cyanopyridine-2-sulfonyl chloride in dichloromethane was added dropwise into a mixture of (2S,4R,5S)-4-fluoro-5-methyl-N-[[5-(trifluoromethyl)-2-[2-(trifluoromethyl)pyrimidin-5-yl]pyridin-4-yl]methyl]pyrrolidine-2-carboxamide (100 mg, 0.21 mmol), dichloromethane (10 mL), and TEA (64.88 mg, 0.641 mmol) at 0° C. The resulting solution was stirred for 10 min at 0° C. in an ice/salt bath. The reaction was then quenched by water, extracted with dichloromethane, washed with brine, dried over anhydrous sodium sulfate, and concentrated under vacuum. The residue was purified by a silica gel column eluting with ethyl acetate/petroleum ether (1:1) to afford the title compound (17.0 mg, 12.4%) as a white solid. LCMS [M+H$^+$] 618. $^1$H NMR (400 MHz, CDCl$_3$) δ 9.68 (s, 2H), 9.13-8.90 (m, 2H), 8.41-8.23 (m, 2H), 8.18 (d, J=8.1 Hz, 1H), 7.35 (d, J=28.1 Hz, 1H), 5.11 (dd, J=16.3, 7.6 Hz, 2H), 4.88-4.60 (m, 2H), 4.27-4.09 (m, 1H), 2.81-2.56 (m, 1H), 2.56-2.33 (m, 1H), 1.37 (d, J=7.1 Hz, 3H).

Example 10

Preparation of (2S,4R,5S)—N-((5-chloro-2-(2-(trifluoromethyl)pyrimidin-5-yl)pyridin-4-yl)methyl)-4-fluoro-1-(5-fluoropyridin-2-ylsulfonyl)-5-methylpyrrolidine-2-carboxamide The overall reaction scheme is as follows:

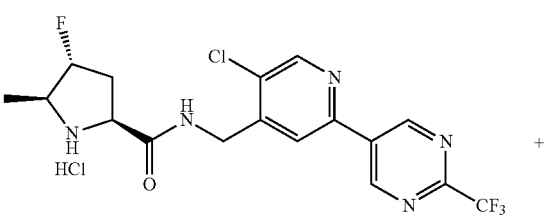

-continued

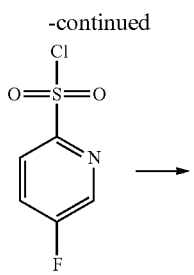

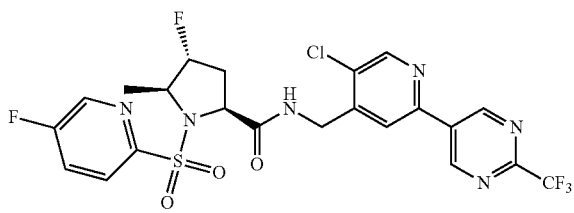

The cold solution of crude 5-fluoropyridine-2-sulfonyl chloride in dichloromethane (~0.3 M, 5 mL, prepared according to Example 2, Step 2) was added dropwise into a mixture of (2S,4R,5S)—N-([5-chloro-2-[2-(trifluoromethyl)pyrimidin-5-yl]pyridin-4-yl]methyl)-4-fluoro-5-methylpyrrolidine-2-carboxamide hydrochloride (100 mg, 0.24 mmol), dichloromethane (10 mL), and TEA (72 mg, 0.71 mmol) at 0° C. The resulting solution was stirred for 10 min at 0° C. in an ice/salt bath. The reaction was then quenched by water, extracted with dichloromethane, washed with brine, dried over anhydrous sodium sulfate, and concentrated under vacuum. The residue was purified by a silica gel column eluting with ethyl acetate/petroleum ether (1:1) to afford the title compound (24.1 mg, 17%) as a white solid. LCMS [M+H$^+$] 577. $^1$H NMR (400 MHz, CDCl$_3$) δ 9.62 (s, 2H), 8.71 (s, 1H), 8.60 (d, J=2.7 Hz, 1H), 8.20 (s, 1H), 8.11 (dd, J=8.6, 4.1 Hz, 1H), 7.75-7.60 (m, 1H), 7.54 (s, 1H), 5.10-4.92 (m, 2H), 4.76 (dd, J=25.6, 3.2 Hz, 1H), 4.53 (dd, J=17.9, 5.1 Hz, 1H), 4.23 (dd, J=22.2, 6.9 Hz, 1H), 2.73-2.52 (m, 1H), 2.52-2.29 (m, 1H), 1.35 (d, J=7.1 Hz, 3H).

Example 11

Preparation of (2S,4R,5S)—N-(2-cyano-5-(2-(trifluoromethyl)pyrimidin-5-yl)benzyl)-4-fluoro-1-(5-fluoropyridin-2-ylsulfonyl)-5-methylpyrrolidine-2-carboxamide The overall reaction scheme is as follows:

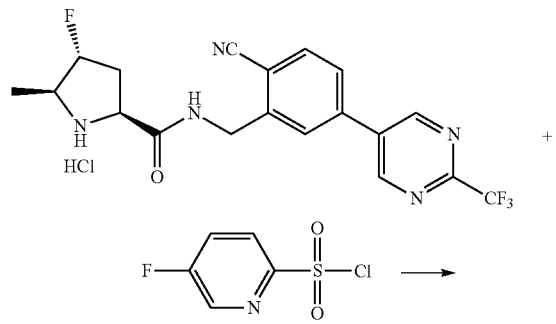

-continued

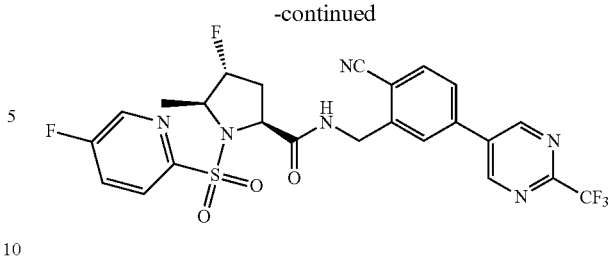

The cold solution of crude 5-fluoropyridine-2-sulfonyl chloride in dichloromethane (~0.3 M, 10 mL, prepared according to Example 2, Step 2) was added dropwise into a mixture of (2S,4R,5S)—N-([2-cyano-5-[2-(trifluoromethyl)pyrimidin-5-yl]phenyl]methyl)-4-fluoro-5-methylpyrrolidine-2-carboxamide hydrochloride (230 mg, 0.57 mmol), dichloromethane (20 mL), and TEA (171 mg, 1.69 mmol) at 0° C. The resulting solution was stirred for 1 h at room temperature, diluted with water, extracted with dichloromethane, washed with brine, dried over anhydrous sodium sulfate and concentrated under vacuum. The residue was purified by a silica gel column eluting with dichloromethane/ethyl acetate (2/1) to afford the title compound (82.2 mg, 26%) as a white solid. LCMS [M+H$^+$] 567. $^1$H NMR (400 MHz, CDCl$_3$) δ 9.22 (s, 2H), 8.59 (s, 1H), 8.12-8.01 (m, 2H), 7.87 (s, 1H), 7.70-7.61 (m, 2H), 7.57 (m, 1H), 5.12-5.06 (m, 1H), 5.00-4.96 (m, 1H), 4.83-4.69 (m, 2H), 2.70-2.33 (m, 2H), 1.34 (d, J=7.0 Hz, 3H).

Example 12

Preparation of (2S,4R,5S)-4-fluoro-1-(5-fluoropyridin-2-ylsulfonyl)-5-methyl-N-((5-(trifluoromethoxy)-2-(2-(trifluoromethyl)pyrimidin-5-yl)pyridin-4-yl)methyl)pyrrolidine-2-carboxamide The overall reaction scheme is as follows:

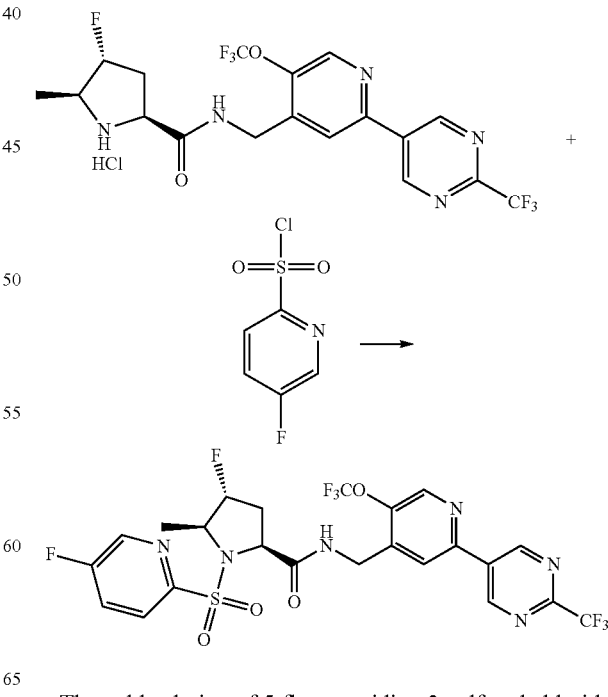

The cold solution of 5-fluoropyridine-2-sulfonyl chloride in dichloromethane (~0.3 M, 5 mL, prepared according to Example 2, Step 2) was added dropwise into a mixture of (2S,4R,5S)-4-fluoro-5-methyl-N-[[5-(trifluoromethoxy)-2-[2-(trifluoromethyl)pyrimidin-5-yl]pyridin-4-yl]methyl]pyrrolidine-2-carboxamide hydrochloride (100 mg, 0.21 mmol), dichloromethane (10 mL), and TEA (64.88 mg, 0.64 mmol) at 0° C. The resulting solution was stirred for 10 min at 0° C. in an ice/salt bath. The reaction was then quenched by water, extracted with dichloromethane, washed with brine, dried over anhydrous sodium sulfate, and concentrated under vacuum. The residue was purified by a silica gel column eluting with ethyl acetate/petroleum ether (1:1) to afford the title compound (17.7 mg, 13%) as a white solid. LCMS [M+H$^+$] 627. $^1$H NMR (400 MHz, CDCl$_3$) δ 9.63 (s, 2H), 8.70 (d, J=1.4 Hz, 1H), 8.60 (d, J=2.7 Hz, 1H), 8.27 (s, 1H), 8.11 (dd, J=8.7, 4.2 Hz, 1H), 7.74-7.62 (m, 1H), 7.51-7.41 (m, 1H), 5.11-4.95 (m, 2H), 4.76 (dd, J=51.5, 3.1 Hz, 1H), 4.54 (dd, J=17.7, 5.0 Hz, 1H), 4.30-4.14 (m, 1H), 2.74-2.56 (m, 1H), 2.52-2.27 (m, 1H), 1.35 (d, J=7.1 Hz, 3H).

Example 13

Preparation of (2S,4R,5S)-4-fluoro-N-((5-fluoro-2-(2-(trifluoromethyl)pyrimidin-5-yl)pyridin-4-yl)methyl)-1-(5-fluoropyridin-2-ylsulfonyl)-5-methyl-pyrrolidine-2-carboxamide The overall reaction scheme is as follows:

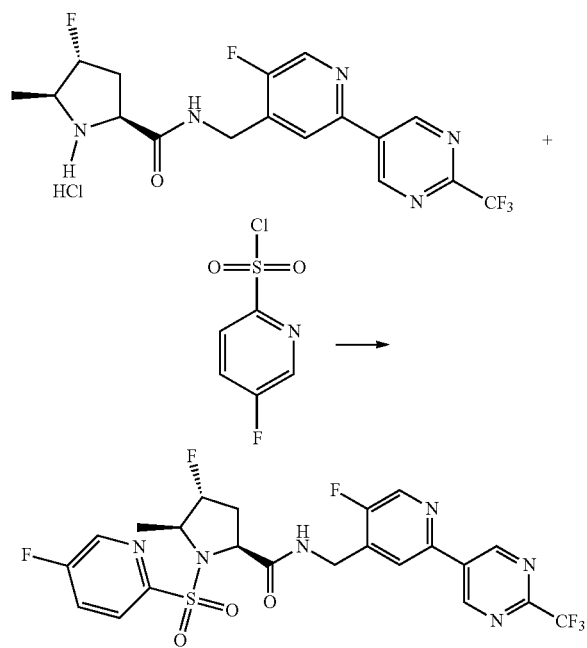

The cold solution of crude 5-fluoropyridine-2-sulfonyl chloride in dichloromethane (~0.3 M, 5 mL, prepared according to Example 2, Step 2) was added dropwise into a mixture of (2S,4R,5S)-4-fluoro-N-([5-fluoro-2-[2-(trifluoromethyl)pyrimidin-5-yl]pyridin-4-yl]methyl)-5-methylpyrrolidine-2-carboxamide hydrochloride (100 mg, 0.25 mmol), dichloromethane (20 mL), and TEA (76 mg, 0.75 mmol) at 0° C. The resulting solution was stirred for 60 min at room temperature. The resulting solution was diluted with water, extracted with dichloromethane, washed with brine, dried over anhydrous sodium sulfate, and concentrated under vacuum. The residue was purified by a silica gel column eluting with ethyl acetate/petroleum ether (100/1) to afford the title compound (38.5 mg, 28%) as a white solid. LCMS [M+H$^+$] 561. $^1$H NMR (400 MHz, CDCl$_3$) δ 9.58 (s, 2H), 8.59 (d, J=3.4 Hz, 2H), 8.19 (d, J=5.6 Hz, 1H), 8.11 (dd, J=8.6, 4.2 Hz, 1H), 7.67 (td, J=8.3, 2.8 Hz, 1H), 7.49 (d, J=7.0 Hz, 1H), 5.09-4.93 (m, 2H), 4.76 (dd, J=52, 2.8 Hz, 1H), 4.55 (dd, J=17.4, 5.0 Hz, 1H), 4.23 (dt, J=20.6, 7.2 Hz, 1H), 2.71-2.56 (m, 1H), 2.52-2.31 (m, 1H), 1.34 (d, J=7.1 Hz, 3H).

Example 14

Preparation of (2S,4R,5S)—N-((5-cyano-2-(2-(trifluoromethyl)pyrimidin-5-yl)pyridin-4-yl)methyl)-4-fluoro-1-(5-fluoropyridin-2-ylsulfonyl)-5-methylpyrrolidine-2-carboxamide The overall reaction scheme is as follows:

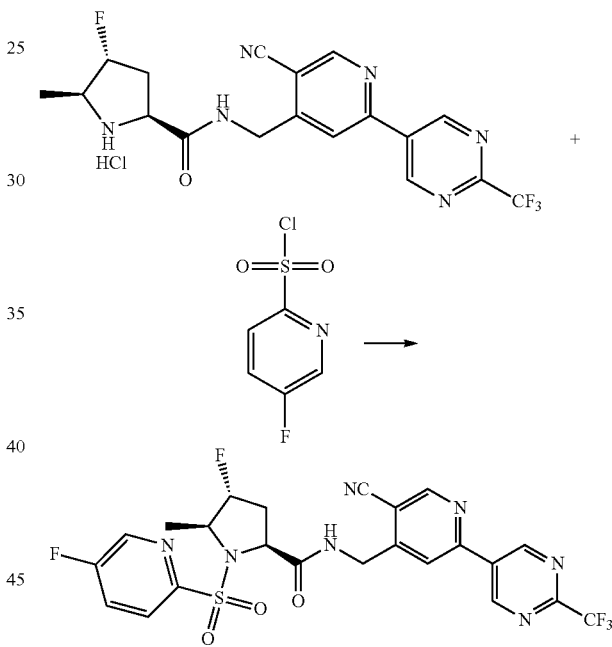

The cold solution of crude 5-fluoropyridine-2-sulfonyl chloride in dichloromethane (~0.3 M, 5 mL, prepared according to Example 2, Step 2) was added dropwise into a mixture of (2S,4R,5S)—N-([5-cyano-2-[2-(trifluoromethyl)pyrimidin-5-yl]pyridin-4-yl]methyl)-4-fluoro-5-methylpyrrolidine-2-carboxamide hydrochloride (200 mg, 0.49 mmol), dichloromethane (20 mL), and TEA (136 mg, 1.34 mmol) at 0° C. The resulting solution was stirred for 30 min at room temperature. The resulting solution was diluted with water, extracted with dichloromethane, washed with brine, dried over anhydrous sodium sulfate and concentrated under vacuum. The residue was purified by a silica gel column eluting with dichloromethane/ethyl acetate (1/1) to afford the title compound (65.7 mg, 24%) as a white solid. LCMS [M+H$^+$] 568. $^1$H NMR (400 MHz, CDCl$_3$) δ 9.69 (s, 2H), 8.99 (d, J=0.8 Hz, 1H), 8.61 (d, J=2.8 Hz, 1H), 8.36 (s, 1H), 8.12 (dd, J=8.6, 4.1 Hz, 1H), 7.69 (ddd, J=8.7, 7.7, 2.8 Hz, 1H), 7.57 (t, J=6.3 Hz, 1H), 5.21-5.01 (m, 2H), 4.78 (dd, J=51.3, 3.3 Hz, 1H), 4.69-4.59 (m, 1H), 4.27-4.15 (m, 1H), 2.67 (td, J=18.0, 16.7, 8.1 Hz, 1H), 2.50-2.27 (m, 1H), 1.37 (d, J=7.1 Hz, 3H).

Example 15

Preparation of (2S,4R,5S)—N-((2-(difluoromethyl)-5-(2-(trifluoromethyl)pyrimidin-5-yl)pyridin-3-yl)methyl)-4-fluoro-1-(5-fluoropyridin-2-ylsulfonyl)-5-methylpyrrolidine-2-carboxamide The overall reaction scheme was as follows:

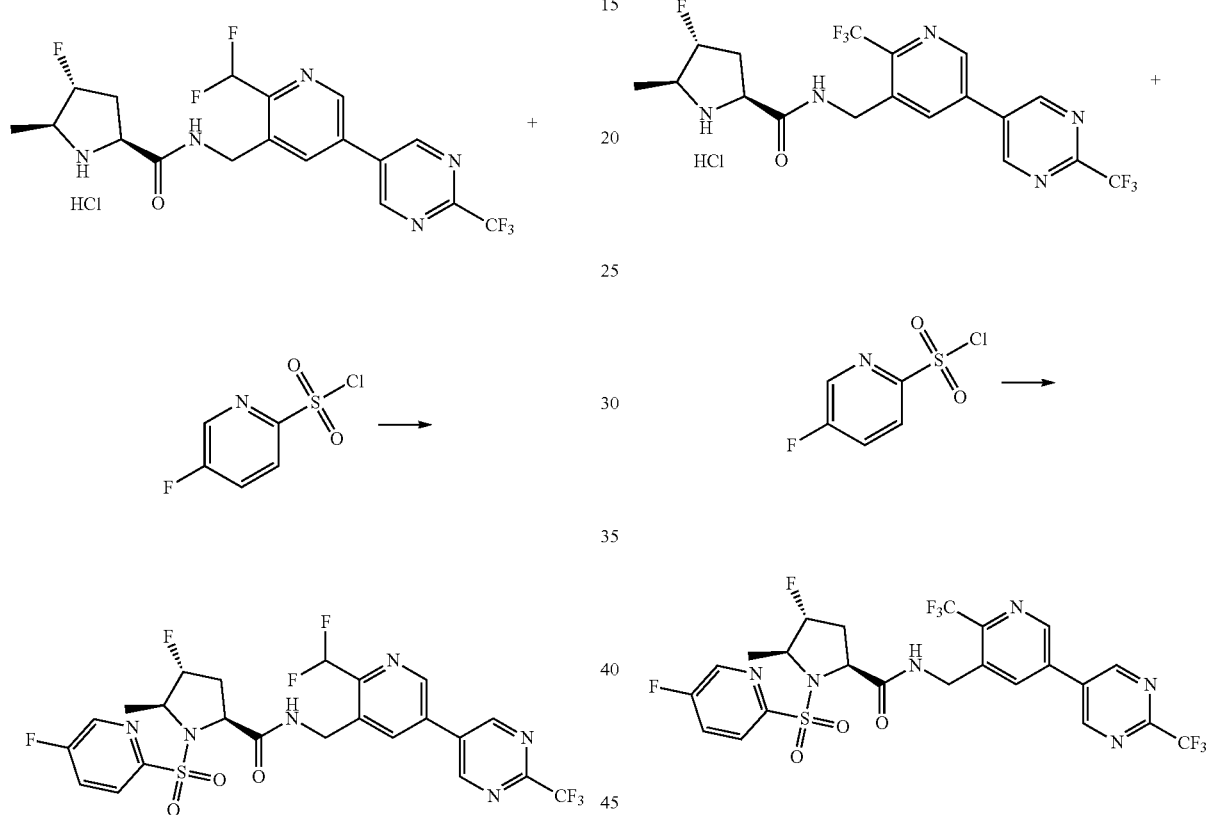

The cold solution of crude 5-fluoropyridine-2-sulfonyl chloride in dichloromethane (~0.3 M, 5 mL, prepared according to Example 2, Step 2) was added dropwise into a mixture of (2S,4R,5S)—N-[2-(difluoromethyl)-5-[2-(trifluoromethyl)pyrimidin-5-yl]pyridin-3-yl]methyl-4-fluoro-5-methylpyrrolidine-2-carboxamide hydrochloride (90 mg, 0.21 mmol), dichloromethane (20 mL), and TEA (63 mg, 0.62 mmol) at 0° C. The resulting solution was stirred for 0.5 h at room temperature. The resulting solution was diluted with water, extracted with dichloromethane, washed with brine, dried over anhydrous sodium sulfate and concentrated under vacuum. The residue was purified by a silica gel column eluting with ethyl acetate/petroleum ether (1/1) to afford the title compound (59.5 mg, 24%) as a white solid. LCMS [M+H$^+$] 593. $^1$H NMR (400 MHz, CDCl$_3$). δ 9.25 (s, 2H), 8.82-8.76 (m, 1H), 8.57 (d, J=2.7 Hz, 1H), 8.43 (d, J=2.1 Hz, 1H), 8.07 (dd, J=8.7, 4.2 Hz, 1H), 7.65 (ddd, J=8.7, 7.7, 2.8 Hz, 1H), 7.48 (t, J=6.5 Hz, 1H), 6.85 (t, J=54.4 Hz, 1H), 5.16 (dd, J=16.8, 7.7 Hz, 1H), 4.97 (dd, J=9.4, 8.2 Hz, 1H), 4.81 (t, J=3.7 Hz, 1H), 4.73 (dd, J=31.7, 4.1 Hz, 1H), 4.21 (dq, J=20.7, 7.0 Hz, 1H), 2.70-2.54 (m, 1H), 2.48-2.30 (m, 1H), 1.33 (d, J=7.1 Hz, 3H).

Example 16

Preparation of (2S,4R,5S)-4-fluoro-1-(5-fluoropyridin-2-ylsulfonyl)-5-methyl-N-((2-(trifluoromethyl)-5-(2-(trifluoromethyl)pyrimidin-5-yl)pyridin-3-yl)methyl)pyrrolidine-2-carboxamide The overall reaction scheme is as follows:

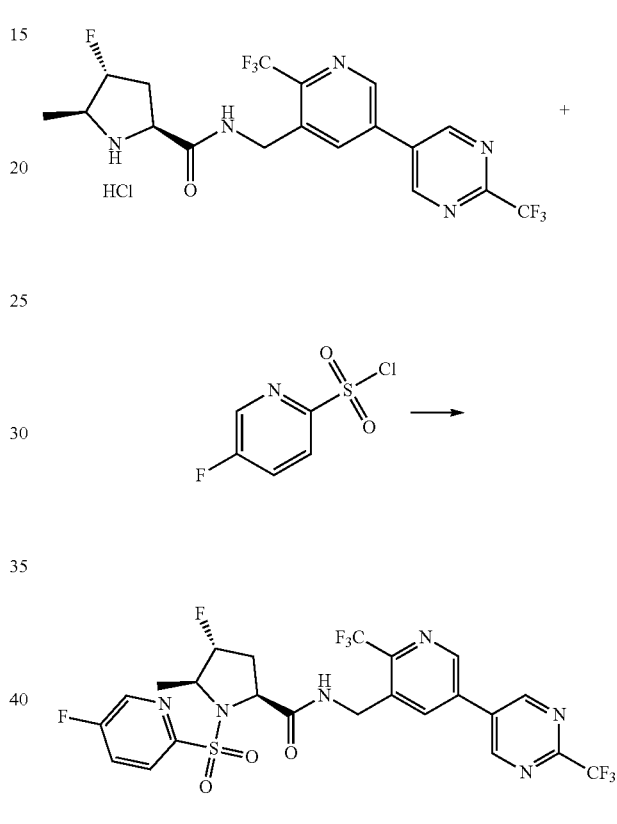

The cold solution of crude 5-fluoropyridine-2-sulfonyl chloride in dichloromethane (~0.3 M, 5 mL, prepared according to Example 2, Step 2) was added dropwise into a mixture of (2S,4R,5S)-4-fluoro-5-methyl-N-[[5-(trifluoromethyl)-2-[2-(trifluoromethyl)pyrimidin-5-yl]pyridin-4-yl]methyl]pyrrolidine-2-carboxamide (100 mg, 0.21 mmol), dichloromethane (10 mL), and TEA (64.88 mg, 0.64 mmol) at 0° C. The resulting solution was stirred for 10 min at 0° C. in an ice/salt bath. The reaction was then quenched by water, extracted with dichloromethane, washed with brine, dried over anhydrous sodium sulfate, and concentrated under vacuum. The residue was purified by a silica gel column eluting with ethyl acetate/petroleum ether (1:1). This resulted in the title compound (22.9 mg, 16.9%) as a white solid. LCMS [M+H$^+$] 611. $^1$H NMR (400 MHz, CDCl$_3$) δ 9.27 (s, 2H), 8.87 (d, J=2.1 Hz, 1H), 8.58 (d, J=2.7 Hz, 1H), 8.50 (d, J=2.1 Hz, 1H), 8.08 (dd, J=8.6, 4.2 Hz, 1H), 7.66 (ddd, J=8.7, 7.7, 2.8 Hz, 1H), 7.49 (d, J=7.2 Hz, 1H), 5.14 (dd, J=17.0, 7.6 Hz, 1H), 5.01 (t, J=8.8 Hz, 1H), 4.77 (dd, J=42.8, 4.1 Hz, 1H), 4.68 (dd, J=8.3, 4.2 Hz, 1H), 4.27-4.15 (m, 1H), 2.71-2.55 (m, 1H), 2.51-2.29 (m, 1H), 1.33 (d, J=7.1 Hz, 3H).

Example 17

Preparation of (2S,4R,5S)-4-fluoro-1-(6-fluoropyridin-3-ylsulfonyl)-5-methyl-N-((5-(trifluoromethyl)-2-(2-(trifluoromethyl)pyrimidin-5-yl)pyridin-4-yl)methyl)pyrrolidine-2-carboxamide The overall reaction scheme is as follows:

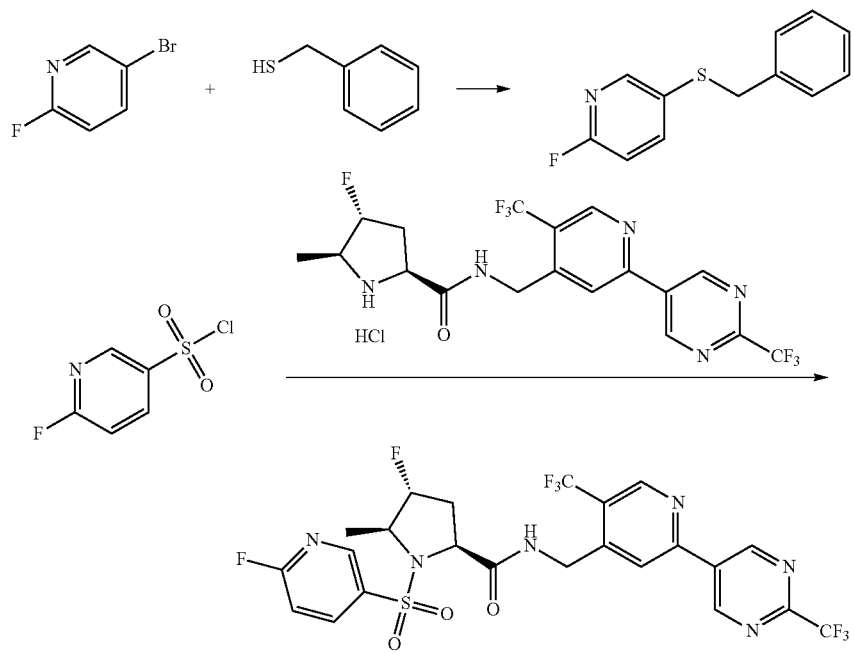

Step 1: Preparation of 5-(benzylsulfanyl)-2-fluoropyridine

Step 2: Preparation of 6-fluoropyridine-3-sulfonyl Chloride

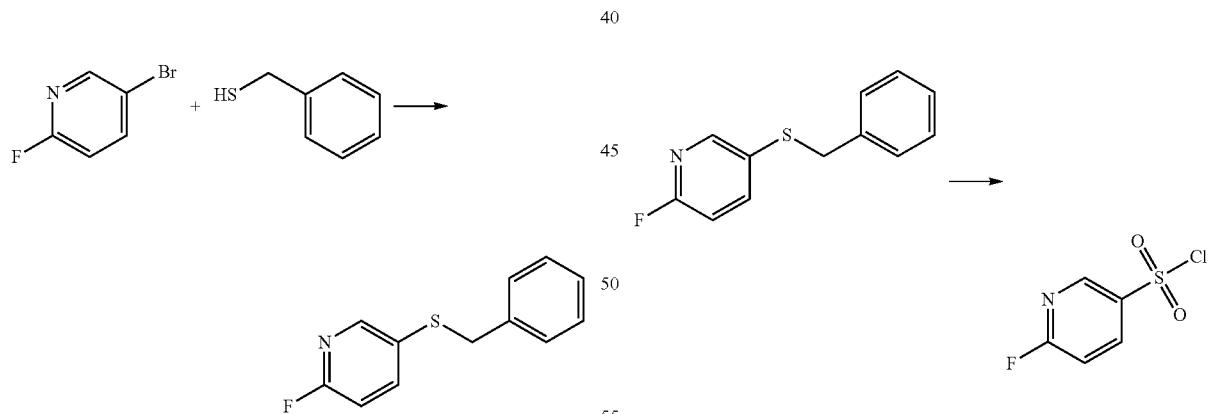

A mixture of 5-bromo-2-fluoropyridine (3 g, 17.05 mmol), toluene (30 mL), DIEA (6.57 g, 50.83 mmol), phenylmethanethiol (2.32 g, 18.68 mmol), XantPhos (1.5 g, 2.59 mmol), and $Pd_2(dba)_3$ (880 mg, 0.96 mmol) was stirred for 3 h at 110° C. in an oil bath under nitrogen. The resulting mixture was diluted with water, extracted with ethyl acetate, washed with brine, dried over anhydrous sodium sulfate, and concentrated under vacuum. The residue was purified by a silica gel column eluting with ethyl acetate/petroleum ether (1:10) to afford the title compound (2.6 g, 70%) as yellow oil.

Concentrated hydrogen chloride (6 mL) was added into a mixture of 5-(benzylsulfanyl)-2-fluoropyridine (1 g, 4.56 mmol), dichloromethane (30 mL, 471.90 mmol), and water (15 mL, 832.63 mmol) dropwise with stirring at 0° C. To this solution was added sodium hypochlorite (12 mL, 14.5% available chlorine) dropwise with stirring at 0° C. The resulting mixture was stirred for 30 min at 0° C. The mixture was separated and the organic solution was washed with cold 5% $Na_2S_2O_3$ and cold brine, and dried over anhydrous sodium sulfate. This resulted in a cold solution of the title compound in dichloromethane which was used for the next step without any further purification.

Step 3: Preparation of (2S,4R,5S)-4-fluoro-1-(6-fluoropyridin-3-ylsulfonyl)-5-methyl-N-((5-(trifluoromethyl)-2-(2-(trifluoromethyl)pyrimidin-5-yl)pyridin-4-yl)methyl)pyrrolidine-2-carboxamide

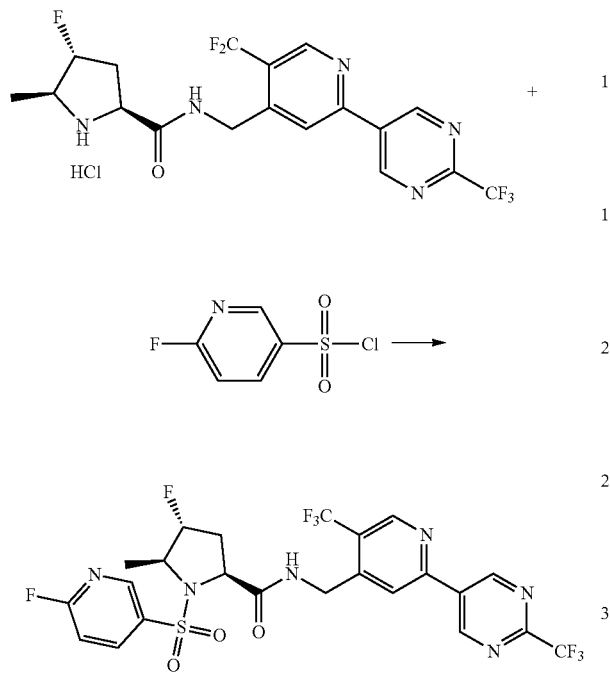

The cold solution of crude 6-fluoropyridine-3-sulfonyl chloride in dichloromethane (~0.15 M, 10 mL, prepared from Step 2) was added dropwise into a mixture of (2S,4R,5S)-4-fluoro-5-methyl-N-[[5-(trifluoromethyl)-2-[2-(trifluoromethyl)pyrimidin-5-yl]pyridin-4-yl]methyl]pyrrolidine-2-carboxamide hydrochloride (100 mg, 0.21 mmol), dichloromethane (10 mL), and TEA (64.88 mg, 0.64 mmol) at 0° C. The resulting solution was stirred for 10 min at 0° C. in an ice/salt bath. The reaction was then quenched by the addition of water, extracted with dichloromethane, washed with brine, dried over anhydrous sodium sulfate, and concentrated under vacuum. The residue was purified by a silica gel column eluting with ethyl acetate/petroleum ether (1:1). This resulted in the title compound (17.0 mg, 12.4%) as a white solid. LCMS [M+H$^+$] 611. $^1$H NMR (400 MHz, CDCl$_3$) δ 9.68 (s, 2H), 9.06-9.00 (m, 1H), 8.82-8.76 (m, 1H), 8.34-8.26 (m, 2H), 7.34-7.31 (m, 1H), 7.18 (dd, J=8.6, 2.8 Hz, 1H), 5.19 (dd, J=17.7, 8.1 Hz, 1H), 4.81 (dd, J=51.1, 3.0 Hz, 1H), 4.61 (dd, J=17.6, 4.8 Hz, 1H), 4.32 (dd, J=9.9, 7.9 Hz, 1H), 4.19-4.07 (m, 1H), 2.73-2.62 (m, 1H), 2.34 (dddd, J=43.5, 15.0, 9.9, 3.2 Hz, 1H), 1.42 (d, J=7.0 Hz, 3H).

Example 18

IC50 Determinations of Exemplified Compounds

The IC$_{50}$ (effective concentration) of compounds on the human and rat TRPA1 channels were determined using a FLIPR Tetra instrument. CHO cells expressing TRPA1 were plated into 384-well plates, incubated overnight at 37° C., and loaded with BD calcium indicator dye for 1 hr at 37° C. followed by 15 minutes at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 20 minutes at room temperature prior to adding agonist. Following this incubation, about an EC$_{80}$ concentration of cinnamaldehyde (75 uM for human TRPA1 and 45 uM for rat TRPA1) was added to active the channels and block of cinnamaldehyde induced calcium influx was measured.

The IC$_{50}$ results were fit with a standard Hill function, keeping the Hill coefficient (n) fixed to 1.5. Fixing the Hill coefficient will generally reduce variability of the IC$_{50}$ determination. The IC$_{50}$ results were individually examined to make sure the MIN and MAX points were set correctly prior to validation of the results.

The IC$_{50}$ (hTRPA1 IC$_{50}$ (micromolar)), proton NMR data for and LCMS results for compounds of the present disclosure are shown in Table 1 below where "hTRPA1" refers to hTRPA1 CHO Ca2+ AUC EVO (IC$_{50}$).

TABLE 1

| Structure | hTRPA1 | $^1$H NMR (ppm) | LCMS M + H |
|---|---|---|---|
| [1] | 0.00269 | $^1$H NMR (300 MHz, CDCl$_3$) δ 9.68 (s, 2H), 9.00 (s, 1H), 8.58 (s, 1H), 8.35 (s, 1H), 8.12-8.07 (m, 1H), 7.69-7.63 (m, 1H), 7.53-7.49 (m, 1H), 5.22-4.99 (m, 2H), 4.71-4.56 (m, 2H), 4.26-4.17 (m, 1H), 2.68-2.57 (m, 1H), 2.49-2.27 (m, 1H), 1.34 (d, J = 7.0 Hz, 3H) | 611 |

TABLE 1-continued
| Structure | hTRPA1 | ¹H NMR (ppm) | LCMS M + H |
|---|---|---|---|
| 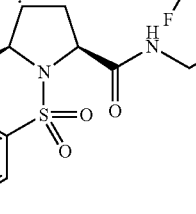<br>[2] | 0.032 | ¹H NMR (400 MHz, CDCl₃) δ 9.71 (s, 2H), 9.38 (s, 1H), 9.02 (s, 1H), 8.95 (d, J = 5.0 Hz, 1H), 8.38 (s, 1H), 8.32 (d, J = 8.2 Hz, 1H), 7.68 (t, J = 6.6 Hz, 2H), 5.08 (d, J = 18.5 Hz, 1H), 4.84-4.64 (m, 2H), 4.44 (t, J = 8.9 Hz, 1H), 4.14 (dt, J = 21.0, 7.2 Hz, 1H), 2.63-2.53 (m, 1H), 2.35 (dt, J = 43.2, 11.7 Hz, 1H), 1.42 (s, 3H) | 593 |
| 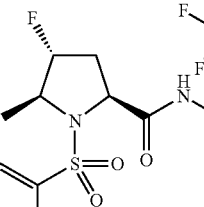<br>[3] | 0.00309 | ¹H NMR (400 MHz, CDCl₃) δ 9.72 (s, 2H), 9.05 (s, 1H), 9.01-8.95 (m, 1H), 8.86 (s, 1H), 8.32 (s, 1H), 8.17 (m, 1H), 7.35-7.29 (m, 1H), 5.20-5.14 (m, 1H), 4.88-4.74 (m, 1H), 4.67-4.61 (m, 1H), 4.38-4.34 (m, 1H), 4.38-4.11 (m, 1H), 2.69-2.63 (m, 1H), 2.45-2.30 (m, 1H), 1.42 (d, J = 7.1 Hz, 3H) | 627 |
| 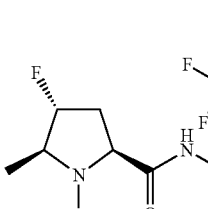<br>[4] | 0.000634 | ¹H NMR (300 MHz, CDCl₃) δ 9.66 (s, 2H), 9.02 (s, 1H), 8.48 (d, J = 5.9 Hz, 1H), 8.25 (s, 1H), 7.62 (d, J = 0.9 Hz, 1H), 7.51 (dd, J = 5.8, 0.9 Hz, 1H), 7.23-7.20 (m, 1H), 5.15 (dd, J = 17.7, 7.6 Hz, 1H), 4.83-4.58 (m, 3H), 4.29 (dd, J = 20.6, 7.0 Hz, 1H), 2.84-2.63 (m, 1H), 2.50-2.34 (m, 1H), 1.42 (d, J = 7.1 Hz, 3H) | 667 |
| <br>[5] | 0.00191 | ¹H NMR (300 MHz, CDCl₃) δ 9.72 (s, 2H), 9.30 (s, 1H), 8.81 (d, J = 6.2 Hz, 1H), 8.32 (s, 1H), 8.08-7.72 (m, 2H), 7.51 (s, 1H), 5.22-4.62 (m, 4H), 4.35 (dd, J = 20.4, 7.2 Hz, 1H), 2.81-2.22 (m, 2H), 1.47 (s, 3H) | 633 |

TABLE 1-continued

| Structure | hTRPA1 | ¹H NMR (ppm) | LCMS M + H |
|---|---|---|---|
| [6] | 0.00216 | ¹H NMR (400 MHz, CDCl₃) δ 9.69 (s, 2H), 9.01 (s, 1H), 8.69 (d, J = 2.1 Hz, 1H), 8.35 (s, 1H), 7.98 (dt, J = 8.4, 5.3 Hz, 2H), 7.54 (s, 1H), 5.20-5.02 (m, 2H), 4.71 (ddd, J = 34.4, 22.3, 3.8 Hz, 2H), 4.31-4.11 (m, 1H), 2.78-2.56 (m, 1H), 2.55-2.28 (m, 1H), 1.35 (d, J = 7.1 Hz, 3H) | 627 |
| [7] | 0.633 | ¹H NMR (400 MHz, CDCl₃) δ 9.73 (s, 2H), 9.01 (s, 1H), 8.60 (dt, J = 4.3, 1.5 Hz, 1H), 8.36 (s, 1H), 7.78-7.63 (m, 2H), 7.52 (s, 1H), 5.15 (dd, J = 17.8, 7.7 Hz, 1H), 4.93 (t, J = 8.8 Hz, 1H), 4.82 (dd, J = 51.2, 3.3 Hz, 1H), 4.64 (dd, J = 17.6, 4.7 Hz, 1H), 4.48-4.36 (m, 1H), 2.75-2.60 (m, 1H), 2.55-2.33 (m, 1H), 1.39 (d, J = 7.0 Hz, 3H) | 611 |
| [8] | 0.0735 | ¹H NMR (400 MHz, CDCl₃) δ 9.68 (s, 2H), 9.13-8.90 (m, 2H), 8.41-8.23 (m, 2H), 8.18 (d, J = 8.1 Hz, 1H), 7.35 (d, J = 28.1 Hz, 1H), 5.11 (dd, J = 16.3, 7.6 Hz, 2H), 4.88-4.60 (m, 2H), 4.27-4.09 (m, 1H), 2.81-2.56 (m, 1H), 2.56-2.33 (m, 1H), 1.37 (d, J = 7.1 Hz, 3H) | 618 |
| [9] | 0.0167 | ¹H NMR (400 MHz, CDCl₃) δ 9.62 (s, 2H), 8.71 (s, 1H), 8.60 (d, J = 2.7 Hz, 1H), 8.20 (s, 1H), 8.11 (dd, J = 8.6, 4.1 Hz, 1H), 7.75-7.60 (m, 1H), 7.54 (s, 1H), 5.10-4.92 (m, 2H), 4.76 (dd, J = 25.6, 3.2 Hz, 1H), 4.53 (dd, J = 17.9, 5.1 Hz, 1H), 4.23 (dd, J = 22.2, 6.9 Hz, 1H), 2.73-2.52 (m, 1H), 2.52-2.29 (m, 1H), 1.35 (d, J = 7.1 Hz, 3H) | 577 |
| [10] | 0.0669 | ¹H NMR (400 MHz, CDCl₃) δ 9.22 (s, 2H), 8.59 (s, 1H), 8.12-8.01 (m, 2H), 7.87 (s, 1H), 7.70-7.61 (m, 2H), 7.57 (m, 1H), 5.12-5.06 (m, 1H), 5.00-4.96 (m, 1H), 4.83-4.69 (m, 2H), 2.70-2.33 (m, 2H), 1.34 (d, J = 7.0 Hz, 3H) | 567 |

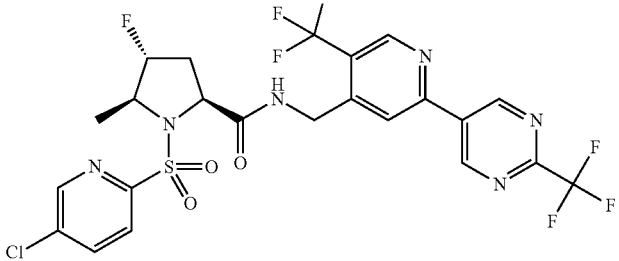

TABLE 1-continued

| Structure | hTRPA1 | ¹H NMR (ppm) | LCMS M + H |
|---|---|---|---|
| [11] | 0.00673 | ¹H NMR (400 MHz, CDCl₃) δ 9.63 (s, 2H), 8.70 (d, J = 1.4 Hz, 1H), 8.60 (d, J = 2.7 Hz, 1H), 8.27 (s, 1H), 8.11 (dd, J = 8.7, 4.2 Hz, 1H), 7.74-7.62 (m, 1H), 7.51-7.41 (m, 1H), 5.11-4.95 (m, 2H), 4.76 (dd, J = 51.5, 3.1 Hz, 1H), 4.54 (dd, J = 17.7, 5.0 Hz, 1H), 4.30-4.14 (m, 1H), 2.74-2.56 (m, 1H), 2.52-2.27 (m, 1H), 1.35 (d, J = 7.1 Hz, 3H) | 627 |
| [12] | 0.103 | ¹H NMR (400 MHz, CDCl₃) δ 9.58 (s, 2H), 8.59 (m, 2H), 8.19 (m, 1H), 8.11 (m, 1H), 7.67 (m, 1H), 7.49 (m, 1H), 7.29 (s, 2H), 5.09-4.93 (m, 2H), 4.83 (m, 1H), 4.55 (m, 1H), 4.23 (m, 1H), 2.71-2.56 (m, 1H), 2.49-2.32 (m, 1H), 1.34 (d, J = 7.1 Hz, 3H) | 561 |
| [13] | 0.0898 | ¹H NMR (400 MHz, CDCl₃) δ 9.69 (s, 2H), 8.99 (d, J = 0.8 Hz, 1H), 8.61 (d, J = 2.8 Hz, 1H), 8.36 (s, 1H), 8.12 (dd, J = 8.6, 4.1 Hz, 1H), 7.69 (ddd, J = 8.7, 7.7, 2.8 Hz, 1H), 7.57 (t, J = 6.3 Hz, 1H), 5.21-5.01 (m, 2H), 4.78 (dd, J = 51.3, 3.3 Hz, 1H), 4.69-4.59 (m, 1H), 4.27-4.15 (m, 1H), 2.67 (td, J = 18.0, 16.7, 8.1 Hz, 1H), 2.50-2.27 (m, 1H), 1.37 (d, J = 7.1 Hz, 3H) | 568 |
| [14] | 0.0751 | ¹H NMR (400 MHz, CDCl₃). δ 9.25 (s, 2H), 8.82-8.76 (m, 1H), 8.57 (d, J = 2.7 Hz, 1H), 8.43 (d, J = 2.1 Hz, 1H), 8.07 (dd, J = 8.7, 4.2 Hz, 1H), 7.65 (ddd, J = 8.7, 7.7, 2.8 Hz, 1H), 7.48 (t, J = 6.5 Hz, 1H), 6.85 (t, J = 54.4 Hz, 1H), 5.16 (dd, J = 16.8, 7.7 Hz, 1H), 4.97 (dd, J = 9.4, 8.2 Hz, 1H), 4.81 (t, J = 3.7 Hz, 1H), 4.73 (dd, J = 31.7, 4.1 Hz, 1H), 4.21 (dq, J = 20.7, 7.0 Hz, 1H), 2.70-2.54 (m, 1H), 2.48-2.30 (m, 1H), 1.33 (d, J = 7.1 Hz, 3H) | 593.1 |

TABLE 1-continued

| Structure | hTRPA1 | ¹H NMR (ppm) | LCMS M + H |
|---|---|---|---|
| [15] | 0.0477 | ¹H NMR (400 MHz, CDCl₃) δ 9.27 (s, 2H), 8.87 (d, J = 2.1 Hz, 1H), 8.58 (d, J = 2.7 Hz, 1H), 8.50 (d, J = 2.1 Hz, 1H), 8.08 (dd, J = 8.6, 4.2 Hz, 1H), 7.66 (ddd, J = 8.7, 7.7, 2.8 Hz, 1H), 7.49 (d, J = 7.2 Hz, 1H), 5.14 (dd, J = 17.0, 7.6 Hz, 1H), 5.01 (t, J = 8.8 Hz, 1H), 4.77 (dd, J = 42.8, 4.1 Hz, 1H), 4.68 (dd, J = 8.3, 4.2 Hz, 1H), 4.27-4.15 (m, 1H), 2.71- 2.55 (m, 1H), 2.51- 2.29 (m, 1H), 1.33 (d, J = 7.1 Hz, 3H) | 611 |
| [16] | NR | ¹H NMR (400 MHz, CDCl₃) δ 9.68 (s, 2H), 9.06-9.00 (m, 1H), 8.82-8.76 (m, 1H), 8.34-8.26 (m, 2H), 7.34-7.31 (m, 1H), 7.18 (dd, J = 8.6, 2.8 Hz, 1H), 5.19 (dd, J = 17.7, 8.1 Hz, 1H), 4.81 (dd, J = 51.1, 3.0 Hz, 1H), 4.61 (dd, J = 17.6, 4.8 Hz, 1H), 4.32 (dd, J = 9.9, 7.9 Hz, 1H), 4.19-4.07 (m, 1H), 2.73-2.62 (m, 1H), 2.34 (dddd, J = 43.5, 15.0, 9.9, 3.2 Hz, 1H), 1.42 (d, J = 7.0 Hz, 3H) | 611 |

Example 19: Comparative Pharmacokinetics

Certain pharmacokinetic attributes were evaluated for sulfonyl pyridyl compounds of the present disclosure. The results are shown in Table 3 below where: "hTRPA1" refers to IC₅₀ in nM; "hPPB" refers to human protein plasma binding in percent; "Corrected IC₅₀" refers to the hTRPA1 values corrected for hPPB; "HLM-CL$_{hep}$" refers to human liver microsome clearance in mL/min/kg; "K.Sol" refers to estimated aqueous solubility in μM; and "NR" refers to not run. Table 4 is a table of correspondence between the compound of Table 3 and a corresponding structure.

Human protein plasma binding may be measured according to the methods described by Banker et al., "Plasma/Serum Protein Binding Determinations," *Current Drug Metabolism* (2008), 9, 854-859, and Kariv et al., "Development of a high throughput equilibrium dialysis method," *J. Pharm Sci.* (2001) May; 90(5):580-87, as well as using commercially available assay kits by Wyatt, Cerep, Cyprotex and others.

Corrected hTRPA1 IC₅₀ (nM) was calculated using the equation:

$$(hTRPA1 IC_{50})/(100-hPPB/100).$$

For instance, for an hTRPA1 of 7.9 nM and a hPPB of 95.1%, a corrected IC₅₀ of 161 nM is calculated by: (7.9)/(100−95.1/100)=161.

Human liver microsome clearance (mL/min/kg) may be measured according to the method described by Ackley et al, "Metabolic Stability Assessed by Liver Microsomes and Hepatocytes", in "Optimization in Drug Discovery" in the "Methods in Pharmacology and Toxicology" series (ISSN 1557-2153), pp. 151-162 (Yan, Ed., Print ISBN 978-1-58829-332-9, Springer (2004), as well as by using commercially available assay kits by Cerep, Cyprotex, Bd Bioscience and others.

Aqueous solubility may be determined using the procedures reported by Alsenz et al., "High throughput solubility measurement in drug discovery and development," *Advanced Drug Delivery Reviews* (2007) 59, 546-568 and Kibbey et al., "An Integrated Process for Measuring the Physicochemical Properties of Drug Candidates in a Preclinical Discovery Environment," *J. Pharmaceutical Sci.* (2001) 90(8), 1164-1175.

TABLE 3

| Compound | hTRPA1 | hPPB | Corrected IC₅₀ | HLM-CL$_{hep}$ | K. Sol |
|---|---|---|---|---|---|
| Pyridyl Sulfonamide 1 | 7.9 | 95.1 | 161 | 4 | 30 |
| Pyridyl Sulfonamide 2 | 404 | 92.5 | 5,400 | NR | 4 |
| Pyridyl Sulfonamide 3 | 329 | 83.0 | 1936 | NR | NR |

TABLE 4

| Compound | Structure |
| --- | --- |
| Pyridyl Sulfonamide 1 | *(structure image)* |
| Pyridyl Sulfonamide 2 | *(structure image)* |
| Pyridyl Sulfonamide 3 | *(structure image)* |

Example 20

Comparative Pharmacokinetics

Certain pharmacokinetic variables were evaluated for two sulfonyl pyridyl compounds of the present disclosure (compounds 1 and 2 below) versus four sulfonyl pyridyl compounds falling outside the scope of the present disclosure (compounds 3 to 6 below. The results are shown in Table 5 below where: "h Ca2+ Max" refers to human CA2+ MAX $IC_{50}$ in μM; "HLM" refers to human liver microsome stability in mL/min/kg; "GSH trapping" refers to glutathione trapping; and "NR" refers to not run. Table 6 is a table of correspondence between the compound of Table 5 and a corresponding structure.

Human Ca2+ MAX $IC_{50}$ may be measured using one of the commercially available calcium assay kits provided by Molecular Devices, Abcam, Bio-Rad, Biovision, Enzo Lifesciences, Abnova, Sigma-Aldrich, or others.

Human liver microsome HLM stability may be measured as using the procedure of Ackley et al. as described above.

GSH trapping in a method for screening reactive metabolites for the potential to cause adverse drug reactions. Reactive metabolites may implicate clinical toxicity through drug compound bioactivation or inactivation of proteins. One such assessment utilizes in vitro incubations comprising glutathione (GSH) as a trapping reagent. LC/MS may be used to detect and characterize reactive intermediate formation as indicated by trapped glutathione adducts, as described by Yan et al., "Stable Isotope Trapping and High Throughput Screenings of Reactive Metabolites Using the Active MS Signature," *Anal. Chem.* (2004), 76, 6835-6847.

TABLE 5
| | Compound | H Ca2+ MAX | HLM | GSH trapping |
|---|---|---|---|---|
| 1 | 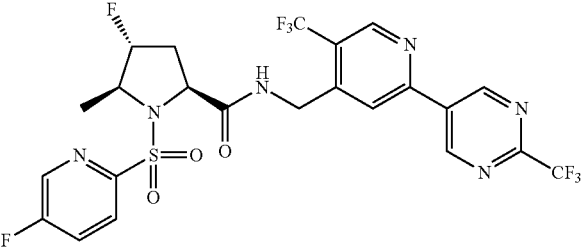 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(F)cn1]<br>Compound 1 | 0.008 | 4.1 | NR |
| 2 | 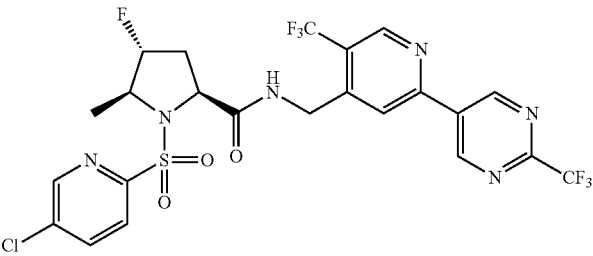 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(Cl)cn1]<br>Compound 2 | 0.006 | 6.1 | NR |
| 3 | 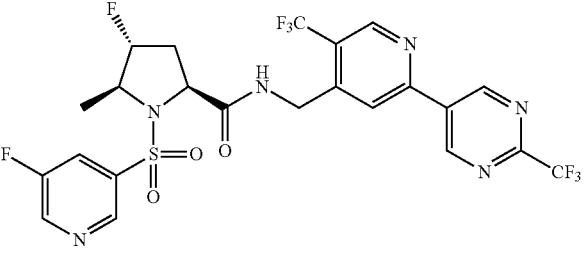 [SMILES: C[C@H]1[C@H](F)C[C@@H](C(=O)NCc2cc(-c3cnc(C(F)(F)F)nc3)ncc2C(F)(F)F)N1S(=O)(=O)c1cncc(F)c1]<br>Compound 3 | 0.021 | 19 | NR |
| 4 | 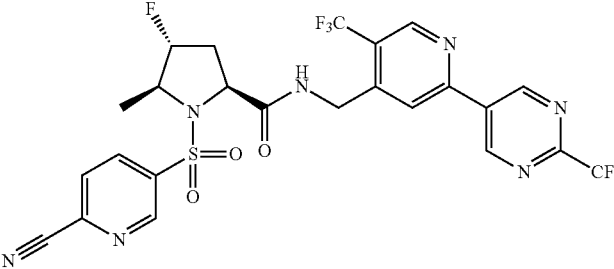 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(C#N)nc1]<br>Compound 4 | 0.041 | 3.7 | NR |
| 5 | 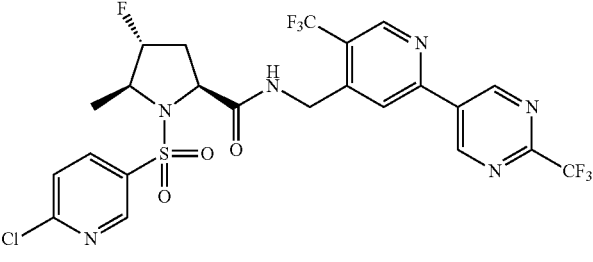 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(Cl)nc1]<br>Compound 5 | 0.005 | 6.6 | positive |

TABLE 5-continued

| Compound | H Ca2+ MAX | HLM | GSH trapping |
|---|---|---|---|
| 6 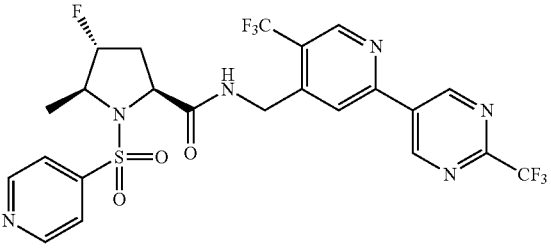 [SMILES: C[C@H]1[C@H](F)C[C@@H](C(=O)NCc2cc(-c3cnc(C(F)(F)F)nc3)ncc2C(F)(F)F)N1S(=O)(=O)c1ccncc1] Compound 6 | 0.638 | 19 | NR |

As compared to compounds 1 and 2, compound 3 is labile as indicated by a relatively high HLM clearance.

As compared to compounds 1 and 2, compound 4 has a low affinity on human TRPA1.

As compared to compounds 1 and 2, compound 6 has a low affinity on human TRPA1 and is relatively labile as indicated by a relatively high HLM clearance.

Example 21

Based on animal studies such as, for instance, human, monkey (e.g., cynomolgus), rat and/or mice, it is believed that plasma protein binding as measured in the manner described above will be less than 98%, less than 95%, less than 90%, or less than 85%, between about 80% and about 98%, between about 80% and about 95%, between about 80% and about 90%, about 98%, about 95%, about 90%, about 85% or about 80%.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compound of formula I

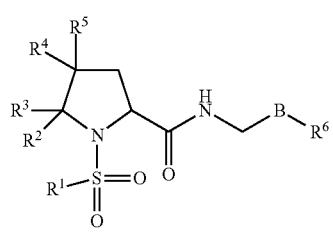

I wherein:
B is selected from $B^1$, $B^2$ and $B^3$;
$B^1$ is selected from;

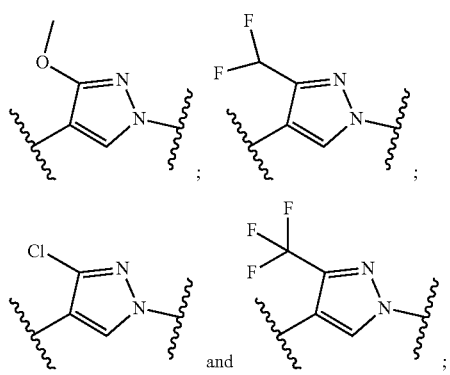

$B^2$ is selected from:

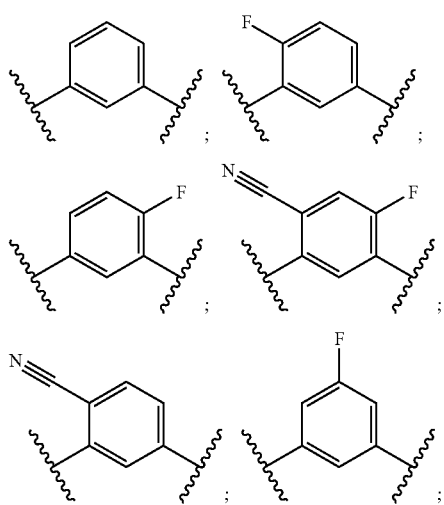

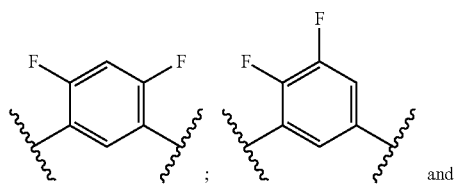

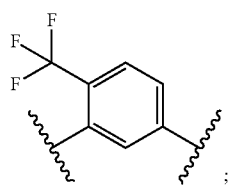
B³ is selected from:
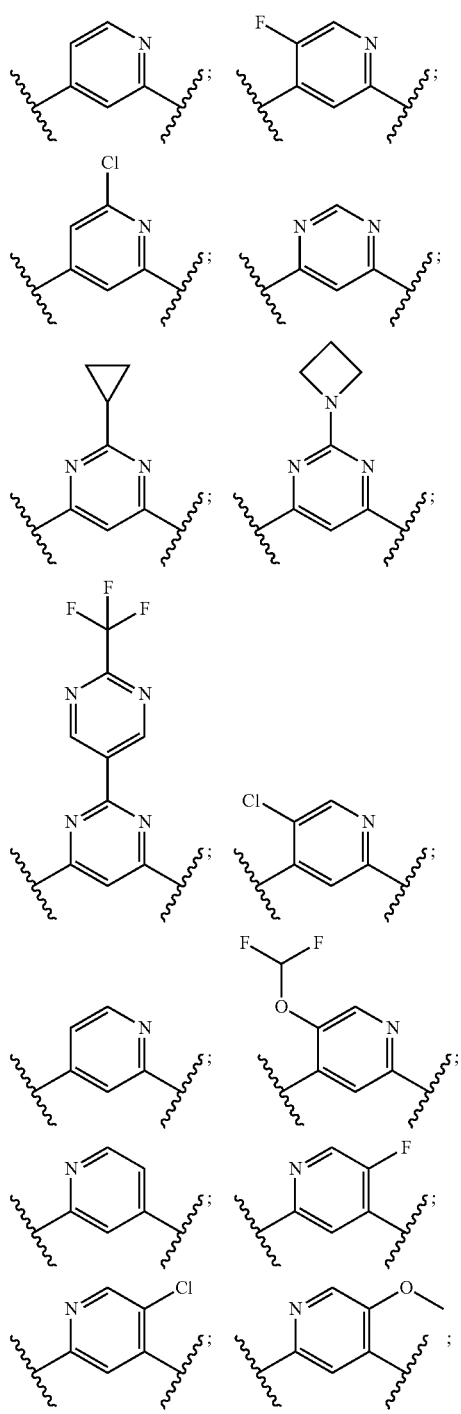
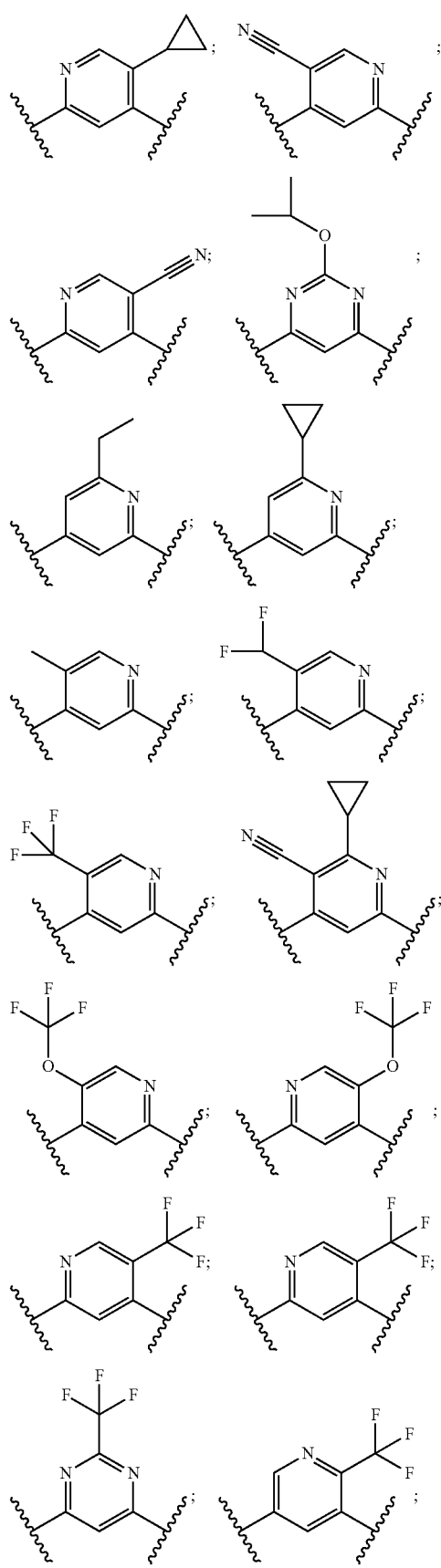

-continued

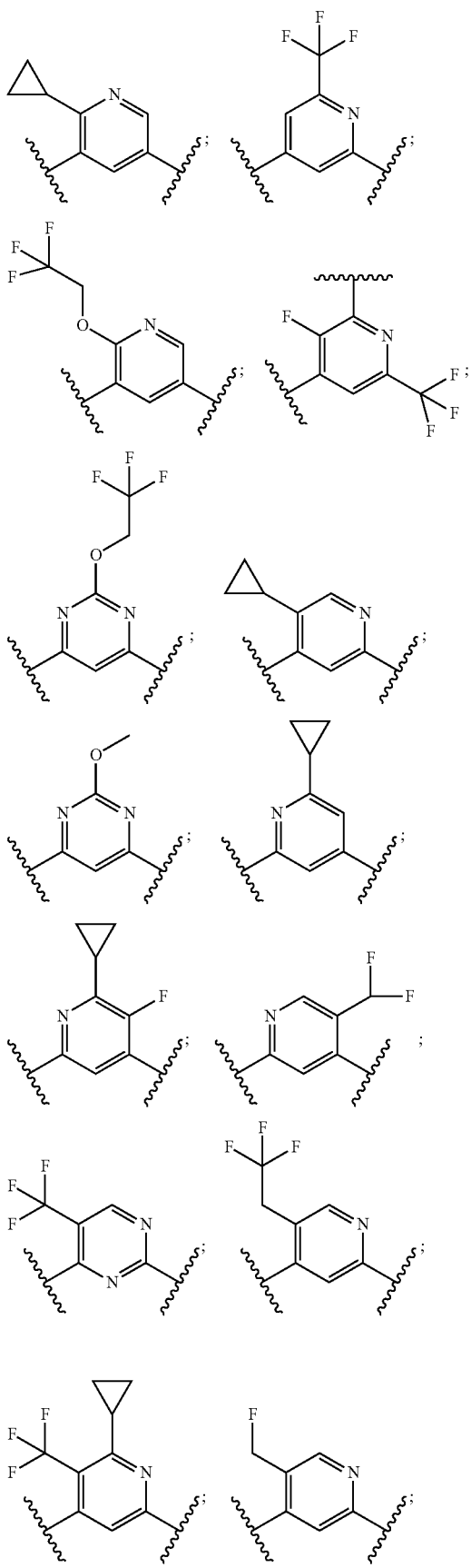

-continued

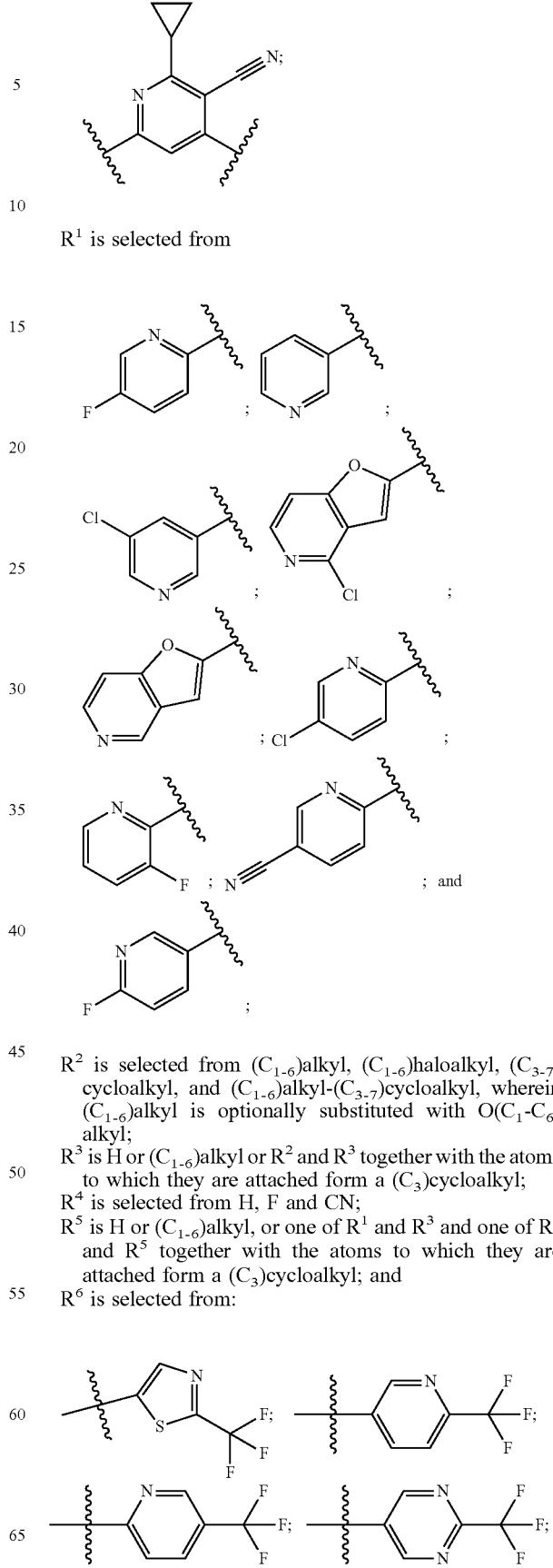

R¹ is selected from

R² is selected from $(C_{1-6})$alkyl, $(C_{1-6})$haloalkyl, $(C_{3-7})$cycloalkyl, and $(C_{1-6})$alkyl-$(C_{3-7})$cycloalkyl, wherein $(C_{1-6})$alkyl is optionally substituted with $O(C_1-C_6)$alkyl;

R³ is H or $(C_{1-6})$alkyl or R² and R³ together with the atoms to which they are attached form a $(C_3)$cycloalkyl;

R⁴ is selected from H, F and CN;

R⁵ is H or $(C_{1-6})$alkyl, or one of R¹ and R³ and one of R⁴ and R⁵ together with the atoms to which they are attached form a $(C_3)$cycloalkyl; and R⁶ is selected from:

-continued
and

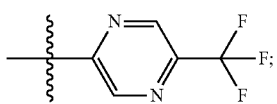

or a pharmaceutically acceptable salt thereof.

2. The compound of claim 1, wherein B is selected from:

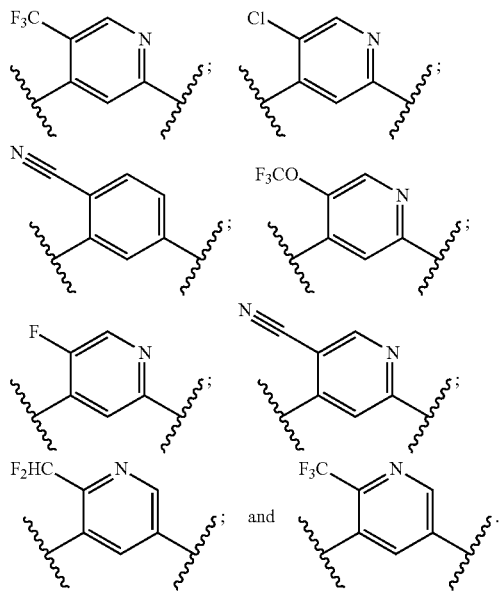

3. The compound of claim 1, wherein $R^1$ is substituted with one or more groups independently selected from Br, Cl, F, CN, $CH_3$, $CF_2H$ and $CF_3$.

4. The compound of claim 1, wherein $R^2$ is selected from:
(i) $(C_{1-6})$alkyl, optionally selected from $CH_3$, $CH_2CH_3$ and $C(CH_3)_3$;
(ii) $(C_{1-6})$haloalkyl, optionally $C(CF_3)_3$;
(iii) $CH_2OCH_3$; and
(iv) cyclopropyl.

5. The compound of claim 1, wherein: $R^3$ is H; $R^4$ is H, F or CN; and $R^5$ is H.

6. The compound of claim 1, wherein the group

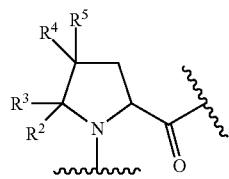

is selected from:

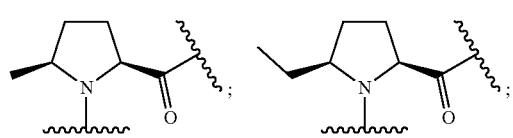

-continued

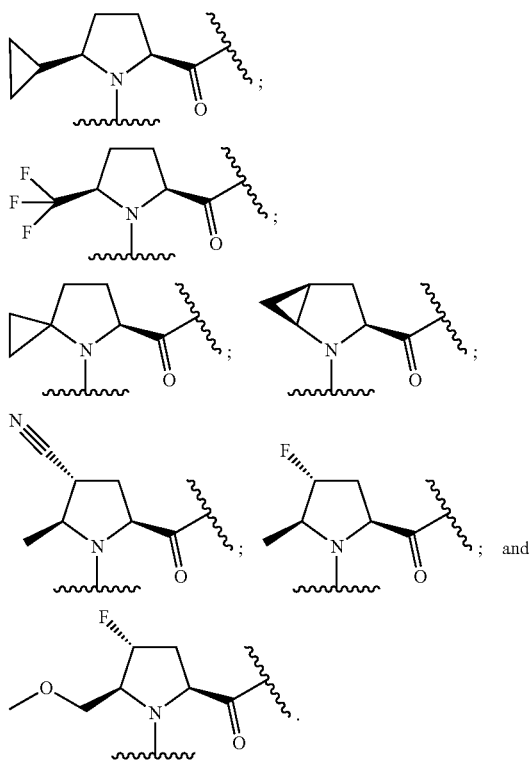

7. The compound of claim 1, wherein $R^6$ is:

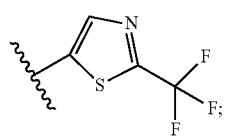 [SMILES: *c1cnc(C(F)(F)F)s1]

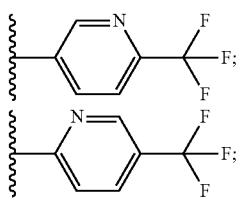

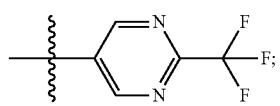

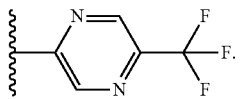

8. The compound of claim 1 wherein:
$R^2$ is $CH_3$, $R^3$ is H, $R^4$ is F, $R^5$ is H;
$R^6$ is
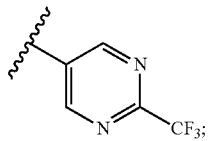
$R^1$ is selected from
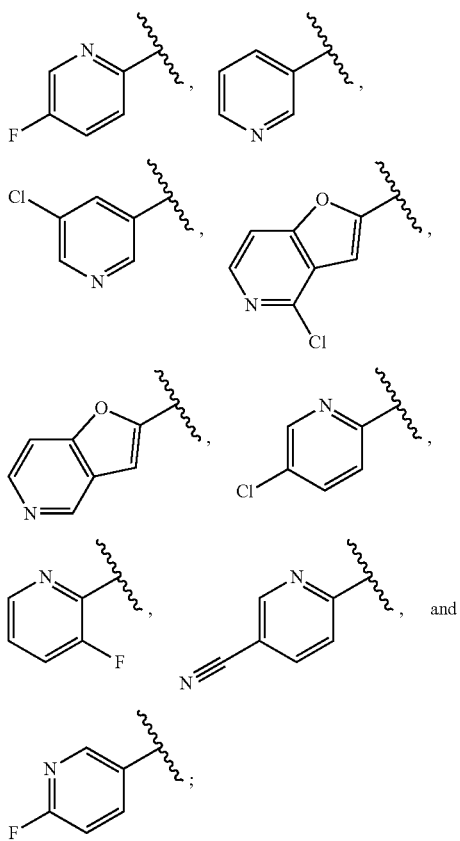
and
B is selected from
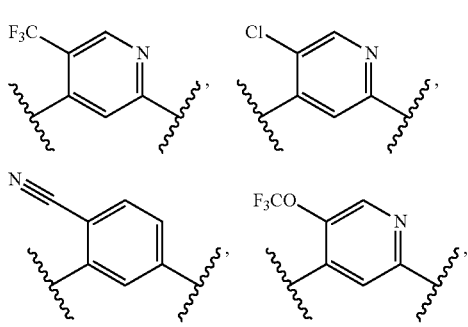
-continued
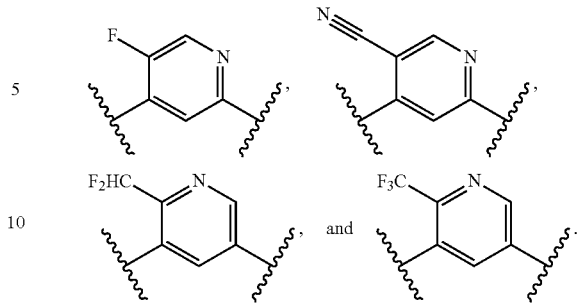
9. A compound selected from:
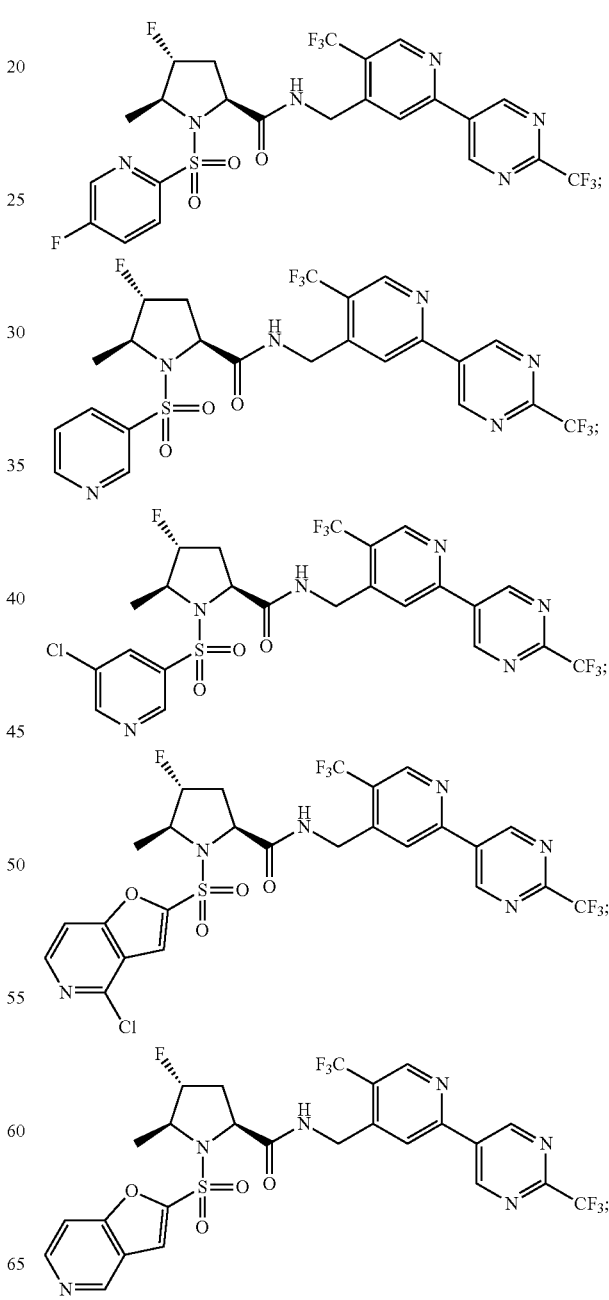

103
-continued
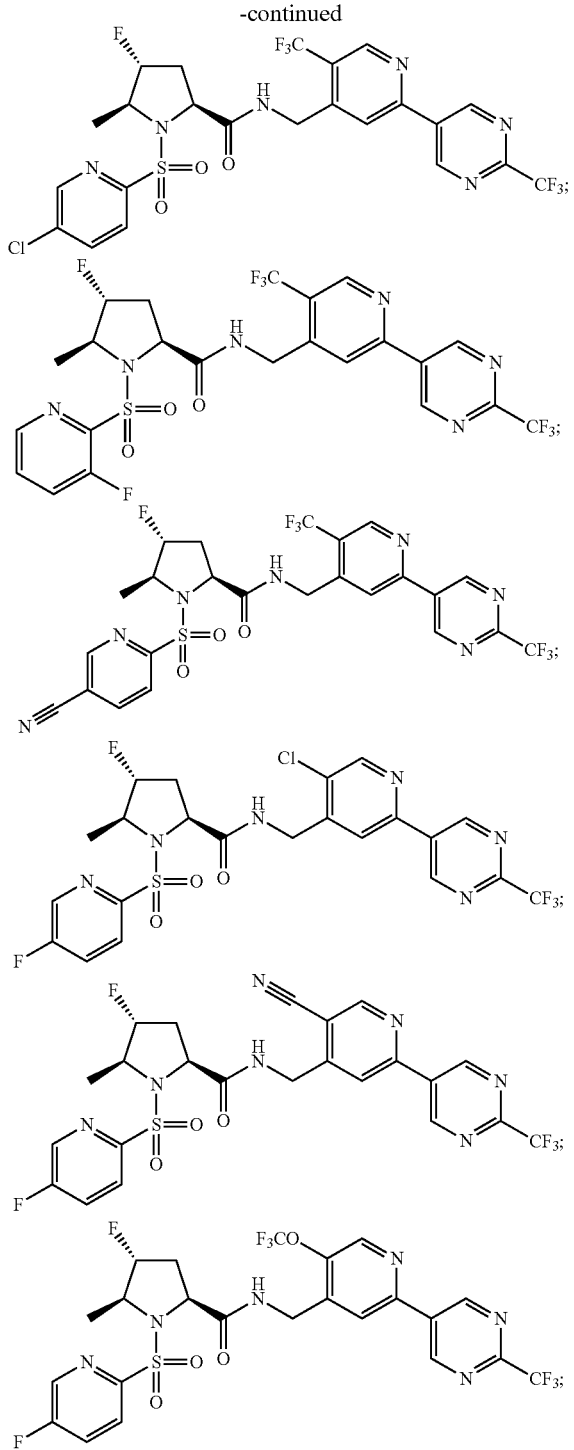
104
-continued
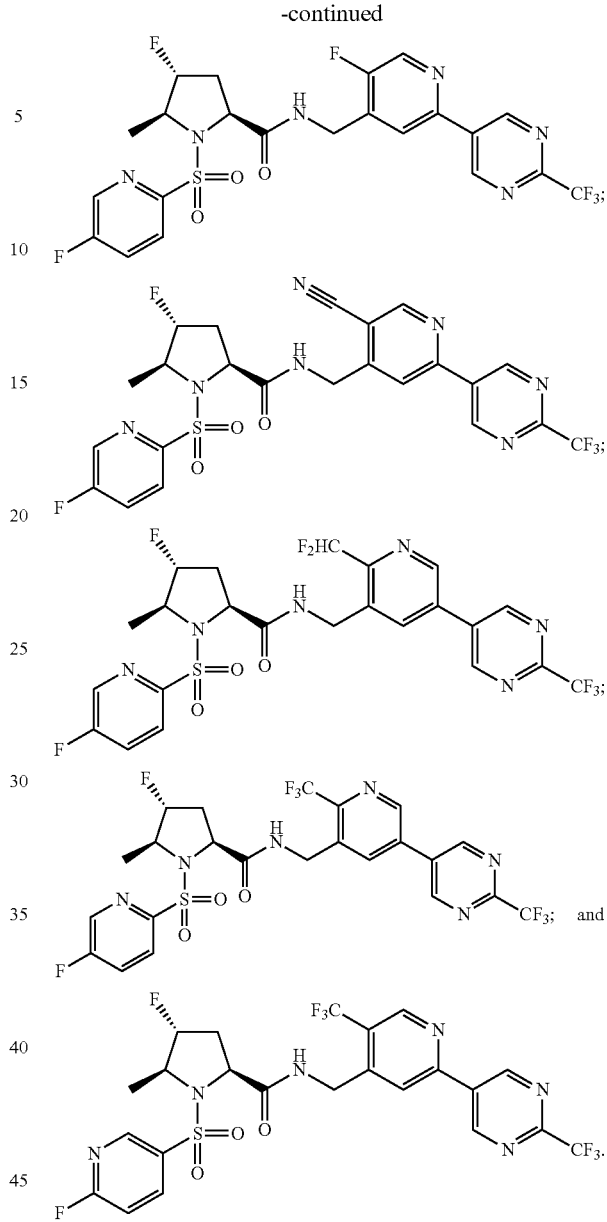
10. A pharmaceutical composition, comprising a compound as described in claim 1 or a pharmaceutically acceptable salt thereof, and a pharmaceutically acceptable carrier, diluent or excipient.
* * * * *